US009527881B2

(12) United States Patent
Macnevin et al.

(10) Patent No.: US 9,527,881 B2
(45) Date of Patent: Dec. 27, 2016

(54) STEROID ANALOGUES FOR NEUROPROTECTION

(75) Inventors: Christopher Macnevin, Durham, NC (US); Donald G. Stein, Atlanta, GA (US); Dennis C. Liotta, Atlanta, GA (US); Iqbal Sayeed, Atlanta, GA (US); David B. Guthrie, Atlanta, GA (US); Mark A. Lockwood, John's Creek, GA (US); Michael G. Natchus, Alpharetta, GA (US)

(73) Assignee: Emory University, Atlanta, GA (US)

( * ) Notice: Subject to any disclaimer, the term of this patent is extended or adjusted under 35 U.S.C. 154(b) by 170 days.

(21) Appl. No.: 12/918,036

(22) PCT Filed: Feb. 26, 2009

(86) PCT No.: PCT/US2009/035336
§ 371 (c)(1),
(2), (4) Date: Nov. 15, 2010

(87) PCT Pub. No.: WO2009/108804
PCT Pub. Date: Sep. 3, 2009

(65) Prior Publication Data
US 2011/0263553 A1 Oct. 27, 2011

Related U.S. Application Data

(60) Provisional application No. 61/031,567, filed on Feb. 26, 2008, provisional application No. 61/031,629, filed on Feb. 26, 2008, provisional application No. 61/032,315, filed on Feb. 28, 2008, provisional application No. 61/148,811, filed on Jan. 30, 2009.

(51) Int. Cl.
*A61K 31/58* (2006.01)
*A61K 31/56* (2006.01)
*A61P 21/00* (2006.01)
*C07G 3/00* (2006.01)
*C07J 21/00* (2006.01)
*C07J 41/00* (2006.01)
*C07J 7/00* (2006.01)
*C07J 9/00* (2006.01)

(52) U.S. Cl.
CPC ........................ *C07J 9/00* (2013.01)

(58) Field of Classification Search
USPC ........ 514/170, 169, 173, 177, 182; 552/517, 552/518, 607, 609; 540/34; 548/326.5, 491
See application file for complete search history.

(56) References Cited

U.S. PATENT DOCUMENTS

| 3,156,712 A | | 11/1964 | Mitchell et al. | |
| 3,196,169 A | | 7/1965 | Harvey et al. | |
| 3,455,903 A | * | 7/1969 | Shroff | C07J 41/00 540/519 |
| 4,186,128 A | * | 1/1980 | Warnant et al. | 540/97 |
| 5,232,917 A | * | 8/1993 | Bolger et al. | 514/176 |
| 6,331,534 B1 | * | 12/2001 | Berliner et al. | 514/177 |
| 9,303,058 B2 | * | 4/2016 | Leunis | C07J 63/008 |
| 2006/0217358 A1 | * | 9/2006 | Bordet et al. | 514/177 |
| 2009/0068257 A1 | * | 3/2009 | Leunis | C07J 9/005 424/450 |
| 2013/0210785 A1 | * | 8/2013 | Guthrie | A61K 31/58 514/171 |
| 2013/0245253 A1 | * | 9/2013 | Marx | C07J 7/001 540/113 |

FOREIGN PATENT DOCUMENTS

| EP | 2260052 | 12/2010 |
| WO | 02/30409 A2 | 4/2002 |

OTHER PUBLICATIONS

Tereza Solavikova et al. (Collect. Czech. Chem. Commun. (vol. 62) (1997)).*
Shoppee et al. (AN 61:1964:469340 HCAPLUS, Original reference No. 61:12056a-b, Journal of the Chemical Society (Sep. 1964) pp. 3388-3392).*
Shoppee et al. ( Journal of the Chemical Society (Sep. 1964) pp. 3388-3392).*
Kim et al. (AN 1987:168614, CAPLUS, DN 106:168614, original reference 106:27233a, 27236a, abstract Archives of Pharmcal. Research (1986), 9 (4), 215-17).*
Wermuth, "Similarity in Drugs: Reflection on Analogue Design," Drug Discovery Today, vol. 11, No. 7/8, Apr. 2006, pp. 348-354.*
"Prodrugs" in Modern Pharmaceutics (Banker et al. eds.) (3d ed. 1996), p. 596.*
Patent assignee—Pfizer & Co. (AN 1959:89665, DN 53:89665, HCAPLUS, Title Steroid Esters. Abstract of GB 804521).*
Gleason, et al., 1950, The Oppenauer Oxidation of Steroid Semicarbazones, , Journal of American Chemical Society, vol. 72, No. 4, pp. 1751-1752.
Allen, R. et al, 1978, Use of Homologous and Heterologous <125> I-Radioligands in the Radioimmunassay of Progesterone, Steroids, vol. 32, No. 4, pp. 467-486.
Gerristen, et al., 1996, Direct dynamics stimulation of FES-Assisted locomotion, SPIE, vol. 2718, pp. 481-491.
Gleason, et al., 1950, The Oppenauer Oxidation of Steroid Semicarbazones, Journal of American Chemical Society, vol. 72, No. 4, pp. 1751-1752.

(Continued)

*Primary Examiner* — Sabiha N Qazi
(74) *Attorney, Agent, or Firm* — Emory Patent Group

(57) ABSTRACT

Provided are steroid analogues functionalized with polar substituents at the C3 and/or C20 positions of the steroid ring system that exhibit improved water solubility. Also provided are pharmaceutical compositions comprising the steroid analogues and methods using the novel steroid analogues for the treatment and prevention of neurodegeneration in a patient following injury to the central nervous system.

3 Claims, 5 Drawing Sheets

(56) References Cited

OTHER PUBLICATIONS

Hartmann, et al., 2000, Synthesis and Evaluation of Novel Steroidal Oxime Inhibitors of P450 17(17αHydroxylase/C17-20-lyase) and 5α-reductase Types 1 and 2, J. Med. Chem, vol. 43, No. 22, pp. 4266-4277.
Kvasnica, et al., 2008, Platinum(II) complexes with steroidal esters of L-methionine and L-histidine: Synthesis, characterization and cytotoxic activity, Bioorganic & Medicinal Chemistry, vol. 16, pp. 3704-3713.
MacNevin et al., Development and Screening of Water-Soluble Analogues of Progesterone and Allopregnanolone in Models of Brain InjuryJ.Med.Chem., 2009, 52, 6012-6023.
Guthrie et al. Water-Soluble Progesterone Analogues are Effective, Injectable Treatments in Animal Models of Traumatic Brain Injury, ACS Med. Chem. Lett., 2012, 3, 362-366.

\* cited by examiner

Pharmacokinetic data for P1-31 and P1-33 dosed i.v. at 10 mg/kg.

Pharmacokinetic data for P1-131 dosed i.v. at 10 mg/kg.

Pharmacokinetic data for P1-186 dosed i.v. at 10 mg/kg.

STEROID ANALOGUES FOR NEUROPROTECTION

CROSS REFERENCE TO RELATED APPLICATIONS

This application claims the benefit of U.S. Provisional Application Nos. 61/031,567 and 61/031,629, both filed Feb. 26, 2008, U.S. Provisional Application No. 61/032,315, filed Feb. 28, 2008, and U.S. Provisional Application No. 61/148,811, filed Jan. 30, 2009, all which are incorporated herein by reference.

FIELD OF THE INVENTION

The present invention is in the area of pharmaceutical chemistry and specifically relates to certain steroid analogues, pharmaceutical compositions and methods for neuroprotection in the treatment and prevention of traumatic brain injury and brain injury caused by stroke.

BACKGROUND OF THE INVENTION

Brain injuries, including traumatic brain injury (TBI) and stroke, affect well over 2 million Americans each year and are a significant health concern worldwide. There are currently approximately 5.7 million stroke survivors in the US, many with permanent disabilities, and more than 5 million Americans who have suffered a TBI that in some cases results in the permanent need for help in performing daily activities. Traumatic brain injuries result from a blow or jolt to the head or a penetrating head injury that disrupts the function of the brain, with severity ranging from "mild," i.e., a brief change in mental status or consciousness to "severe," i.e., an extended period of unconsciousness or amnesia after the injury. In contrast, strokes are a result of diseases that affect the blood vessels that supply blood to the brain. A stroke occurs when a blood vessel that brings oxygen and nutrients to the brain either bursts (hemorrhagic stroke) or is clogged by a blood clot or some other mass (ischemic stroke). The majority of strokes are ischemic, however hemorrhagic strokes typically result in more severe injuries.

Despite several decades of effort, scientists have not yet found a pharmacological agent that consistently improves outcomes after stroke or TBI (see Sauerland, S. et al., *Lancet* 2004, 364, 1291-1292; Brain Trauma Foundation, American Association of Neurological Surgeons, Joint Section on Neurotrauma and Critical Care. Guidelines for the management of severe head injury. *J. Neurotrauma* 1996, 13, 641-734).

After TBI or stroke, inflammation is a principle cause of secondary damage and long-term damage. Following insults to the central nervous system, a cascade of physiological events leads to neuronal loss including, for example, an inflammatory immune response and excitotoxicity resulting from disrupting the glutamate, acetylcholine, cholinergic, $GABA_A$, and NMDA receptor systems. In these cases, a complex cascade of events leads to the delivery of blood-borne leucocytes to sites of injury to kill potential pathogens and promote tissue repair. However, the powerful inflammatory response has the capacity to cause damage to normal tissue, and dysregulation of the innate, or acquired immune response is involved in different pathologies.

In addition to TBI and stroke, inflammation is being recognized as a key component of a variety of nervous system disorders. It has long been known that certain diseases such as multiple sclerosis result from inflammation in the central nervous system, but it is only in recent years that it has been suggested that inflammation may significantly contribute to neurodegenerative disorders such as HIV-related dementia, Alzheimer's and prion diseases. It is now known that the resident macrophages of the central nervous system (CNS), the microglia, when activated may secrete molecules that cause neuronal dysfunction, or degeneration.

There is growing experimental evidence that progesterone, its metabolites and other gonadal steroids such as estrogen and possibly testosterone, are effective neuroprotective agents. Pre-clinical and clinical research demonstrates that the hormone progesterone is a potent neurosteroid that, acutely administered, can dramatically reduce cerebral edema, inflammation, tissue necrosis, and programmed cell death (see Djebaili, M. et al, *J. Neurotrauma* 2005, 22, 106-118; Pettus, E. H. et al., *Brain Res.* 2005, 1049, 112-119; Grossman, K. J. et al., *Brain Res,* 2004, 1008, 29-39; He, J. et al., *Exp. Neurol.* 2004, 189, 404-412; He, J. et al., *Reston. Neurol. Neurosci.* 2004, 22, 19-31; Djebaili, M. et al., *J. Neuroscience* 2004, 123, 349-359; Hoffman, S. W. et al., *Academy of Emergency Medicine,* 2001, 8, 496-497; and Wright, D. W. et al., *J. Neurotrauma.* 2001, 18, 901-909).

In vivo data has demonstrated progesterone's neuroprotective effects in injured nervous systems. For example, following a contusion injury, progesterone reduces the severity of post injury cerebral edema. The attenuation of edema by progesterone is accompanied by the sparing of neurons from secondary neuronal death and improvements in cognitive outcome (Roof et al. (1994) Experimental Neurology 129:64-69). Furthermore, following ischemic injury in rats, progesterone has been shown to reduce cell damage and neurological deficit (Jiang et al. (1996) Brain Research 735:101-107). A Phase II, single-center, controlled trial involving 100 moderate to severe TBI patients showed that 3 days of intravenous progesterone treatment reduced mortality by over 60% and significantly improved functional outcomes at 30 days post-injury (see Wright, D. A. et al., *Ann. Emerg. Med.* 2007, 49, 391).

PCT Publication WO 02/30409 to Emory University provides methods for conferring a neuroprotective effect on a population of cells in a subject following a traumatic injury to the central nervous system by administration of a progestin or progestin metabolite following a traumatic brain injury.

PCT Publication WO 06/102644 also to Emory University provides methods for the treatment or the prevention of neuronal damage in the CNS by tapered administration of a progestin or progestin metabolite following a traumatic or ischemic injury to the CNS to avoid withdrawal.

PCT Publication No. WO/2006/102596 to Emory University provides certain methods of treating a subject with a traumatic central nervous system injury, more particularly, a traumatic brain injury that include a therapy comprising a constant or a two-level dosing regime of progesterone.

Although progesterone has been shown to be neuroprotective in traumatic brain injury, its efficacy in stroke is less well defined. However, studies have indicated that progesterone may be useful in treating or preventing neurodegeneration following stroke (see Stein, D. (2005) The Case for Progesterone US *Ann. N.Y. Acad. Sci.* 1052:152-169; Murphy, et al. (2002) Progesterone Administration During Reperfusion, But Not Preischemia Alone, Reduces Injury in Ovariectomized Rats. *J. Cereb. Blood Flow & Metab.* 22:1181-1188; Murphy, et al. (2000) Progesterone Exacerbates Striatal Stroke Injury in Progesterone-Deficient Female Animals. *Stroke* 31:1173).

U.S. Pat. No. 6,245,757, now expired, to Research Corporation Technologies, Inc. provides a method for the treatment of ischemic damage, such as damage due to stroke or myocardial infarction comprising administering to a mammal afflicted with stroke an effective amount of a neuroprotective steroid in a suitable vehicle.

In addition to being a gonadal steroid, progesterone also belongs to a family of autocrine/paracrine hormones called neurosteroids. Neurosteroids are steroids that accumulate in the brain independently of endocrine sources and which can be synthesized from sterol precursors in nervous cells. These neurosteroids can potentiate GABA transmission, modulate the effects of glutamate, enhance the production of myelin, and prevent release of free radicals from activated microglia.

Various metabolites of progesterone have also been suggested to have neuroprotective properties. For instance, the progesterone metabolites allopregnanolone or epipregnanolone are positive modulators of the GABA receptor, increasing the effects of GABA in a manner that is independent of the benzodiazepines (Baulieu, E. E. (1992) *Adv. Biochem. Psychopharmacol.* 47:1-16; Robel et al. (1995) *Crit. Rev. Neurobiol.* 9:383-94; Lambert et al. (1995) *Trends Pharmacol. Sci.* 16:295-303; Baulieu, E. E. (1997) *Recent Prog. Horm. Res.* 52:1-32; Reddy et al. (1996) *Psychopharmacology* 128:280-92). In addition, these neurosteroids act as antagonists at the sigma receptor, which can activate the NMDA channel complex (Maurice et al. (1998) *Neuroscience* 83:413-28; Maurice et al. (1996) *J. Neurosci. Res.* 46:734-43; Reddy et al. (1998) *Neuroreport* 9:3069-73). These neurosteroids have also been shown to reduce the stimulation of cholinergic neurons and the subsequent release of acetylcholine by excitability. Numerous studies have shown that the cholinergic neurons of the basal forebrain are sensitive to injury and that excessive release of acetylcholine can be more excitotoxic than glutamate (Lyeth et al. (1992) *J. Neurotrauma* 9(2):S463-74; Hayes et al. (1992) *J. Neurotrauma* 9(1):S173-87).

As discussed above, following a traumatic injury to the central nervous system, a cascade of physiological events leads to neuronal loss. In addition, the injury is frequently followed by brain and/or spinal cord edema that enhances the cascade of injury and leads to further secondary cell death and increased patient mortality. Methods are needed for the in vivo treatment of traumatic CNS injuries that are successful at providing subsequent trophic support to remaining central nervous system tissue, and thus enhancing functional repair and recovery, under the complex physiological cascade of events which follow the initial insult.

Although successful, the use of progesterone itself as a therapeutic suffers from several drawbacks, including most notably its poor solubility and its potential for generating unwanted side effects. Therefore, there is a need for progesterone analogues that exhibit improved solubility and bioavailability for the treatment of ischemic, hemorrhagic or traumatic central nervous injury.

SUMMARY OF THE INVENTION

Provided are novel steroid analogues functionalized with polar groups at the C3 and C20 positions that exhibit greater water solubility than the parent compounds and are useful for the prevention and treatment of nervous system damage, in particular due to neurodegenerative reactions to injury or disease. In one embodiment, the steroid analogues of the invention are derivatized at the 3- and/or 20-positions of the steroid ring with polar amino acid substituents capable of forming water soluble salts. The amino acids may be either the naturally occurring or synthetic amino acids in either the D, L configuration or may be a mixture of D and L forms. In other embodiments, the steroid analogues are derivatized at the 3- and/or 20-positions with a carbohydrate or a substituted acyl group. The steroid analogues are optionally substituted with non-hydrogen substituents at the 9-, 1-, 2-, 3-, and 4-positions and may contain double bonds between C1 and C2, C4 and C5 and between C5 and C6.

In general embodiments, compounds, pharmaceutical compositions and methods of use of a compound of Formula I are provided:

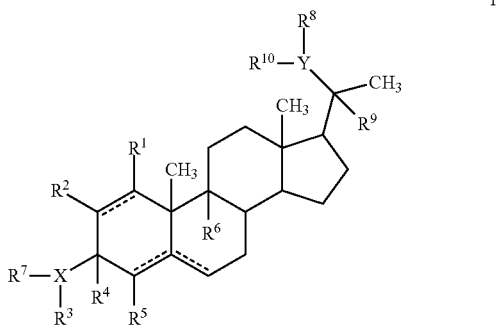

wherein X is O, N or S;

Y is O, N or S;

$R^1$, $R^2$, $R^5$ and $R^6$ are independently hydrogen, alkyl, halogen, hydroxyl cycloalkyl, cycloalkenyl, alkenyl, alkynyl, aryl, alkylaryl, arylalkyl, heterocyclic, heteroaryl, amino, thiol, alkoxy, sulfide, nitro, cyano, azide, sulfonyl, acyl, carboxyl, an ester, an amide, carbamate, carbonate, an amino acid residue or a carbohydrate;

$R^4$ is hydrogen or alkyl; $R^4$ together with $R^3$ and X forms an optionally substituted 5-6 membered heterocyclic or heteroaryl ring containing 1-4 nitrogen, oxygen or sulfur atoms; or $R^4$ and $R^7$ together form a double bond;

$R^3$ is hydrogen, optionally substituted acyl, a residue of an amino acid, a carbohydrate, monophosphate, diphosphate, triphosphate, —$OR^{11}$, —$NR^{11}R^{12}$; —C(O)R', where R' is alkyl, aryl, aralkyl, $OR^1$, $NR^1R^2$ or the residue of an amino acid; $R^3$ together with X and $R^4$ forms an optionally substituted 5-6 membered heterocyclic or heteroaryl ring containing 1-4 nitrogen, oxygen or sulfur atoms, or $R^3$ is absent;

$R^7$ is hydrogen or is absent, or $R^7$ together with $R^4$ forms a double bond;

$R^8$ is hydrogen, optionally substituted acyl, a residue of an amino acid, a carbohydrate, monophosphate, diphosphate, triphosphate, —$OR^{11}$, $NR^{11}R^{12}$; —C(O)R', where R' is alkyl, aryl, aralkyl, $OR^1$, $NR^1R^2$ or the residue of an amino acid; $R^8$ together with $R^9$ and Y forms an optionally substituted 5-6 membered heterocyclic or heteroaryl ring containing 1-4 nitrogen, oxygen or sulfur atoms, or $R^8$ absent;

$R^9$ is hydrogen or alkyl; $R^9$ together with Y and $R^8$ forms an optionally substituted 5-6 membered heterocyclic or heteroaryl ring containing 1-4 nitrogen, oxygen or sulfur atoms; or $R^9$ and $R^{10}$ together form a double bond;

$R^{10}$ is hydrogen or is absent, or $R^{10}$ together with $R^9$ forms a double bond;

$R^{11}$ is hydrogen, optionally substituted alkyl, hydroxyalkyl, aminoalkyl, monophosphate, diphosphate, triphosphate, the residue of an amino acid, a carbohydrate, an optionally substituted ester, or —C(O)R', where R' is alkyl, aryl, aralkyl, $OR^1$, $NR^1R^2$ or the residue of an amino acid;

$R^{12}$ is hydrogen or alkyl; and the dotted line indicates the presence of either a single bond or a double bond, wherein the valences of a single bond are completed by hydrogens, with certain provisos.

In more specific embodiments, a residue of an amino acid is connected to the steroid ring system at the carboxyl group of the amino acid. In other embodiments, a residue of an amino acid is connected to the steroid at the amino acid side chain. For example, amino acids that contain side chains with functional groups that are capable of forming a bond with a hydroxy or a ketone group may be bonded to the progestin ring by such a group. In other embodiments, the reactive groups on the amino acid may displace leaving groups formed on the progestin moiety to form a covalent bond. Non-limiting examples of amino acids with reactive groups in the side chain include lysine, cysteine, serine, tyrosine, aspartic acid, arginine and the like.

In another embodiment, the enantiomers of the compounds of Formula I are provided. In this embodiment, the stereochemical configuration of each asymmetric carbon is opposite that of the natural steroids and analogues of the natural steroids.

In specific embodiments of the invention, methods of treating or preventing damage resulting from nervous system injury or disease are provided, such as from traumatic brain injury or stroke, comprising administering a compound of Formula I or a pharmaceutically acceptable salt, ester or prodrug thereof in a pharmaceutically acceptable carrier to a patient in need thereof. In some embodiments, the damage is due to inflammation initiated by a TBI. In other embodiments, methods of treating or preventing neurodegeneration resulting from ischemic CNS injuries, in particular from ischemic stroke are provided comprising administering a compound of the invention to a patient in need thereof. In yet other embodiments, methods of treating or preventing neurodegeneration resulting from hemorrhagic CNS injuries, in particular from hemorrhagic stroke are provided comprising administering a compound of the invention to a patient in need thereof. The methods can alleviate the initial damage to the CNS. Therefore, in some embodiments, the compounds are administered to a patient at risk of a CNS injury, in particular to a patient at risk of a stroke. The compounds are also effective at reducing or preventing secondary injuries. Therefore, in other embodiments, the compounds are administered to a patient who has suffered a CNS injury within a window of opportunity after the initial insult. The initial insult can be either a TBI or a stroke, whether that be an ischemic or hemorrhagic stroke. In other embodiments, the neural damage occurs from a disease or disorder such as multiple sclerosis or Amyotrophic Lateral Sclerosis (ALS). Pharmaceutical compositions, including in combination with additional neuroprotective agents, are also provided.

DETAILED DESCRIPTION OF THE INVENTION

Figure 1:
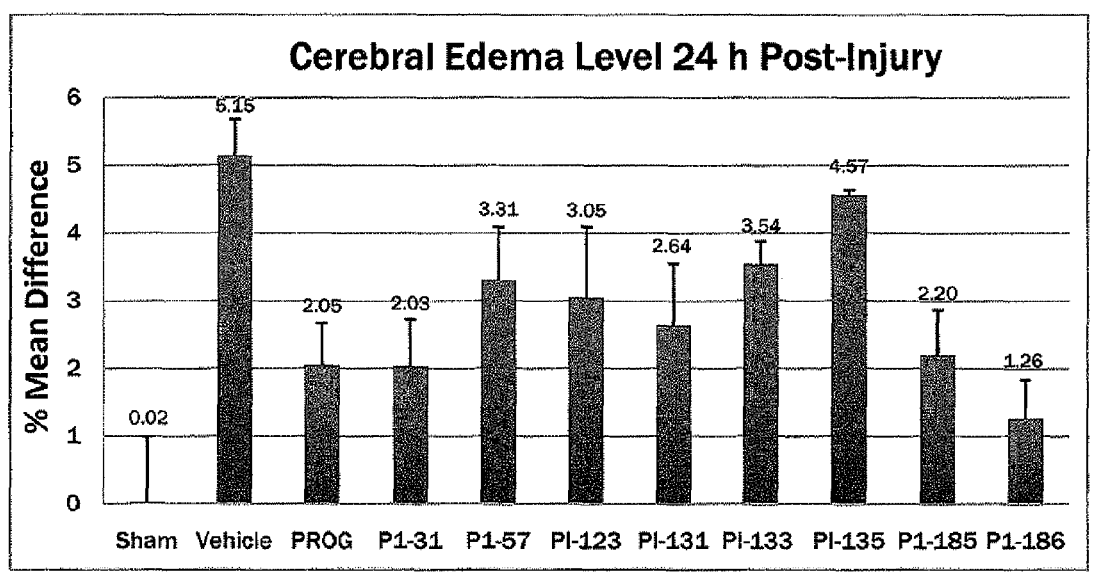
FIG. 1 shows cerebral edema assay data for selected steroid analogues.

Progesterone is lipid-soluble and essentially water insoluble. Therefore, the intravenous administration of progesterone is difficult in a clinical setting and the dose is limited by the low aqueous solubility of the compound. The present invention provides novel steroid analogues that comprise polar groups and exhibit increased aqueous solubility. Also provided are pharmaceutically acceptable salts, esters and prodrugs of the steroid analogues. The compounds, salts, esters and prodrugs provided are useful for the treatment or prevention of central nervous system injury, particularly for the treatment or prevention of damage arising from a traumatic brain injury and the treatment or prevention of injuries occurring from stroke.

The term "steroid analogues" as used herein is intended to encompass analogues of progesterone, analogues of progesterone metabolites or derivatives and other non-progestin steroid compounds. The steroid analogues of the invention exhibit increased solubility in aqueous solvents and are capable of forming pharmaceutically acceptable salts that further increase their aqueous solubility. Also provided are pharmaceutical compositions comprising the inventive steroid analogues, pharmaceutically acceptable salts, esters or prodrugs thereof, and methods for the treatment or prevention of CNS injuries, including traumatic brain injury and stroke. In particular, the present invention relates to steroid analogues that comprise amino acid residues, carbohydrates or other suitable polar groups at the 3- and/or 20-positions of the steroid ring system. The improved water solubility of the steroid analogues of the invention can facilitate the administration of the compounds, in particular intravenous administration, which provides the fastest possible exposure of the active agent to the brain or other CNS sites where it is needed, increasing the efficacy of the drug. In addition, the inventive steroid analogs can minimize undesired side effects that are typically accompany acute or prolonged treatment with progesterone, such as sleepiness, reduced arousal and increased blood clotting.

I. Compounds of the Invention

The compounds of the present invention are steroid analogues that are modified to comprise polar groups and exhibit a greater aqueous solubility than the naturally occurring parent compounds. In one embodiment, analogues of steroid compounds are provided that are modified at the 3- and/or 20-position of the steroid ring system to incorporate polar groups. The ring numbering shown below for the structure of progesterone (PROG) is maintained throughout this document to avoid ambiguity.

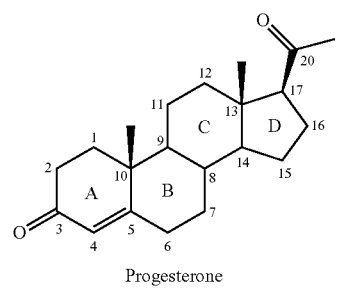

Progesterone

Substituents on the steroid analogues that lie below the plane of the paper as drawn are termed in the "α" or "alpha" configuration. Substituents that lie above the plane of the paper are termed in the "β" or "beta" configuration. For example the two methyl groups shown in the progesterone structure below are in the beta configuration.

In one embodiment of the invention are provided steroid analogues, such as progesterone, pregnenolone and the like, comprising an amino acid residue, a carbohydrate or other polar group bonded to the 3-position of the steroid ring system. In another embodiment of the invention, steroid analogues that comprise an amino acid residue, a carbohydrate or other polar group bonded to the 20-position of the ring system are provided. In still another embodiment, steroid analogues comprising amino acid residues and/or carbohydrates or other polar groups at the 3- and at the 20-positions of the ring system are provided. The inventive steroid analogues have greater aqueous solubility than the parent compounds and are thus advantageous for administration, in particular in situations in which rapid availability and effective dosing of the compounds are critical. In some embodiments, the steroid analogues comprise a basic nitrogen group that enables the formation of pharmaceutically acceptable salts and prodrugs. The inventive steroid analogues are useful for the treatment or prevention of central nervous system injury, particularly traumatic brain injury and stroke.

In one embodiment, the invention provides a steroid analogue of Formula I:

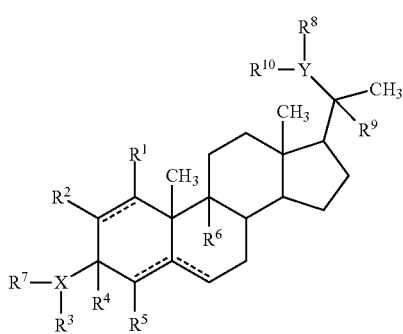

I or a pharmaceutically acceptable salt, ester or prodrug thereof,
wherein X is O, N or S;
Y is O, N or S;
$R^1$, $R^2$, $R^5$ and $R^6$ are independently hydrogen, alkyl, halogen, hydroxyl cycloalkyl, cycloalkenyl, alkenyl, alkynyl, aryl, alkylaryl, arylalkyl, heterocyclic, heteroaryl, amino, thiol, alkoxy, sulfide, nitro, cyano, azide, sulfonyl, acyl, carboxyl, an ester, an amide, carbamate, carbonate, an amino acid residue or a carbohydrate;
$R^4$ is hydrogen or alkyl; $R^4$ together with $R^3$ and X forms an optionally substituted 5-6 membered heterocyclic or heteroaryl ring containing 1-4 nitrogen, oxygen or sulfur atoms; or $R^4$ and $R^7$ together form a double bond;
$R^3$ is hydrogen, optionally substituted acyl, a residue of an amino acid, a carbohydrate, monophosphate, diphosphate, triphosphate, —$OR^{11}$, —$NR^{11}R^{12}$; —C(O)R', where R' is alkyl, aryl, aralkyl, $OR^1$, $NR^1R^2$ or the residue of an amino acid; $R^3$ together with X and $R^4$ forms an optionally substituted 5-6 membered heterocyclic or heteroaryl ring containing 1-4 nitrogen, oxygen or sulfur atoms, or $R^3$ is absent;
$R^7$ is hydrogen or is absent, or $R^7$ together with $R^4$ forms a double bond;
$R^8$ is hydrogen, optionally substituted acyl, a residue of an amino acid, a carbohydrate, monophosphate, diphosphate, triphosphate, —$OR^{11}$, —$NR^{11}R^{12}$; —C(O)R', where R' is alkyl, aryl, aralkyl, $OR^1$, $NR^1R^2$ or the residue of an amino acid; $R^8$ together with $R^9$ and Y forms an optionally substituted 5-6 membered heterocyclic or heteroaryl ring containing 1-4 nitrogen, oxygen or sulfur atoms, or $R^8$ absent;
$R^9$ is hydrogen, alkyl; $R^9$ together with Y and $R^8$ forms an optionally substituted 5-6 membered heterocyclic or heteroaryl ring containing 1-4 nitrogen, oxygen or sulfur atoms, or $R^9$ and $R^{10}$ together form a double bond;
$R^{10}$ is hydrogen or is absent, or $R^{10}$ together with $R^9$ forms a double bond;
$R^{11}$ is hydrogen, optionally substituted alkyl, hydroxyalkyl, aminoalkyl, monophosphate, diphosphate, triphosphate, the residue of an amino acid, a carbohydrate, an optionally substituted ester, or —C(O)R', where R' is $OR^1$, $NR^1R^2$, alkyl, aryl, aralkyl, or the residue of an amino acid;
$R^{12}$ is hydrogen or alkyl; and the dotted line indicates the presence of either a single bond or a double bond, wherein the valences of a single bond are completed by hydrogens, provided that at least one of $XR^3R^7$ or $YR^8R^{10}$ is not =O or OH; and that if the dotted line between C4 and C5 or between C5 and C6 represents a double bond then the other dotted line between C4 and C5 or between C5 and C6 represents a single bond; and with the proviso that neither $XR^3R^7$ nor $YR^8R^{10}$ represent an ester of aspartic acid, glutamic acid, gamma amino butyric acid or α-2-(hydroxyethylamino)-propionic acid; and with the proviso that when Y is N, $R^8$ does not represent aspartic acid, glutamic acid, gamma amino butyric acid or α-2-(hydroxyethylamino)-propionic acid.

In one embodiment of Formula I, $R^3$ is hydrogen, optionally substituted acyl, a residue of an amino acid, a carbohydrate, —$OR^{11}$, —$NR^{11}R^{12}$ or $R^3$ is absent; $R^4$ is hydrogen or alkyl, or $R^4$ and $R^7$ together form a double bond; $R^8$ is hydrogen, optionally substituted acyl, a residue of an amino acid, a carbohydrate, —$OR^{11}$, —$NR^{11}R^{12}$, or $R^8$ is absent; $R^9$ is hydrogen or alkyl, or $R^9$ and $R^{10}$ together form a double bond; and $R^{11}$ is a residue of an amino acid, a carbohydrate, or an optionally substituted ester.

In some embodiments, compounds of Formula I are provided wherein: $R^3$ is hydrogen, optionally substituted acyl, a residue of an amino acid, a carbohydrate, —$OR^{11}$, —$NR^{11}R^{12}$ or $R^3$ is absent; $R^8$ is hydrogen, optionally substituted acyl, a residue of an amino acid, a carbohydrate, —$OR^{11}$, —$NR^{11}R^{12}$ or $R^8$ absent; and $R^{11}$ is the residue of an amino acid, a carbohydrate or an optionally substituted ester.

In one embodiment, $R^1$, $R^2$, $R^5$ and $R^6$ are independently hydrogen, alkyl, halogen or hydroxyl.

In another embodiment, $R^1$, $R^2$, $R^5$ and $R^6$ are independently methyl, ethyl or propyl.

In still another embodiment, $R^1$, $R^2$, $R^5$ and $R^6$ are independently thiomethyl, hydroxymethyl or cyano.

In another embodiment, $R^1$, $R^2$, $R^5$ and $R^6$ are independently vinyl or ethynyl.

In still another embodiment, $R^1$, $R^2$, $R^5$ and $R^6$ are independently fluoro, bromo, chloro or iodo.

In still another embodiment, $R^4$ and $R^9$ are independently hydrogen or methyl.

In some embodiments, X and Y are O. In other embodiments, X is O and Y is N or X is N and Y is O. In other embodiments, both X and Y are N. In certain embodiments in which Y is O, $R^9$ and $R^{10}$ come together to form a double bond.

In certain embodiments, one of $R^3$ and $R^8$ is a residue of an amino acid. In particular embodiments, the amino acid is a naturally occurring amino acid. In certain embodiments, $R^3$ is a residue of an amino acid. In certain other embodiments, $R^8$ is a residue of an amino acid. In yet further embodiments, both $R^3$ and $R^8$ are residues of an amino acid.

In other embodiments, $R^3$ is a carbohydrate. In another embodiment, $R^8$ is a carbohydrate.

In one embodiment of Formula I, X is O, $R^3$ is the residue of an amino acid, and $R^7$ is absent.

In another embodiment of Formula I, Y is O, $R^8$ is the residue of an amino acid, and $R^{10}$ is absent;

In another embodiment of Formula I, X is N; $R^7$ together with $R^4$ form a double bond; $R^3$ is $OR^{11}$ or $NR^{11}R^{12}$; and $R^{11}$ is the residue of an amino acid or a carbohydrate.

In another embodiment of Formula I, Y is N; $R^{10}$ together with $R^9$ form a double bond; $R^8$ is $OR^{11}$ or $NR^{11}R^{12}$; and $R^{11}$ is the residue of an amino acid or a carbohydrate.

In another embodiment of Formula I, X is O; $R^3$ is the residue of a naturally occurring amino acid or a carbohydrate; $R^7$ is absent; Y is O; $R^8$ is absent; and $R^9$ and $R^{10}$ together form a double bond.

In still another embodiment, Y is O; $R^8$ is the residue of a naturally occurring amino acid or a carbohydrate; $R^{10}$ is absent; X is O; $R^7$ is absent; and $R^3$ and $R^4$ together form a double bond.

In another embodiment of Formula I, X is O; $R^3$ is the residue of an amino acid; $R^7$ is absent; Y is N; $R^{10}$ together with $R^9$ form a double bond; $R^8$ is $OR^{11}$ or $NR^{11}R^{12}$; and $R^{11}$ is the residue of an amino acid or a carbohydrate.

In yet another embodiment of Formula I, X is N; $R^7$ together with $R^4$ form a double bond; $R^3$ is $OR^{11}$ or $NR^{11}R^{12}$; $R^{11}$ is the residue of an amino acid or a carbohydrate; Y is O; $R^8$ is the residue of an amino acid; and $R^{10}$ is absent.

In another embodiment of Formula I, X is O; $R^3$ is the residue of an amino acid or a carbohydrate; $R^7$ is absent; Y is O, $R^8$ is the residue of an amino acid or a carbohydrate, and $R^{10}$ is absent.

In yet another embodiment of Formula I, X is N; $R^7$ together with $R^4$ form a double bond; $R^3$ is $OR^{11}$ or $NR^{11}R^{12}$; Y is N; $R^{10}$ together with $R^9$ form a double bond; $R^8$ is $OR^{11}$ or $NR^{11}R^{12}$; and $R^{11}$ is the residue of an amino acid or a carbohydrate.

In another embodiment, X is N, $R^7$ together with $R^4$ form a double bond, and $R^3$ is —C(O)R'.

In another embodiment, Y is N, $R^9$ and $R^{10}$ together form a double bond, and $R^8$ is —C(O)R'.

In another embodiment, X is O and $R^3$ is monophosphate, diphosphate, triphosphate, In another embodiment, Y is O and $R^8$ is monophosphate, diphosphate, triphosphate, In yet another embodiment of Formula I, X is O; $R^3$ is the residue of an amino acid; $R^7$ is absent; $R^1$, $R^2$, $R^4$, $R^5$ and $R^6$ are independently hydrogen, alkyl, halogen or hydroxyl.

In yet another embodiment of Formula I, X is O; $R^3$ is the residue of an amino acid; $R^7$ is absent; $R^1$, $R^2$, $R^4$, $R^5$ and $R^6$ are hydrogen.

In another embodiment of Formula I, Y is O; $R^8$ is the residue of an amino acid; $R^{10}$ is absent; $R^1$, $R^2$, $R^4$, $R^5$ and $R^6$ are independently hydrogen, alkyl, halogen or hydroxyl.

In still another embodiment of Formula I, Y is O; $R^8$ is the residue of an amino acid; $R^{10}$ is absent; $R^1$, $R^2$, $R^4$, $R^5$ and $R^6$ are hydrogen.

In one embodiment of Formula I, the dotted line between C4 and C5 represents a single bond and the dotted line between C5 and C6 represents a single bond.

In another embodiment of Formula I, the dotted line between C4 and C5 represents a single bond and the dotted line between C5 and C6 represents a double bond.

In another embodiment of Formula I, the dotted line between C4 and C5 represents a double bond and the dotted line between C5 and C6 represents a single bond.

In still another embodiment, the dotted line between C1 and C2 represents a single bond. In another embodiment, the dotted line between C1 and C2 represents a double bond.

In certain embodiments of Formula I, a residue of an amino acid is connected to the steroid ring system at the carboxyl group of the amino acid. In other embodiments, a residue of an amino acid is connected to the steroid at the amino acid side chain. For example, amino acids that contain side chains with functional groups that are capable of forming a bond with a hydroxy or a ketone group may be boded to the steroid ring by such a group. In other embodiments, the reactive groups on the amino acid side chains may displace leaving groups formed on the steroid moiety to form a covalent bond. Non-limiting examples of amino acids with reactive groups in the side chain include lysine, cysteine, serine, tyrosine, aspartic acid, arginine and the like.

The amino acid(s) in any of the embodiments of the invention described herein may be naturally occurring or synthetic amino acids and may be in the D or L stereoisomeric form or may exist as a D, L mixture. For example the 20 naturally occurring α-amino acids in the L-configuration are encompassed by the invention as well as α-amino acids in the D-configuration. Synthetic amino acids in either stereoisomeric form are also encompassed.

In one embodiment, a compound of Formula I with the stereochemical configuration of Formula Ia is provided:

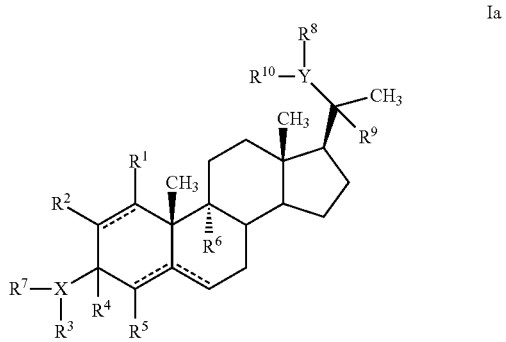

wherein the definition of variables X, Y, $R^1$, $R^2$, $R^3$, $R^4$, $R^5$, $R^6$, $R^7$, $R^8$, $R^9$ and $R^{10}$ is as defined in Formula I above.

In another embodiment, a compound of Formula I with the stereochemical configuration of Formula Ib is provided:

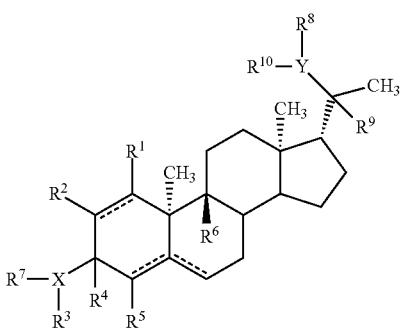

wherein the definition of variables X, Y, $R^1$, $R^2$, $R^3$, $R^4$, $R^5$, $R^6$, $R^7$, $R^8$, $R^9$ and $R^{10}$ is as defined in Formula I above.

In another embodiment, a progesterone or steroid analogue Formula II is provided:

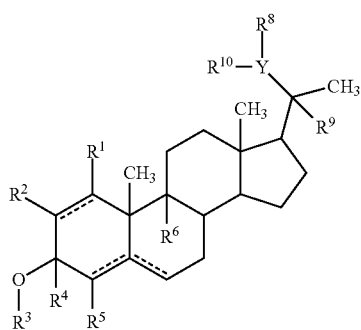

or a pharmaceutically acceptable salt, ester or prodrug thereof, wherein Y is O, N or S;

$R^1$, $R^2$, $R^5$ and $R^6$ are independently hydrogen, alkyl, halogen, hydroxyl cycloalkyl, cycloalkenyl, alkenyl, alkynyl, aryl, alkylaryl, arylalkyl, heterocyclic, heteroaryl, amino, thiol, alkoxy, sulfide, nitro, cyano, azide, sulfonyl, acyl, carboxyl, an ester, an amide, carbamate, carbonate, an amino acid residue or a carbohydrate;

$R^3$ is hydrogen, optionally substituted acyl, a residue of an amino acid, monophosphate, diphosphate, triphosphate, a carbohydrate; —C(O)R', where R' is alkyl, aryl, aralkyl, $OR^1$, $NR^1R^2$ or the residue of an amino acid; or $R^3$ together with the oxygen and $R^4$ forms an optionally substituted 5-6 membered heterocyclic or heteroaryl ring containing 1-4 nitrogen, oxygen or sulfur atoms;

$R^4$ is hydrogen or alkyl, or $R^4$ together with $R^3$ and the oxygen atom forms an optionally substituted 5-6 membered heterocyclic or heteroaryl ring containing 1-4 nitrogen, oxygen or sulfur atoms;

$R^8$ is hydrogen, optionally substituted acyl, a residue of an amino acid, a carbohydrate, monophosphate, diphosphate, triphosphate, —$OR^{11}$, —$NR^{11}R^{12}$; —C(O)R', where R' is alkyl, aryl, aralkyl, $OR^1$, $NR^1R^2$ or the residue of an amino acid; $R^8$ together with $R^9$ and Y forms an optionally substituted 5-6 membered heterocyclic or heteroaryl ring containing 1-4 nitrogen, oxygen or sulfur atoms, or $R^8$ is absent;

$R^9$ is hydrogen or alkyl; $R^9$ together with Y and $R^8$ forms an optionally substituted 5-6 membered heterocyclic or heteroaryl ring containing 1-4 nitrogen, oxygen or sulfur atoms; or $R^9$ and $R^{10}$ together form a double bond;

$R^{10}$ is hydrogen or absent, or $R^{10}$ together with $R^9$ form a double bond;

$R^{11}$ is hydrogen, optionally substituted alkyl, hydroxyalkyl, aminoalkyl, monophosphate, diphosphate, triphosphate, the residue of an amino acid, a carbohydrate, optionally substituted acyl, or —C(O)R', where R' is alkyl, aryl, aralkyl, $OR^1$, $NR^1R^2$, or the residue of an amino acid;

$R^{12}$ is hydrogen or alkyl; and the dotted lines indicate the presence of either a single bond or a double bond, wherein the valences of a single bond are completed by hydrogens, provided that if the dotted line between C4 and C5 or between C5 and C6 represents a double bond then the other dotted line between C4 and C5 or between C5 and C6 represents a single bond; and with the proviso that neither $R^3$ nor $YR^8R^{10}$ represent an ester of aspartic acid, glutamic acid, gamma amino butyric acid or α-2-(hydroxyethylamino)-propionic acid; and with the proviso that when Y is N, $R^8$ does not represent aspartic acid, glutamic acid, gamma amino butyric acid or α-2-(hydroxyethylamino)-propionic acid.

In one embodiment of Formula II, $R^3$ is hydrogen, optionally substituted acyl, a residue of an amino acid or a carbohydrate; $R^8$ is hydrogen, optionally substituted acyl, a residue of an amino acid, a carbohydrate, —$OR^{11}$, —$NR^{11}R^{12}$ or $R^8$ is absent; and $R^{11}$ is the residue of an amino acid, a carbohydrate or optionally substituted acyl.

In some embodiments, Y is O. In other embodiments, Y is N. In certain embodiments in which Y is O, $R^9$ and $R^{10}$ come together to form a double bond. In certain embodiments, one of $R^3$ and $R^8$ is a residue of an amino acid. In particular embodiments, the amino acid is a naturally occurring amino acid. In certain embodiments, $R^3$ is a residue of an amino acid. In certain other embodiments, $R^8$ is a residue of an amino acid. In yet further embodiments, both $R^3$ and $R^8$ are residues of an amino acid.

In one embodiment, $R^1$, $R^2$, $R^5$ and $R^6$ are independently hydrogen, alkyl, halogen or hydroxyl.

In another embodiment, $R^1$, $R^2$, $R^5$ and $R^6$ are independently methyl, ethyl or propyl.

In still another embodiment, $R^1$, $R^2$, $R^5$ and $R^6$ are independently thiomethyl, hydroxymethyl or cyano.

In another embodiment, $R^1$, $R^2$, $R^5$ and $R^6$ are independently vinyl or ethynyl.

In still another embodiment, $R^1$, $R^2$, $R^5$ and $R^6$ are independently fluoro, bromo, chloro or iodo.

In still another embodiment, $R^4$ and $R^9$ are independently hydrogen or methyl.

In one embodiment of Formula II, Y is O; $R^8$ is the residue of an amino acid; and $R^{10}$ is absent.

In another embodiment of Formula II, Y is N; $R^{10}$ together with $R^9$ form a double bond; $R^8$ is $OR^{11}$; and $R^{11}$ is the residue of an amino acid or a carbohydrate.

In another embodiment of Formula II, Y is N; $R^{10}$ together with $R^9$ form a double bond; $R^8$ is —$NR^{11}R^{12}$; $R^{11}$ is the residue of an amino acid or a carbohydrate; and $R^{12}$ is hydrogen.

In another embodiment of Formula II, $R^3$ is the residue of a naturally occurring amino acid or a carbohydrate; $R^4$ is hydrogen; Y is O; $R^{10}$ together with $R^9$ form a double bond; and $R^8$ is absent.

In another embodiment of Formula II, $R^3$ is a carbohydrate; $R^4$ is hydrogen; Y is O; $R^{10}$ together with $R^9$ form a double bond; and $R^8$ is absent.

In another embodiment of Formula II, $R^3$ is the residue of a naturally occurring amino acid or a carbohydrate; $R^4$ is hydrogen; Y is O; $R^8$ and $R^9$ are hydrogen; and $R^{10}$ is absent.

In another embodiment of Formula II, $R^6$ is alkyl or fluoro. In yet another embodiment of Formula II, $R^1$, $R^2$ and $R^5$ are independently hydrogen or alkyl.

In another embodiment, $R^1$ and $R^2$ are hydroxyl. In still another embodiment, $R^1$ and $R^2$ are independently hydroxyl or halogen. In another embodiment of Formula II, $R^1$ is alkyl; and $R^2$ and $R^5$ are hydrogen. In another embodiment, of Formula II, $R^2$ is alkyl; and $R^1$ and $R^5$ are hydrogen. In still another embodiment, of Formula II, $R^5$ is alkyl; and $R^1$ and $R^2$ are hydrogen.

In another embodiment of Formula II, $R^3$ is the residue of a naturally occurring amino acid; $R^4$ is hydrogen; Y is O; $R^{10}$ together with $R^9$ form a double bond; $R^8$ is absent; and $R^1$, $R^2$, $R^5$ and $R^6$ are hydrogen.

In another embodiment of Formula II, $R^3$ is the residue of a naturally occurring amino acid; $R^4$ is alkyl; Y is O; $R^{10}$ together with $R^9$ form a double bond; $R^8$ is absent; and $R^1$, $R^2$, $R^5$ and $R^6$ are hydrogen.

In one embodiment of Formula II, the dotted line between C4 and C5 represents a single bond and the dotted line between C5 and C6 represents a single bond.

In another embodiment of Formula II, the dotted line between C4 and C5 represents a single bond and the dotted line between C5 and C6 represents a double bond.

In another embodiment of Formula II, the dotted line between C4 and C5 represents a double bond and the dotted line between C5 and C6 represents a single bond.

In still another embodiment of Formula II, the dotted line between C1 and C2 represents a single bond. In still another embodiment, the dotted line between C1 and C2 represents a double bond.

In another embodiment of Formula II, $OR^3$ is in the alpha configuration. In still another embodiment, $OR^3$ is in the beta configuration.

In one embodiment of Formula II, the dotted lines between C4 and C5 and between C5 and C6 represent a single bond, and the hydrogen at the C5 bridgehead carbon is in the alpha configuration. In another embodiment, the dotted lines between C4 and C5 and between C5 and C6 represent a single bond, and the hydrogen at the C5 bridgehead carbon is in the beta configuration In one embodiment of Formula II, $R^3$ represents a naturally occurring α-amino acid in the L-configuration. In another embodiment, $R^3$ is a residue of L-valine. In other embodiments, $R^3$ represents an amino acid residue with the D-configuration or $R^3$ represents a non-natural amino acid. In other embodiments, $R^3$ represents the residue of a β γ or δ amino acid.

In one preferred embodiment of Formula II, $R^3$ represents an ester of an amino acid. In another embodiment, $R^3$ represents an ester of an amino acid residue where the ester bond is formed with a carboxylate group on the side chain of the amino acid. In certain embodiments of Formula II, a residue of an amino acid is connected to the steroid ring system at the carboxyl group of the amino acid. In other embodiments, a residue of an amino acid is connected to the steroid at the amino acid side chain. For example, amino acids that contain side chains with functional groups that are capable of forming a bond with a hydroxy or a ketone group may be boded to the steroid ring by such a group. In other embodiments, the reactive groups on the amino acid side chains may displace leaving groups formed on the steroid moiety to form a covalent bond. Non-limiting examples of amino acids with reactive groups in the side chain include lysine, cysteine, serine, tyrosine, aspartic acid and arginine.

The amino acid(s) in any of the embodiments of the invention described herein may be naturally occurring or synthetic amino acids and may be in the D or L stereoisomeric form or may exist as a D, L mixture. For example the 20 naturally occurring α-amino acids in the L-configuration are encompassed by the invention as well as α-amino acids in the D-configuration. Synthetic amino acids in either stereoisomeric form are also encompassed.

In one embodiment, a compound of Formula II with the stereochemical configuration of Formula IIa is provided:

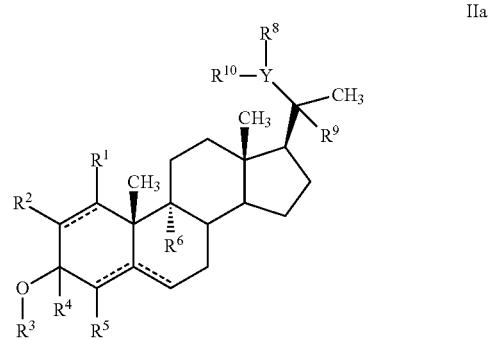

IIa wherein the definition of variables Y, $R^1$, $R^2$, $R^3$, $R^4$, $R^5$, $R^6$, $R^8$, $R^9$ and $R^{10}$ are as defined in Formula II above.

In still another embodiment, a compound of Formula II with the stereochemical configuration of Formula IIb is provided:

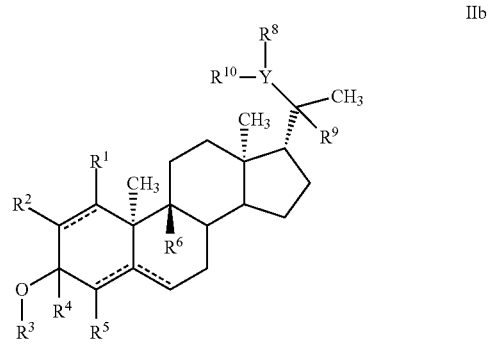

IIb wherein the definition of variables Y, $R^1$, $R^2$, $R^3$, $R^4$, $R^5$, $R^6$, $R^8$, $R^9$ and $R^{10}$ are as defined in Formula II above.

In another embodiment, a progesterone analogue of Formula III is provided:

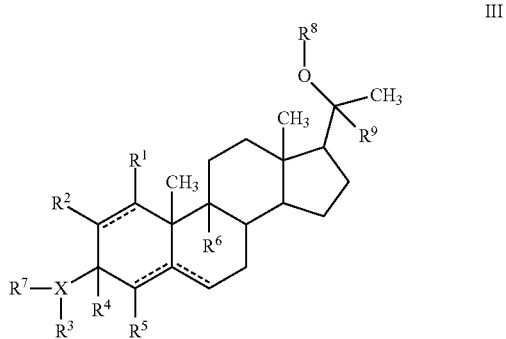

III or a pharmaceutically acceptable salt, ester or prodrug thereof, wherein X is O, N or S;

$R^1$, $R^2$, $R^5$ and $R^6$ are independently hydrogen, alkyl, halogen, hydroxyl cycloalkyl, cycloalkenyl, alkenyl, alkynyl, aryl, alkylaryl, arylalkyl, heterocyclic, heteroaryl, amino, thiol, alkoxy, sulfide, nitro, cyano, azide, sulfonyl, acyl, carboxyl, an ester, an amide, carbamate, carbonate, an amino acid residue or a carbohydrate;

$R^3$ is hydrogen, optionally substituted acyl, a residue of an amino acid, a carbohydrate, monophosphate, diphosphate, triphosphate, —$OR^{11}$, —$NR^{11}R^{12}$; —C(O)R', where R' is alkyl, aryl, aralkyl, $OR^1$, $NR^1R^2$ or the residue of an amino acid; $R^3$ together with X and $R^4$ forms an optionally substituted 5-6 membered heterocyclic or heteroaryl ring containing 1-4 nitrogen, oxygen or sulfur atoms, or $R^3$ is absent;

$R^4$ is hydrogen or alkyl; $R^4$ together with $R^3$ and X forms an optionally substituted 5-6 membered heterocyclic or heteroaryl ring containing 1-4 nitrogen, oxygen or sulfur atoms; or $R^4$ together with $R^7$ form a double bond;

$R^7$ is hydrogen or is absent, or $R^7$ together with $R^4$ forms a double bond;

$R^8$ is hydrogen, optionally substituted acyl, a residue of an amino acid, monophosphate, diphosphate, triphosphate, a carbohydrate; —C(O)R', where R' is alkyl, aryl, aralkyl, $OR^1$, $NR^1R^2$ or the residue of an amino acid; or $R^8$ together with $R^9$ and the oxygen atom forms an optionally substituted 5-6 membered heterocyclic or heteroaryl ring containing 1-4 nitrogen, oxygen or sulfur atoms;

$R^9$ is hydrogen, alkyl, or $R^9$ together with the oxygen atom and $R^8$ forms an optionally substituted 5-6 membered heterocyclic or heteroaryl ring containing 1-4 nitrogen, oxygen or sulfur atoms;

$R^{11}$ is hydrogen, optionally substituted alkyl, hydroxyalkyl, aminoalkyl, the residue of an amino acid, a carbohydrate, optionally substituted acyl, or —C(O)R', where R' is alkyl, aryl, aralkyl, $OR^1$, $NR^1R^2$, or the residue of an amino acid;

$R^{12}$ is hydrogen or alkyl; and the dotted lines indicate the presence of either a single bond or a double bond, wherein the valences of a single bond are completed by hydrogens, provided that if the dotted line between C4 and C5 or between C5 and C6 represents a double bond then the dotted line between C4 and C5 or between C5 and C6 represents a single bond; and with the proviso that neither $XR^3R^7$ nor $R^8$ represent an ester of aspartic acid, glutamic acid, gamma amino butyric acid or α-2-(hydroxyethylamino)-propionic acid.

In one embodiment of Formula III, $R^3$ is hydrogen, optionally substituted acyl, a residue of an amino acid, a carbohydrate, —$OR^{11}$, —$NR^{11}R^{12}$ or $R^3$ is absent; $R^8$ is hydrogen, optionally substituted acyl, a residue of an amino acid, or a carbohydrate; $R^{11}$ is the residue of an amino acid, a carbohydrate or optionally substituted acyl.

In one embodiment, $R^1$, $R^2$, $R^5$ and $R^6$ are independently hydrogen, alkyl, halogen or hydroxyl.

In another embodiment, $R^1$, $R^2$, $R^5$ and $R^6$ are independently methyl, ethyl or propyl.

In still another embodiment, $R^1$, $R^2$, $R^5$ and $R^6$ are independently thiomethyl, hydroxymethyl or cyano.

In another embodiment, $R^1$, $R^2$, $R^5$ and $R^6$ are independently vinyl or ethynyl.

In still another embodiment, $R^1$, $R^2$, $R^5$ and $R^6$ are independently fluoro, bromo, chloro or iodo.

In still another embodiment, $R^4$ and $R^9$ are independently hydrogen or methyl.

In some embodiments, X is O. In other embodiments, X is N. In certain embodiments in which X is O, $R^3$ and $R^4$ come together to form a double bond. In certain embodiments, one of $R^3$ and $R^8$ is a residue of an amino acid. In particular embodiments, the amino acid is a naturally occurring amino acid. In certain embodiments, $R^3$ is a residue of an amino acid. In certain other embodiments, $R^8$ is a residue of an amino acid. In yet further embodiments, both $R^3$ and $R^8$ are residues of an amino acid.

In one embodiment, $R^3$ is a carbohydrate. In another embodiment, $R^8$ is a carbohydrate.

In one embodiment of Formula III, X is O; $R^3$ is the residue of an amino acid or a carbohydrate; and $R^7$ is absent.

In another embodiment of Formula III, X is N; $R^4$ together with $R^7$ form a double bond; $R^3$ is $OR^{11}$; and $R^{11}$ is the residue of an amino acid or a carbohydrate.

In another embodiment of Formula III, X is N; $R^4$ together with $R^7$ form a double bond; $R^3$ is —$NR^{11}R^{12}$; $R^{11}$ is the residue of an amino acid or a carbohydrate; and $R^{12}$ is hydrogen.

In another embodiment of Formula III, $R^8$ is the residue of a naturally occurring amino acid; $R^9$ is hydrogen; X is O; $R^4$ together with $R^7$ form a double bond; and $R^3$ is absent.

In another embodiment of Formula III, $R^8$ is a carbohydrate; $R^9$ is hydrogen; X is O; $R^4$ together with $R^7$ form a double bond; and $R^3$ is absent.

In another embodiment of Formula III, $R^8$ is the residue of a naturally occurring amino acid or a carbohydrate; $R^9$ is hydrogen; X is O; $R^3$ and $R^4$ are hydrogen; and $R^7$ is absent.

In another embodiment of Formula III, $R^6$ is alkyl or fluoro. In yet another embodiment of Formula III, $R^1$, $R^2$ and $R^5$ are independently hydrogen or alkyl. In another embodiment, $R^1$ and $R^2$ are hydroxyl. In still another embodiment, $R^1$ and $R^2$ are independently hydroxyl or halogen. In another embodiment of Formula III, $R^1$ is alkyl; and $R^2$ and $R^5$ are hydrogen. In another embodiment, of Formula III, $R^2$ is alkyl; and $R^1$ and $R^5$ are hydrogen. In still another embodiment, of Formula III, $R^5$ is alkyl; and $R^1$ and $R^2$ are hydrogen.

In another embodiment of Formula III, $R^8$ is the residue of a naturally occurring amino acid; $R^9$ is hydrogen; X is O; $R^4$ together with $R^7$ form a double bond; $R^3$ is absent; and $R^1$, $R^2$, $R^5$ and $R^6$ are hydrogen.

In another embodiment of Formula III, $R^8$ is the residue of a naturally occurring amino acid; $R^9$ is alkyl; X is O; $R^4$ together with $R^7$ form a double bond; $R^3$ is absent; and $R^1$, $R^2$, $R^5$ and $R^6$ are hydrogen.

In one embodiment of Formula III, the dotted line between C4 and C5 represents a single bond and the dotted line between C5 and C6 represents a single bond.

In another embodiment of Formula III, the dotted line between C4 and C5 represents a single bond and the dotted line between C5 and C6 represents a double bond.

In another embodiment of Formula III, the dotted line between C4 and C5 represents a double bond and the dotted line between C5 and C6 represents a single bond.

In still another embodiment of Formula III, the dotted line between C1 and C2 represents a single bond. In still another embodiment, the dotted line between C1 and C2 represents a double bond.

In another embodiment of Formula III, —$XR^3R^7$ is in the alpha configuration. In still another embodiment, —$XR^3R^7$ is in the beta configuration.

In one embodiment of Formula III, the dotted lines between C4 and C5 and between C5 and C6 represent a single bond, and the hydrogen at the C5 bridgehead carbon is in the alpha configuration. In another embodiment, the dotted lines between C4 and C5 and between C5 and C6 represent a single bond, and the hydrogen at the C5 bridgehead carbon is in the beta configuration In one embodiment of Formula III, $R^8$ represents a naturally occurring α-amino acid in the L-configuration. In another embodiment, $R^8$ is a residue of L-valine. In another embodiment, $R^8$ represents an amino acid residue with the D-configuration. In another embodiment, $R^8$ represents a non-natural amino acid. In other embodiments, $R^8$ represents the residue of a β γ or δ amino acid.

In one preferred embodiment of Formula III, $R^8$ represents an ester of an amino acid. In another embodiment, $R^8$ represents an ester of an amino acid residue where the ester bond is formed with a carboxylate group on the side chain of the amino acid.

In one preferred embodiment of Formula III, $R^3$ represents an ester of an amino acid. In another embodiment, $R^3$ represents an ester of an amino acid residue where the ester bond is formed with a carboxylate group on the side chain of the amino acid. In certain embodiments of Formula III, a residue of an amino acid is connected to the steroid ring system at the carboxyl group of the amino acid. In other embodiments, a residue of an amino acid is connected to the steroid at the amino acid side chain. For example, amino acids that contain side chains with functional groups that are capable of forming a bond with a hydroxy or a ketone group may be boded to the steroid ring by such a group. In other embodiments, the reactive groups on the amino acid side chains may displace leaving groups formed on the steroid moiety to form a covalent bond. Non-limiting examples of amino acids with reactive groups in the side chain include lysine, cysteine, serine, tyrosine, aspartic acid, arginine and the like.

The amino acid(s) in any of the embodiments of the invention described herein may be naturally occurring or synthetic amino acids and may be in the D or L stereoisomeric form or may exist as a D, L mixture. For example the 20 naturally occurring α-amino acids in the L-configuration are encompassed by the invention as well as α-amino acids in the D-configuration. Synthetic amino acids in either stereoisomeric form are also encompassed.

In one embodiment, a compound of Formula III with the stereochemical configuration of Formula IIIa is provided:

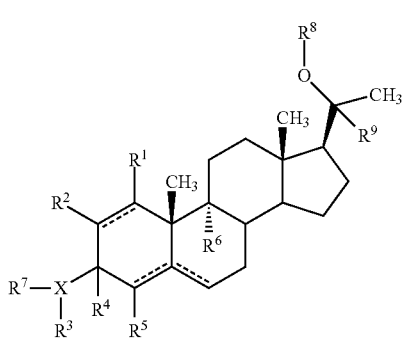

IIIa wherein the definition of variables X, $R^1$, $R^2$, $R^3$, $R^4$, $R^5$, $R^6$, $R^7$, $R^8$, and $R^9$ are as defined in Formula III above.

In yet another embodiment, a compound of Formula III with the stereochemical configuration of Formula IIIb is provided:

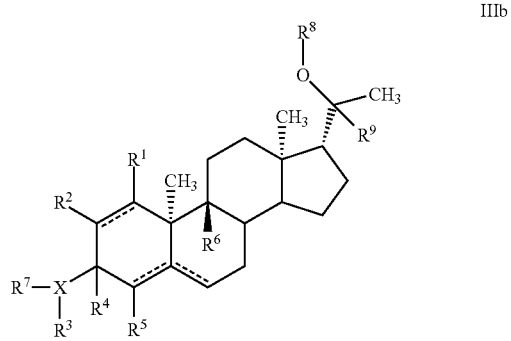

IIIb wherein the definition of variables X, $R^1$, $R^2$, $R^3$, $R^4$, $R^5$, $R^6$, $R^7$, $R^8$, and $R^9$ are as defined in Formula III above.

In another embodiment a compound of Formula IV is provided:

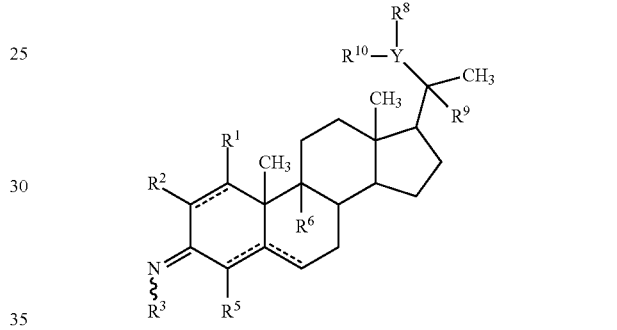

IV or a pharmaceutically acceptable salt, ester or prodrug thereof, wherein Y is O, N or S;

$R^1$, $R^2$, $R^5$ and $R^6$ are independently hydrogen, alkyl, halogen, hydroxyl cycloalkyl, cycloalkenyl, alkenyl, alkynyl, aryl, alkylaryl, arylalkyl, heterocyclic, heteroaryl, amino, thiol, alkoxy, sulfide, nitro, cyano, azide, sulfonyl, acyl, carboxyl, an ester, an amide, carbamate, carbonate, an amino acid residue or a carbohydrate;

$R^3$ is an —$OR^{11}$, —$NR^{11}R^{12}$, monophosphate, diphosphate, triphosphate, a carbohydrate, or —C(O)R', where R' is alkyl, aryl, aralkyl, $OR^1$, $NR^1R^2$ or the residue of an amino acid;

$R^8$ is hydrogen, optionally substituted acyl, a residue of an amino acid, a carbohydrate, —$OR^{11}$, —$NR^{11}R^{12}$, monophosphate, diphosphate, triphosphate, —C(O)R', where R' is alkyl, aryl, aralkyl, $OR^1$, $NR^1R^2$ or the residue of an amino acid; or $R^8$ together with $R^9$ and Y forms an optionally substituted 5-6 membered heterocyclic or heteroaryl ring containing 1-4 nitrogen, oxygen or sulfur atoms, or $R^8$ is absent;

$R^9$ is hydrogen or alkyl; $R^9$ together with Y and $R^8$ forms an optionally substituted 5-6 membered heterocyclic or heteroaryl ring containing 1-4 nitrogen, oxygen or sulfur atoms, or $R^9$ and $R^{10}$ together form a double bond;

$R^{10}$ is hydrogen or absent, or $R^{10}$ together with $R^9$ form a double bond;

$R^{11}$ is hydrogen, optionally substituted alkyl, hydroxyalkyl, aminoalkyl, the residue of an amino acid, a carbohydrate monophosphate, diphosphate, triphosphate; —C(O)R', where R' is alkyl, aryl, aralkyl, $OR^1$, $NR^1R^2$ or the residue of an amino acid; or an optionally substituted ester;

$R^{12}$ is hydrogen or alkyl; and the dotted lines indicate the presence of either a single bond or a double bond, wherein the valences of a single bond are completed by hydrogens, provided that if the dotted line between C4 and C5 or between C5 and C6 represents a double bond then the other dotted line between C4 and C5 or between C5 and C6 represents a single bond; and with the proviso that $YR^8R^{10}$ does not represent an ester of aspartic acid, glutamic acid, gamma amino butyric acid or α-2-(hydroxyethylamino)-propionic acid; and with the proviso that when Y is N, $R^8$ does not represent aspartic acid, glutamic acid, gamma amino butyric acid or α-2-(hydroxyethylamino)-propionic acid.

In one embodiment of Formula IV, $R^3$ is an $-OR^{11}$, $-NR^{11}R^{12}$, or a carbohydrate; $R^8$ is hydrogen, optionally substituted acyl, a residue of an amino acid, a carbohydrate, $-OR^{11}$, $-NR^{11}R^{12}$, or $R^8$ is absent; $R^{11}$ is the residue of an amino acid, a carbohydrate or an optionally substituted ester;

In one embodiment, $R^1$, $R^2$, $R^5$ and $R^6$ are independently hydrogen, alkyl, halogen or hydroxyl.

In another embodiment, $R^1$, $R^2$, $R^5$ and $R^6$ are independently methyl, ethyl or propyl.

In still another embodiment, $R^1$, $R^2$, $R^5$ and $R^6$ are independently thiomethyl, hydroxymethyl or cyano.

In another embodiment, $R^1$, $R^2$, $R^5$ and $R^6$ are independently vinyl or ethynyl.

In still another embodiment, $R^1$, $R^2$, $R^5$ and $R^6$ are independently fluoro, bromo, chloro or iodo.

In still another embodiment, $R^9$ is hydrogen or methyl.

In some embodiments, Y is O. In other embodiments, Y is N. In certain embodiments in which Y is O, and $R^8$ and $R^{10}$ come together to form a double bond. In certain other embodiments, one of $R^3$ and $R^8$ is a residue of an amino acid. In particular embodiments, the amino acid is a naturally occurring amino acid. In certain embodiments, $R^3$ is a residue of an amino acid. In certain other embodiments, $R^8$ is a residue of an amino acid. In yet further embodiments, both $R^3$ and $R^8$ are residues of an amino acid.

In other embodiments, $R^3$ is a carbohydrate. In another embodiment, $R^8$ is a carbohydrate.

In one embodiment of Formula IV, Y is O; $R^8$ is the residue of an amino acid; and $R^{10}$ is absent.

In another embodiment of Formula IV, Y is N; $R^{10}$ together with $R^9$ form a double bond; $R^8$ is $OR^{11}$; and $R^{11}$ is the residue of an amino acid or a carbohydrate.

In another embodiment of Formula IV, Y is N; $R^{10}$ together with $R^9$ form a double bond; $R^8$ is $-NR^{11}R^{12}$; $R^{11}$ is the residue of an amino acid or a carbohydrate; and $R^{12}$ is hydrogen.

In another embodiment of Formula IV, $R^3$ is $-OR^{11}$ and $R^{11}$ is the residue of a naturally occurring amino acid or a carbohydrate; Y is O; $R^{10}$ together with $R^9$ form a double bond; and $R^8$ is absent.

In another embodiment of Formula IV, $R^3$ is $-NR^{11}R^{12}$; $R^{11}$ is the residue of a naturally occurring amino acid; $R^{11}$ is hydrogen; Y is O; $R^{10}$ together with $R^9$ form a double bond; and $R^8$ is absent.

In another embodiment of Formula IV, $R^3$ is a carbohydrate; Y is O; $R^{10}$ together with $R^9$ form a double bond; and $R^8$ is absent.

In another embodiment of Formula IV, $R^3$ is $-OR^{11}$ and $R^{11}$ is the residue of a naturally occurring amino acid or a carbohydrate; Y is O; $R^8$ and $R^9$ are hydrogen; and $R^{10}$ is absent.

In another embodiment of Formula IV, $R^3$ is $-NR^{11}R^{12}$; $R^{11}$ is the residue of a naturally occurring amino acid; $R^{12}$ is hydrogen; Y is O; $R^8$ and $R^9$ are hydrogen; and $R^{10}$ is absent.

In another embodiment of Formula IV, $R^6$ is alkyl or fluoro. In yet another embodiment of Formula IV, $R^1$, $R^2$ and $R^5$ are independently hydrogen or alkyl. In another embodiment, $R^1$ and $R^2$ are hydroxyl. In still another embodiment, $R^1$ and $R^2$ are independently hydroxyl or halogen. In another embodiment of Formula IV, $R^1$ is alkyl; and $R^2$ and $R^5$ are hydrogen. In another embodiment, of Formula IV, $R^2$ is alkyl; and $R^1$ and $R^5$ are hydrogen. In still another embodiment, of Formula IV, $R^5$ is alkyl; and $R^1$ and $R^2$ are hydrogen.

In another embodiment of Formula IV, $R^3$ is $-OR^{11}$ and $R^{11}$ is the residue of a naturally occurring amino acid; Y is O; $R^{10}$ together with $R^9$ form a double bond; $R^8$ is absent; and $R^1$, $R^2$, $R^5$ and $R^6$ are hydrogen.

In another embodiment of Formula IV, $R^3$ is $-NR^{11}R^{12}$; $R^{11}$ is the residue of a naturally occurring amino acid; $R^{12}$ is hydrogen; Y is O; $R^{10}$ together with $R^9$ form a double bond; $R^8$ is absent; and $R^1$, $R^2$, $R^5$ and $R^6$ are hydrogen.

In one embodiment of Formula IV, the dotted line between C4 and C5 is a single bond and the dotted line between C5 and C6 is a single bond.

In another embodiment of Formula IV, the dotted line between C4 and C5 is a single bond and the dotted line between C5 and C6 is a double bond.

In another embodiment of Formula IV, the dotted line between C4 and C5 is a double bond and the dotted line between C5 and C6 is a single bond.

In still another embodiment of Formula IV, the dotted line between C1 and C2 represents a single bond. In still another embodiment, the dotted line between C1 and C2 represents a double bond.

In one embodiment of Formula IV, the dotted lines between C4 and C5 and between C5 and C6 represent a single bond, and the hydrogen at the C5 bridgehead carbon is in the alpha configuration. In another embodiment, the dotted lines between C4 and C5 and between C5 and C6 represent a single bond, and the hydrogen at the C5 bridgehead carbon is in the beta configuration In one embodiment of Formula IV, $R^3$ comprises a residue of a naturally occurring α-amino acid in the L-configuration. In another embodiment, $R^3$ comprises a residue of L-valine. In another embodiment, $R^3$ comprises an amino acid residue with the D-configuration. In another embodiment, $R^3$ comprises a non-natural amino acid. In other embodiments, $R^3$ comprises the residue of a β γ or δ amino acid.

In one preferred embodiment of Formula IV, $R^3$ represents an ester of an amino acid. In another embodiment, $R^3$ represents an ester of an amino acid residue where the ester bond is formed with a carboxylate group on the side chain of the amino acid. In certain embodiments of Formula IV, a residue of an amino acid is connected to the steroid ring system at the carboxyl group of the amino acid. In other embodiments, a residue of an amino acid is connected to the steroid at the amino acid side chain. For example, amino acids that contain side chains with functional groups that are capable of forming a bond with a hydroxy or a ketone group may be boded to the steroid ring by such a group. In other embodiments, the reactive groups on the amino acid side chains may displace leaving groups formed on the steroid moiety to form a covalent bond. Non-limiting examples of amino acids with reactive groups in the side chain include lysine, cysteine, serine, tyrosine, aspartic acid, arginine and the like.

The amino acid(s) in any of the embodiments of the invention described herein may be naturally occurring or synthetic amino acids and may be in the D or L stereoisomeric form or may exist as a D, L mixture. For example the 20 naturally occurring α-amino acids in the L-configuration are encompassed by the invention as well as α-amino acids in the D-configuration. Synthetic amino acids in either stereoisomeric form are also encompassed.

In one embodiment, a compound of Formula IV with the stereochemical configuration of Formula IVa is provided:

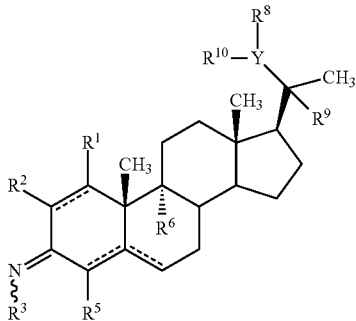

IVa wherein the definition of variables Y, $R^1$, $R^2$, $R^3$, $R^5$, $R^6$, $R^8$, $R^9$ and $R^{10}$ are as defined in Formula IV above.

In another embodiment, a compound of Formula IV with the stereochemical configuration of Formula IVb is provided:

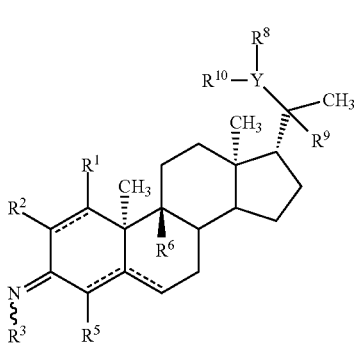

IVb wherein the definition of variables Y, $R^1$, $R^2$, $R^3$, $R^5$, $R^6$, $R^8$, $R^9$ and $R^{10}$ are as defined in Formula IV above.

In another embodiment, a progesterone or steroid analogue of Formula V is provided:

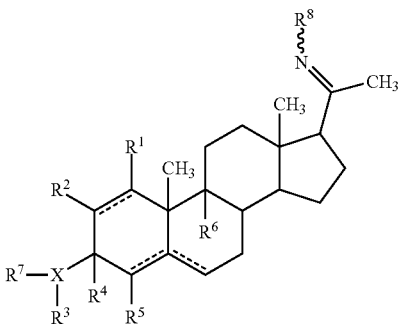

V or a pharmaceutically acceptable salt, ester or prodrug thereof,
wherein X is O, N or S;
$R^1$, $R^2$, $R^5$ and $R^6$ are independently hydrogen, alkyl, halogen, hydroxyl cycloalkyl, cycloalkenyl, alkenyl, alkynyl, aryl, alkylaryl, arylalkyl, heterocyclic, heteroaryl, amino, thiol, alkoxy, sulfide, nitro, cyano, azide, sulfonyl, acyl, carboxyl, an ester, an amide, carbamate, carbonate, an amino acid residue or a carbohydrate;

$R^3$ is hydrogen, optionally substituted acyl, a residue of an amino acid a carbohydrate; —$OR^{11}$; —$NR^{11}R^{12}$, monophosphate, diphosphate, triphosphate; —C(O)R', where R' is alkyl, aryl, aralkyl, $OR^1$, $NR^1R^2$ or the residue of an amino acid; $R^3$ together with X and $R^4$ forms an optionally substituted 5-6 membered heterocyclic or heteroaryl ring containing 1-4 nitrogen, oxygen or sulfur atoms, or $R^3$ is absent;

$R^4$ is hydrogen or alkyl; $R^4$ together with $R^3$ and X forms an optionally substituted 5-6 membered heterocyclic or heteroaryl ring containing 1-4 nitrogen, oxygen or sulfur atoms, or $R^4$ together with $R^7$ form a double bond;

$R^8$ is —$OR^{11}$, —$NR^{11}R^{12}$, monophosphate, diphosphate, triphosphate, a carbohydrate, —C(O)R', where R' is alkyl, aryl, aralkyl, $OR^1$, $NR^1R^2$ or the residue of an amino acid;

$R^{11}$ is hydrogen, optionally substituted alkyl, hydroxyalkyl, aminoalkyl, the residue of an amino acid, a carbohydrate, monophosphate, diphosphate, triphosphate; —C(O)R', where R' is alkyl, aryl, aralkyl, $OR^1$, $NR^1R^2$, or the residue of an amino acid; or an optionally substituted ester;

$R^{12}$ is hydrogen or alkyl; and the dotted lines indicate the presence of either a single bond or a double bond, wherein the valences of a single bond are completed by hydrogens, provided that if the dotted line between C4 and C5 or between C5 and C6 represents a double bond then the other dotted line between C4 and C5 or between C5 and C6 represents a single bond; and with the proviso that $XR^3R^7$ does not represent an ester of aspartic acid, glutamic acid, gamma amino butyric acid or α-2-(hydroxyethylamino)-propionic acid; and with the proviso that $R^8$ does not represent aspartic acid, glutamic acid, gamma amino butyric acid or α-2-(hydroxyethylamino)-propionic acid.

In one embodiment of Formula V, $R^3$ is hydrogen, optionally substituted acyl, a residue of an amino acid a carbohydrate; —$OR^{11}$; —$NR^{11}R^{12}$, or $R^3$ is absent; $R^8$ is —$OR^{11}$, —$NR^{11}R^{12}$ or a carbohydrate; $R^{11}$ is the residue of an amino acid, a carbohydrate or an optionally substituted ester.

In one embodiment, $R^1$, $R^2$, $R^5$ and $R^6$ are independently hydrogen, alkyl, halogen or hydroxyl.

In another embodiment, $R^1$, $R^2$, $R^5$ and $R^6$ are independently methyl, ethyl or propyl.

In still another embodiment, $R^1$, $R^2$, $R^5$ and $R^6$ are independently thiomethyl, hydroxymethyl or cyano.

In another embodiment, $R^1$, $R^2$, $R^5$ and $R^6$ are independently vinyl or ethynyl.

In still another embodiment, $R^1$, $R^2$, $R^5$ and $R^6$ are independently fluoro, bromo, chloro or iodo.

In still another embodiment, $R^4$ is hydrogen or methyl.

In some embodiments, X is O. In other embodiments, X is N. In certain embodiments in which X is O, $R^3$ and $R^4$ come together to form a double bond. In certain embodiments, one of $R^3$ and $R^8$ is a residue of an amino acid. In particular embodiments, the amino acid is a naturally occurring amino acid. In certain embodiments, $R^3$ is a residue of an amino acid. In certain other embodiments, $R^8$ is a residue of an amino acid. In yet further embodiments, both $R^3$ and $R^8$ are residues of an amino acid.

In other embodiments, $R^3$ is a carbohydrate. In another embodiment, $R^8$ is a carbohydrate.

In one embodiment of Formula V, X is O; $R^3$ is the residue of an amino acid or a carbohydrate; and $R^7$ is absent.

In another embodiment of Formula V, X is N; $R^4$ together with $R^7$ form a double bond; $R^3$ is $OR^{11}$; and $R^{11}$ is the residue of an amino acid or a carbohydrate.

In another embodiment of Formula V, X is N; $R^4$ together with $R^7$ form a double bond; $R^3$ is —$NR^{11}R^{12}$; $R^{11}$ is the residue of an amino acid or a carbohydrate; and $R^{12}$ is hydrogen.

In another embodiment of Formula V, $R^8$ is —$OR^{11}$; $R^{11}$ is the residue of a naturally occurring amino acid or a carbohydrate; X is O; $R^4$ together with $R^7$ form a double bond; and $R^3$ is absent.

In another embodiment of Formula V, $R^8$ is —$NR^{11}R^{12}$; $R^{11}$ is the residue of a naturally occurring amino acid; $R^{12}$ is hydrogen; X is O; $R^4$ together with $R^7$ form a double bond; and $R^3$ is absent.

In another embodiment of Formula V, $R^8$ is —$OR^{11}$; $R^{11}$ is a carbohydrate; X is O; $R^4$ together with $R^7$ form a double bond; and $R^3$ is absent.

In another embodiment of Formula V, $R^8$ is —$OR^{11}$; $R^{11}$ is the residue of a naturally occurring amino acid or a carbohydrate; X is O; $R^3$ and $R^4$ are hydrogen; and $R^7$ is absent.

In another embodiment of Formula V, $R^8$ is —$NR^{11}R^{12}$; $R^{11}$ is the residue of a naturally occurring amino acid or a carbohydrate; $R^{12}$ is hydrogen; X is O; $R^3$ and $R^4$ are hydrogen; and $R^7$ is absent.

In another embodiment of Formula V, $R^6$ is alkyl or fluoro. In yet another embodiment of Formula V, $R^1$, $R^2$ and $R^5$ are independently hydrogen or alkyl. In another embodiment, $R^1$ and $R^2$ are hydroxyl. In still another embodiment, $R^1$ and $R^2$ are independently hydroxyl or halogen. In another embodiment of Formula V, $R^1$ is alkyl; and $R^2$ and $R^5$ are hydrogen. In another embodiment, of Formula V, $R^2$ is alkyl; and $R^1$ and $R^5$ are hydrogen. In still another embodiment, of Formula V, $R^5$ is alkyl; and $R^1$ and $R^2$ are hydrogen.

In another embodiment of Formula V, $R^8$ is —$OR^{11}$; $R^{11}$ is the residue of a naturally occurring amino acid; X is O; $R^4$ together with $R^7$ form a double bond; $R^3$ is absent; and $R^1$, $R^2$, $R^5$ and $R^6$ are hydrogen.

In another embodiment of Formula V, $R^8$ is —$NR^{11}R^{12}$; $R^{11}$ is the residue of a naturally occurring amino acid; $R^{12}$ is hydrogen; X is O; $R^4$ together with $R^7$ form a double bond; $R^3$ is absent; and $R^1$, $R^2$, $R^5$ and $R^6$ are hydrogen.

In another embodiment of Formula V, $R^8$ is —$OR^{11}$; $R^{11}$ is the residue of a naturally occurring amino acid; X is O; $R^3$ and $R^4$ are hydrogen; $R^7$ is absent; and $R^1$, $R^2$, $R^5$ and $R^6$ are hydrogen.

In another embodiment of Formula V, $R^8$ is —$NR^{11}R^{12}$; $R^{11}$ is the residue of a naturally occurring amino acid; $R^{12}$ is hydrogen; X is O; $R^3$ and $R^4$ are hydrogen; $R^7$ is absent; and $R^1$, $R^2$, $R^5$ and $R^6$ are hydrogen; and $R^1$, $R^2$, $R^5$ and $R^6$ are hydrogen.

In one embodiment of Formula V, the dotted line between C4 and C5 is a single bond and the dotted line between C5 and C6 is a single bond.

In another embodiment of Formula V, the dotted line between C4 and C5 is a single bond and the dotted line between C5 and C6 is a double bond.

In another embodiment of Formula V, the dotted line between C4 and C5 is a double bond and the dotted line between C5 and C6 is a single bond.

In still another embodiment of Formula V, the dotted line between C1 and C2 represents a single bond. In still another embodiment, the dotted line between C1 and C2 represents a double bond.

In another embodiment of Formula V, —$XR^3R^7$ is in the alpha configuration. In still another embodiment, —$XR^3R^7$ is in the beta configuration.

In one embodiment of Formula V, the dotted lines between C4 and C5 and between C5 and C6 represent a single bond, the hydrogen at the C5 bridgehead carbon is in the alpha configuration. In another embodiment, the dotted lines between C4 and C5 and between C5 and C6 represent a single bond, the hydrogen at the C5 bridgehead carbon is in the beta configuration In one embodiment of Formula V, $R^8$ comprises a naturally occurring α-amino acid in the L-configuration. In another embodiment, $R^8$ comprises a residue of L-valine. In another embodiment, $R^8$ comprises an amino acid residue with the D-configuration. In another embodiment, $R^8$ comprises a non-natural amino acid. In other embodiments, $R^8$ comprises the residue of a β γ or δ amino acid.

In one preferred embodiment of Formula V, $R^3$ represents an ester of an amino acid. In another embodiment, $R^3$ represents an ester of an amino acid residue where the ester bond is formed with a carboxylate group on the side chain of the amino acid. In certain embodiments of Formula V, a residue of an amino acid is connected to the steroid ring system at the carboxyl group of the amino acid. In other embodiments, a residue of an amino acid is connected to the steroid at the amino acid side chain. For example, amino acids that contain side chains with functional groups that are capable of forming a bond with a hydroxy or a ketone group may be boded to the steroid ring by such a group. In other embodiments, the reactive groups on the amino acid side chains may displace leaving groups formed on the steroid moiety to form a covalent bond. Non-limiting examples of amino acids with reactive groups in the side chain include lysine, cysteine, serine, tyrosine, aspartic acid, arginine and the like.

The amino acid(s) in any of the embodiments of the invention described herein may be naturally occurring or synthetic amino acids and may be in the D or L stereoisomeric form or may exist as a D, L mixture. For example the 20 naturally occurring α-amino acids in the L-configuration are encompassed by the invention as well as α-amino acids in the D-configuration. Synthetic amino acids in either stereoisomeric form are also encompassed.

In one embodiment, a compound of Formula V with the stereochemical configuration of Formula Va is provided:

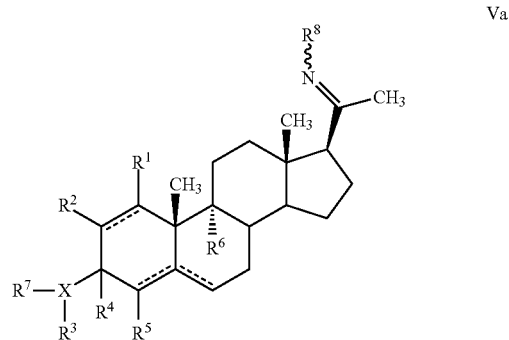

wherein the definition of variables X, $R^1$, $R^2$, $R^3$, $R^4$, $R^5$, $R^6$, $R^7$, and $R^8$ are as defined in Formula V above.

In another embodiment, a compound of Formula V with the stereochemical configuration of Formula Vb is provided:

Vb wherein the definition of variables X, $R^1$, $R^2$, $R^3$, $R^4$, $R^5$, $R^6$, $R^7$, and $R^8$ are as defined in Formula V above.

In another embodiment of the invention, a progesterone analogue of Formula VI is provided:

VI or a pharmaceutically acceptable salt, ester or prodrug thereof, wherein $R^1$, $R^2$, $R^5$ and $R^6$ are independently hydrogen, alkyl, halogen, hydroxyl cycloalkyl, cycloalkenyl, alkenyl, alkynyl, aryl, alkylaryl, arylalkyl, heterocyclic, heteroaryl, amino, thiol, alkoxy, sulfide, nitro, cyano, azide, sulfonyl, acyl, carboxyl, an ester, an amide, carbamate, carbonate, an amino acid residue or a carbohydrate;

$R^3$ is hydrogen, optionally substituted acyl, a residue of an amino acid, a carbohydrate, monophosphate, diphosphate, triphosphate; —C(O)R', where R' is alkyl, aryl, aralkyl, $OR^1$, $NR^1R^2$ or the residue of an amino acid; or $R^3$ together with the oxygen and $R^4$ forms an optionally substituted 5-6 membered heterocyclic or heteroaryl ring containing 1-4 nitrogen, oxygen or sulfur atoms;

$R^4$ is hydrogen, alkyl or $R^4$ together with $R^3$ and the oxygen forms an optionally substituted 5-6 membered heterocyclic or heteroaryl ring containing 1-4 nitrogen, oxygen or sulfur atoms; and the dotted lines indicate the presence of either a single bond or a double bond, wherein the valences of a single bond are completed by hydrogens, provided that if the dotted line between C4 and C5 or between C5 and C6 represents a double bond then the other dotted line between C4 and C5 or between C5 and C6 represents a single bond; and with the proviso that neither $R^3$ does not represent an ester of aspartic acid, glutamic acid, gamma amino butyric acid or α-2-(hydroxyethylamino)-propionic acid.

In one embodiment of Formula VI, $R^3$ is hydrogen, optionally substituted acyl, a residue of an amino acid or a carbohydrate.

In another embodiment of Formula VI, $R^6$ is alkyl or fluoro. In yet another embodiment of Formula VI, $R^1$, $R^2$ and $R^5$ are independently hydrogen or alkyl. In another embodiment, $R^1$ and $R^2$ are hydroxyl. In still another embodiment, $R^1$ and $R^2$ are independently hydroxyl or halogen. In another embodiment of Formula VI, $R^1$ is alkyl; and $R^2$ and $R^5$ are hydrogen. In another embodiment, of Formula VI, $R^2$ is alkyl; and $R^1$ and $R^5$ are hydrogen. In still another embodiment, of Formula VI, $R^5$ is alkyl; and $R^1$ and $R^2$ are hydrogen.

In one embodiment, $R^1$, $R^2$, $R^5$ and $R^6$ are independently hydrogen, alkyl, halogen or hydroxyl.

In another embodiment, $R^1$, $R^2$, $R^5$ and $R^6$ are independently methyl, ethyl or propyl.

In still another embodiment, $R^1$, $R^2$, $R^5$ and $R^6$ are independently thiomethyl, hydroxymethyl or cyano.

In another embodiment, $R^1$, $R^2$, $R^5$ and $R^6$ are independently vinyl or ethynyl.

In still another embodiment, $R^1$, $R^2$, $R^5$ and $R^6$ are independently fluoro, bromo, chloro or iodo.

In still another embodiment, $R^4$ is hydrogen or methyl.

In another embodiment of Formula VI, $R^3$ is the residue of a naturally occurring amino acid; and $R^1$, $R^2$, $R^4$, $R^5$ and $R^6$ are hydrogen.

In another embodiment of Formula VI, $R^3$ is the residue of a naturally occurring amino acid or a carbohydrate; $R^4$ is alkyl; and $R^1$, $R^2$, $R^5$ and $R^6$ are hydrogen.

In one embodiment of Formula VI, $R^1$ is alkyl; and $R^2$, $R^4$ and $R^5$ are hydrogen.

In another embodiment of Formula VI, $R^1$ and $R^4$ are alkyl; and $R^2$ and $R^5$ are hydrogen.

In another embodiment of Formula VI, $R^3$ is a carbohydrate; and $R^1$, $R^2$, $R^4$, $R^5$ and $R^6$ are hydrogen.

In another embodiment of Formula VI, $R^3$ is —C(O)R', where R' is alkyl, aryl, aralkyl, or the residue of an amino acid; and $R^1$, $R^2$, $R^4$, $R^5$ and $R^6$ are hydrogen.

In one embodiment of Formula VI, the dotted line between C4 and C5 represents a single bond and the dotted line between C5 and C6 represents a single bond.

In another embodiment of Formula VI, the dotted line between C4 and C5 represents a single bond and the dotted line between C5 and C6 represents a double bond.

In another embodiment of Formula VI, the dotted line between C4 and C5 represents a double bond and the dotted line between C5 and C6 represents a single bond.

In still another embodiment of Formula VI, the dotted line between C1 and C2 represents a single bond. In still another embodiment, the dotted line between C1 and C2 represents a double bond.

In another embodiment of Formula VI, $OR^3$ is in the alpha configuration. In still another embodiment, $OR^3$ is in the beta configuration.

In one embodiment of Formula VI, the dotted lines between C4 and C5 and between C5 and C6 represent a single bond, and the hydrogen at the C5 bridgehead carbon is in the alpha configuration. In another embodiment, the dotted lines between C4 and C5 and between C5 and C6 represent a single bond, and the hydrogen at the C5 bridgehead carbon is in the beta configuration.

In one embodiment of Formula VI, $R^3$ represents a naturally occurring α-amino acid in the L-configuration. In another embodiment, $R^3$ is a residue of L-valine. In another embodiment, $R^3$ represents an amino acid residue with the D-configuration. In another embodiment, $R^3$ represents a non-natural amino acid. In other embodiments, $R^3$ represents the residue of a β γ or δ amino acid.

In one preferred embodiment of Formula VI, $R^3$ represents an ester of an amino acid. In another embodiment, $R^3$ represents an ester of an amino acid residue where the ester bond is formed with a carboxylate group on the side chain of the amino acid. In certain embodiments of Formula VI, a residue of an amino acid is connected to the steroid ring system at the carboxyl group of the amino acid. In other embodiments, a residue of an amino acid is connected to the steroid at the amino acid side chain. For example, amino acids that contain side chains with functional groups that are capable of forming a bond with a hydroxy or a ketone group may be bonded to the steroid ring by such a group. In other embodiments, the reactive groups on the amino acid side chains may displace leaving groups formed on the steroid moiety to form a covalent bond. Non-limiting examples of amino acids with reactive groups in the side chain include lysine, cysteine, serine, tyrosine, aspartic acid, arginine and the like.

The amino acid(s) in any of the embodiments of the invention described herein may be naturally occurring or synthetic amino acids and may be in the D or L stereoisomeric form or may exist as a D, L mixture. For example the 20 naturally occurring α-amino acids in the L-configuration are encompassed by the invention as well as α-amino acids in the D-configuration. Synthetic amino acids in either stereoisomeric form are also encompassed.

In one embodiment, a compound of Formula VI with the stereochemical configuration of Formula VIa is provided:

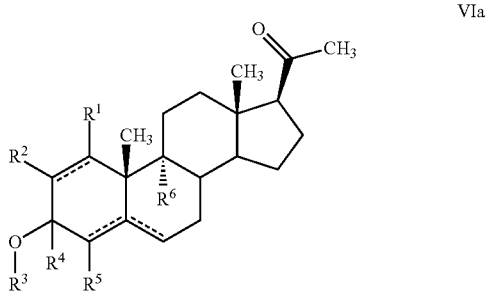

VIa wherein the definition of variables $R^1$, $R^2$, $R^3$, $R^4$, $R^5$, and $R^6$ are as defined in Formula VI above.

In another embodiment, a compound of Formula VI with the stereochemical configuration of Formula VIb is provided:

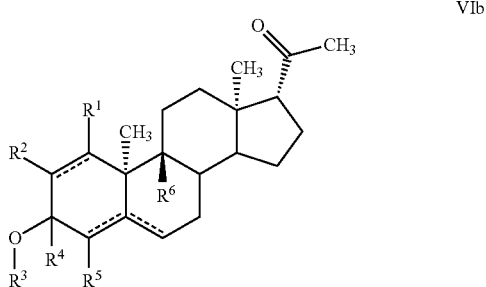

VIb wherein the definition of variables $R^1$, $R^2$, $R^3$, $R^4$, $R^5$, and $R^6$ are as defined in Formula VI above.

In still another embodiment, a progesterone analogue of Formula VII is provided:

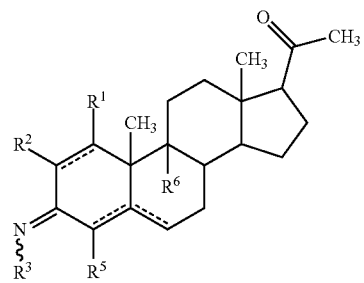

VII or a pharmaceutically acceptable salt, ester or prodrug thereof, wherein, $R^1$, $R^2$, $R^5$ and $R^6$ are independently hydrogen, alkyl, halogen, hydroxyl cycloalkyl, cycloalkenyl, alkenyl, alkynyl, aryl, alkylaryl, arylalkyl, heterocyclic, heteroaryl, amino, thiol, alkoxy, sulfide, nitro, cyano, azide, sulfonyl, acyl, carboxyl, an ester, an amide, carbamate, carbonate, an amino acid residue or a carbohydrate;

$R^3$ is —$OR^{11}$, —$NR^{11}R^{12}$, monophosphate, diphosphate, triphosphate, a carbohydrate, or —C(O)R', where R' is alkyl, aryl, aralkyl, $OR^1$, $NR^1R^2$ or the residue of an amino acid;

$R^{11}$ is hydrogen, optionally substituted alkyl, hydroxyalkyl, aminoalkyl, the residue of an amino acid, a carbohydrate, monophosphate, diphosphate, triphosphate; —C(O)R', where R' is $OR^1$, $NR^1R^2$, alkyl, aryl, aralkyl, or the residue of an amino acid; or an optionally substituted ester;

$R^{12}$ is hydrogen or alkyl; and the dotted lines indicate the presence of either a single bond or a double bond, wherein the valences of a single bond are completed by hydrogens, provided that if the dotted line between C4 and C5 or between C5 and C6 represents a double bond then the other dotted line between C4 and C5 or between C5 and C6 represents a single bond.

In one embodiment of Formula VII, $R^3$ is —$OR^{11}$, —$NR^{11}R^{12}$, or a carbohydrate; and $R^{11}$ is the residue of an amino acid, a carbohydrate, or an optionally substituted ester.

In one embodiment, $R^1$, $R^2$, $R^5$ and $R^6$ are independently hydrogen, alkyl, halogen or hydroxyl.

In another embodiment, $R^1$, $R^2$, $R^5$ and $R^6$ are independently methyl, ethyl or propyl.

In still another embodiment, $R^1$, $R^2$, $R^5$ and $R^6$ are independently thiomethyl, hydroxymethyl or cyano.

In another embodiment, $R^1$, $R^2$, $R^5$ and $R^6$ are independently vinyl or ethynyl.

In still another embodiment, $R^1$, $R^2$, $R^5$ and $R^6$ are independently fluoro, bromo, chloro or iodo.

In one embodiment of Formula VII, $R^6$ is alkyl or fluoro. In yet another embodiment of Formula VII, $R^1$, $R^2$ and $R^5$ are independently hydrogen or alkyl. In another embodiment, $R^1$ and $R^2$ are hydroxyl. In still another embodiment, $R^1$ and $R^2$ are independently hydroxyl or halogen. In another embodiment of Formula VII, $R^1$ is alkyl; and $R^2$ and $R^5$ are hydrogen.

In another embodiment, of Formula VII, $R^2$ is alkyl; and $R^1$ and $R^5$ are hydrogen. In still another embodiment, of Formula VII, $R^5$ is alkyl; and $R^1$ and $R^2$ are hydrogen.

In another embodiment of Formula VII, $R^3$ is —$OR^{11}$ and $R^{11}$ is the residue of a naturally occurring amino acid; and $R^1$, $R^2$, $R^5$ and $R^6$ are hydrogen.

In another embodiment of Formula VII, $R^3$ is —$NR^{11}R^{12}$; $R^{11}$ is the residue of a naturally occurring amino acid or a carbohydrate; $R^{12}$ is hydrogen; and $R^1$, $R^2$, $R^5$ and $R^6$ are hydrogen.

In another embodiment of Formula VII, $R^3OR^{11}$, $R^{11}$ is a carbohydrate; and $R^1$, $R^2$, $R^5$ and $R^6$ are hydrogen.

In another embodiment of Formula VII, $R^3$ is —C(O)R', where R' is alkyl, aryl, aralkyl, or the residue of an amino acid; and $R^1$, $R^2$, $R^5$ and $R^6$ are hydrogen.

In one embodiment of Formula VII, the dotted line between C4 and C5 represents a single bond and the dotted line between C5 and C6 represents a single bond.

In another embodiment of Formula VII, the dotted line between C4 and C5 represents a single bond and the dotted line between C5 and C6 represents a double bond.

In another embodiment of Formula VII, the dotted line between C4 and C5 represents a double bond and the dotted line between C5 and C6 represents a single bond.

In still another embodiment of Formula VII, the dotted line between C1 and C2 represents a single bond. In still another embodiment, the dotted line between C1 and C2 represents a double bond.

In one embodiment of Formula VII, the dotted lines between C4 and C5 and between C5 and C6 represent a single bond, and the hydrogen at the C5 bridgehead carbon is in the alpha configuration. In another embodiment, the dotted lines between C4 and C5 and between C5 and C6 represent a single bond, and the hydrogen at the C5 bridgehead carbon is in the beta configuration In one embodiment of Formula VII, $R^3$ comprises a naturally occurring α-amino acid in the L-configuration. In another embodiment, $R^3$ comprises a residue of L-valine. In another embodiment, $R^3$ comprises an amino acid residue with the D-configuration. In another embodiment, $R^3$ comprises a non-natural amino acid. In other embodiments, $R^3$ comprises the residue of a β γ or δ amino acid.

In one preferred embodiment of Formula V, $R^3$ represents an ester of an amino acid. In another embodiment, $R^3$ represents an ester of an amino acid residue where the ester bond is formed with a carboxylate group on the side chain of the amino acid. In certain embodiments of Formula V, a residue of an amino acid is connected to the steroid ring system at the carboxyl group of the amino acid. In other embodiments, a residue of an amino acid is connected to the steroid at the amino acid side chain. For example, amino acids that contain side chains with functional groups that are capable of forming a bond with a hydroxy or a ketone group may be boded to the steroid ring by such a group. In other embodiments, the reactive groups on the amino acid side chains may displace leaving groups formed on the steroid moiety to form a covalent bond. Non-limiting examples of amino acids with reactive groups in the side chain include lysine, cysteine, serine, tyrosine, aspartic acid, arginine and the like.

The amino acid(s) in any of the embodiments of the invention described herein may be naturally occurring or synthetic amino acids and may be in the D or L stereoisomeric form or may exist as a D, L mixture. For example the 20 naturally occurring α-amino acids in the L-configuration are encompassed by the invention as well as α-amino acids in the D-configuration. Synthetic amino acids in either stereoisomeric form are also encompassed.

In one embodiment, a compound of Formula VII with the stereochemical configuration of Formula VIIa is provided:

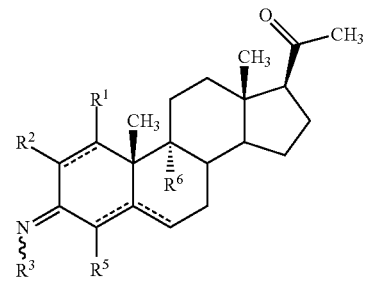

wherein the definition of variables $R^1$, $R^2$, $R^3$, $R^5$, $R^6$, are as defined in Formula VII above.

In another embodiment, a compound of Formula VII with the stereochemical configuration of Formula VIIb is provided:

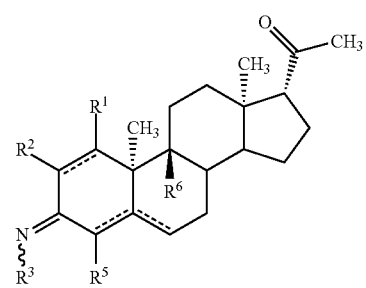

wherein the definition of variables $R^1$, $R^2$, $R^3$, $R^4$, $R^5$, and $R^6$ are as defined in Formula VII above.

In another embodiment of the invention, a progesterone analogue of Formula VIII is provided:

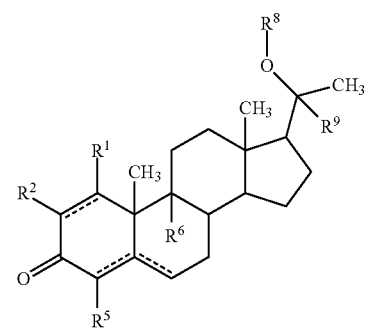

or a pharmaceutically acceptable salt, ester or prodrug thereof, wherein $R^1$, $R^2$, $R^5$ and $R^6$ are independently hydrogen, alkyl, halogen, hydroxyl cycloalkyl, cycloalkenyl, alkenyl, alkynyl, aryl, alkylaryl, arylalkyl, heterocyclic, heteroaryl, amino, thiol, alkoxy, sulfide, nitro, cyano, azide, sulfonyl, acyl, carboxyl, an ester, an amide, carbamate, carbonate, an amino acid residue or a carbohydrate;

$R^8$ is hydrogen, optionally substituted acyl, a residue of an amino acid, a carbohydrate, monophosphate, diphosphate, triphosphate; —C(O)R', where R' is alkyl, aryl, aralkyl, $OR^1$, $NR^1R^2$ or the residue of an amino acid; or, $R^8$ together with $R^9$ and the oxygen forms an optionally substituted 5-6 membered heterocyclic or heteroaryl ring containing 1-4 nitrogen, oxygen or sulfur atoms;

$R^9$ is hydrogen, alkyl, or $R^9$ together with the oxygen and $R^8$ forms an optionally substituted 5-6 membered heterocyclic or heteroaryl ring containing 1-4 nitrogen, oxygen or sulfur atoms; and the dotted lines indicate the presence of either a single bond or a double bond, wherein the valences of a single bond are completed by hydrogens, provided that if the dotted line between C4 and C5 or between C5 and C6 represents a double bond then the other dotted line between C4 and C5 or between C5 and C6 represents a single bond; and with the proviso that $R^8$ does not represent an ester of aspartic acid, glutamic acid, gamma amino butyric acid or α-2-(hydroxyethylamino)-propionic acid; and with the proviso that when Y is N, $R^8$ does not represent aspartic acid, glutamic acid, gamma amino butyric acid or α-2-(hydroxyethylamino)-propionic acid.

In one embodiment of Formula VIII, $R^8$ is hydrogen, optionally substituted acyl, a residue of an amino acid or a carbohydrate.

In one embodiment, $R^1$, $R^2$, $R^5$ and $R^6$ are independently hydrogen, alkyl, halogen or hydroxyl.

In another embodiment, $R^1$, $R^2$, $R^5$ and $R^6$ are independently methyl, ethyl or propyl.

In still another embodiment, $R^1$, $R^2$, $R^5$ and $R^6$ are independently thiomethyl, hydroxymethyl or cyano.

In another embodiment, $R^1$, $R^2$, $R^5$ and $R^6$ are independently vinyl or ethynyl.

In still another embodiment, $R^1$, $R^2$, $R^5$ and $R^6$ are independently fluoro, bromo, chloro or iodo.

In still another embodiment, $R^9$ is hydrogen or methyl.

In another embodiment of Formula VIII, $R^6$ is alkyl or fluoro. In yet another embodiment of Formula VIII, $R^1$, $R^2$ and $R^5$ are independently hydrogen or alkyl. In another embodiment, $R^1$ and $R^2$ are hydroxyl. In still another embodiment, $R^1$ and $R^2$ are independently hydroxyl or halogen. In another embodiment of Formula VIII, $R^1$ is alkyl; and $R^2$ and $R^5$ are hydrogen. In another embodiment, of Formula VIII, $R^2$ is alkyl; and $R^1$ and $R^5$ are hydrogen. In still another embodiment, of Formula VIII, $R^5$ is alkyl; and $R^1$ and $R^2$ are hydrogen.

In another embodiment of Formula VIII, $R^8$ is the residue of a naturally occurring amino acid; and $R^1$, $R^2$, $R^5$, $R^6$ and $R^9$ are hydrogen.

In another embodiment of Formula VIII, $R^8$ is the residue of a naturally occurring amino acid or a carbohydrate; $R^9$ is alkyl; and $R^1$, $R^2$, $R^5$ and $R^6$ are hydrogen.

In one embodiment of Formula VIII, $R^1$ is alkyl; and $R^2$, $R^5$ and $R^9$ are hydrogen.

In another embodiment of Formula VIII, $R^1$ and $R^9$ are alkyl; and $R^2$ and $R^5$ are hydrogen.

In another embodiment of Formula VIII, $R^8$ is a carbohydrate; and $R^1$, $R^2$, $R^5$, $R^6$ and $R^9$ are hydrogen.

In another embodiment of Formula VIII, $R^8$ is —C(O)R', where R' is alkyl, aryl, aralkyl, or the residue of an amino acid; and $R^1$, $R^2$, $R^5$ and $R^6$ are hydrogen.

In one embodiment of Formula VIII, the dotted line between C4 and C5 represents a single bond and the dotted line between C5 and C6 represents a single bond.

In another embodiment of Formula VIII, the dotted line between C4 and C5 represents a single bond and the dotted line between C5 and C6 represents a double bond.

In another embodiment of Formula VIII, the dotted line between C4 and C5 represents a double bond and the dotted line between C5 and C6 represents a single bond.

In still another embodiment of Formula VIII, the dotted line between C1 and C2 represents a single bond. In still another embodiment, the dotted line between C1 and C2 represents a double bond.

In one embodiment of Formula VIII, the dotted lines between C4 and C5 and between C5 and C6 represent a single bond, and the hydrogen at the C5 bridgehead carbon is in the alpha configuration. In another embodiment, the dotted lines between C4 and C5 and between C5 and C6 represent a single bond, and the hydrogen at the C5 bridgehead carbon is in the beta configuration In one embodiment of Formula VIII, $R^8$ is the residue of a naturally occurring α-amino acid in the L-configuration. In another embodiment, $R^8$ is a residue of L-valine. In another embodiment, $R^8$ is an amino acid residue with the D-configuration. In another embodiment, $R^8$ represents a residue of a non-natural amino acid. In other embodiments, $R^8$ represents the residue of a β γ or δ amino acid.

In one preferred embodiment of Formula VIII, $R^8$ represents an ester of an amino acid. In another embodiment, $R^8$ represents an ester of an amino acid residue where the ester bond is formed with a carboxylate group on the side chain of the amino acid.

In one embodiment, a compound of Formula VIII with the stereochemical configuration of Formula VIIIa is provided:

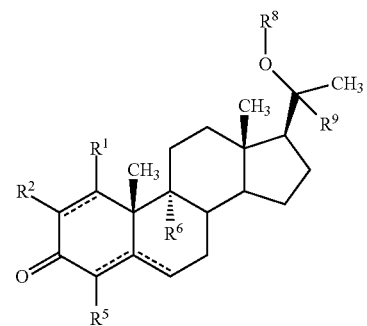

VIIIa wherein the definition of variables $R^1$, $R^2$, $R^5$, $R^6$, $R^8$, and $R^9$ are as defined in Formula VIII above.

In another embodiment, a compound of Formula VIII with the stereochemical configuration of Formula VIIIb is provided:

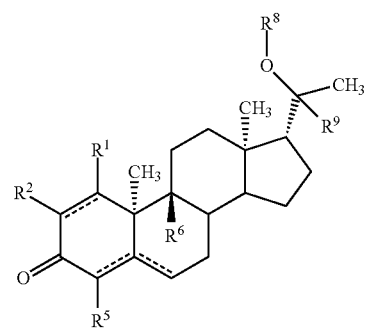

VIIIb wherein the definition of variables $R^1$, $R^2$, $R^5$, $R^6$, $R^8$ and $R^9$ are as defined in Formula VIII above.

In still another embodiment of the invention, a steroid analogue of Formula IX is provided:

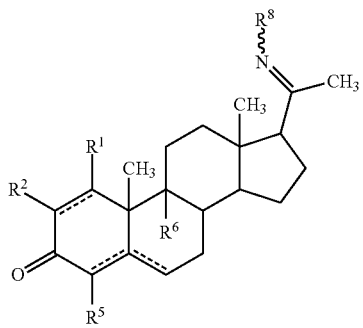

IX or a pharmaceutically acceptable salt, ester or prodrug thereof,
wherein $R^1$, $R^2$, $R^5$ and $R^6$ are independently hydrogen, alkyl, halogen, hydroxyl cycloalkyl, cycloalkenyl, alkenyl, alkynyl, aryl, alkylaryl, arylalkyl, heterocyclic, heteroaryl, amino, thiol, alkoxy, sulfide, nitro, cyano, azide, sulfonyl, acyl, carboxyl, an ester, an amide, carbamate, carbonate, an amino acid residue or a carbohydrate;
$R^8$ is $-OR^{11}$, $-NR^{11}R^{12}$, $-C(O)R'$, where R' is alkyl, aryl, aralkyl, $OR^1$, $NR^1R^2$ or the residue of an amino acid; or a carbohydrate;
$R^{11}$ is hydrogen, optionally substituted alkyl, hydroxyalkyl, aminoalkyl, the residue of an amino acid, a carbohydrate or an optionally substituted ester; $-C(O)R'$, where R' is alkyl, aryl, aralkyl, $OR^1$, $NR^1R^2$ or the residue of an amino acid;
$R^{12}$ is hydrogen or alkyl; and the dotted lines indicate the presence of either a single bond or a double bond, wherein the valences of a single bond are completed by hydrogens, provided that if the dotted line between C4 and C5 or between C5 and C6 represents a double bond then the other dotted line between C4 and C5 or between C5 and C6 represents a single bond; and with the proviso that $R^8$ does not represent aspartic acid, glutamic acid, gamma amino butyric acid or α-2-(hydroxyethylamino)-propionic acid.

In one embodiment, $R^1$, $R^2$, $R^5$ and $R^6$ are independently hydrogen, alkyl, halogen or hydroxyl.

In another embodiment, $R^1$, $R^2$, $R^5$ and $R^6$ are independently methyl, ethyl or propyl.

In still another embodiment, $R^1$, $R^2$, $R^5$ and $R^6$ are independently thiomethyl, hydroxymethyl or cyano.

In another embodiment, $R^1$, $R^2$, $R^5$ and $R^6$ are independently vinyl or ethynyl.

In still another embodiment, $R^1$, $R^2$, $R^5$ and $R^6$ are independently fluoro, bromo, chloro or iodo.

In one embodiment of Formula IX, $R^6$ is alkyl or fluoro. In yet another embodiment of Formula IX, $R^1$, $R^2$ and $R^5$ are independently hydrogen or alkyl. In another embodiment, $R^1$ and $R^2$ are hydroxyl. In still another embodiment, $R^1$ and $R^2$ are independently hydroxyl or halogen. In another embodiment of Formula IX, $R^1$ is alkyl; and $R^2$ and $R^5$ are hydrogen. In another embodiment, of Formula IX, $R^2$ is alkyl; and $R^1$ and $R^5$ are hydrogen. In still another embodiment, of Formula IX, $R^5$ is alkyl; and $R^1$ and $R^2$ are hydrogen.

In another embodiment of Formula IX, $R^3$ is $-OR^{11}$ and $R^{11}$ is the residue of a naturally occurring amino acid; and $R^1$, $R^2$, $R^5$ and $R^6$ are hydrogen.

In another embodiment of Formula IX, $R^8$ is $-NR^{11}R^{12}$; $R^{11}$ is the residue of a naturally occurring amino acid or a carbohydrate; $R^{12}$ is hydrogen; and $R^1$, $R^2$, $R^5$ and $R^6$ are hydrogen.

In another embodiment of Formula IX, $R^8$ is a carbohydrate; and $R^1$, $R^2$, $R^5$ and $R^6$ are hydrogen.

In another embodiment of Formula IX, $R^8$ is $-C(O)R'$, where R' is alkyl, aryl, aralkyl, or the residue of an amino acid; and $R^1$, $R^2$, $R^5$ and $R^6$ are hydrogen.

In one embodiment of Formula IX, the dotted line between C4 and C5 represents a single bond and the dotted line between C5 and C6 represents a single bond.

In another embodiment of Formula IX, the dotted line between C4 and C5 represents a single bond and the dotted line between C5 and C6 represents a double bond.

In another embodiment of Formula IX, the dotted line between C4 and C5 represents a double bond and the dotted line between C5 and C6 represents a single bond.

In still another embodiment of Formula IX, the dotted line between C1 and C2 represents a single bond. In still another embodiment, the dotted line between C1 and C2 represents a double bond.

In one embodiment of Formula IX, the dotted lines between C4 and C5 and between C5 and C6 represent a single bond, and the hydrogen at the C5 bridgehead carbon is in the alpha configuration. In another embodiment, the dotted lines between C4 and C5 and between C5 and C6 represent a single bond, and the hydrogen at the C5 bridgehead carbon is in the beta configuration In one embodiment of Formula IX, $R^8$ comprises a naturally occurring α-amino acid in the L-configuration. In another embodiment, $R^8$ comprises a residue of L-valine. In another embodiment, $R^8$ comprises an amino acid residue with the D-configuration. In another embodiment, $R^8$ comprises a non-natural amino acid. In other embodiments, $R^8$ comprises the residue of a β γ or δ amino acid.

In one embodiment, a compound of Formula IX with the stereochemical configuration of Formula IXa is provided:

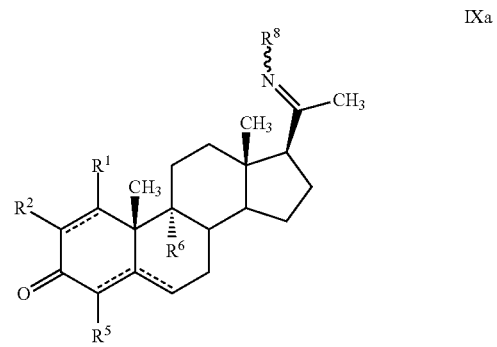

IXa wherein the definition of variables $R^1$, $R^2$, $R^5$, $R^6$, and $R^8$ are as defined in Formula IX above.

In another embodiment, a compound of Formula IX with the stereochemical configuration of Formula IXb is provided:

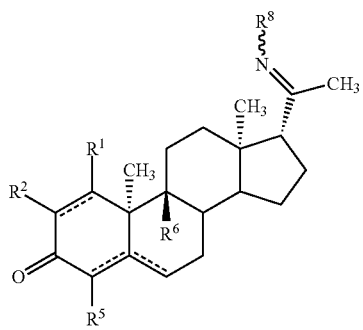

IXb wherein the definition of variables $R^1$, $R^2$, $R^5$, $R^6$, and $R^8$ are as defined in Formula IX above.

In still another embodiment of the invention, a steroid analogue of Formula X is provided:

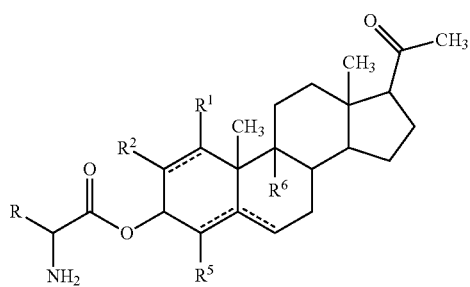

X or a pharmaceutically acceptable salt, ester or prodrug thereof,
wherein R is the side chain of a naturally occurring amino acid; and $R^1$, $R^2$, $R^5$ and $R^6$ are independently hydrogen, alkyl, halogen, hydroxyl cycloalkyl, cycloalkenyl, alkenyl, alkynyl, aryl, alkylaryl, arylalkyl, heterocyclic, heteroaryl, amino, thiol, alkoxy, sulfide, nitro, cyano, azide, sulfonyl, acyl, carboxyl, an ester, an amide, carbamate, carbonate, an amino acid residue or a carbohydrate; and with the proviso that R does not represent the side chain of aspartic acid, glutamic acid, gamma amino butyric acid or α-2-(hydroxyethylamino)-propionic acid.

In one embodiment, $R^1$, $R^2$, $R^5$ and $R^6$ are independently hydrogen, alkyl, halogen or hydroxyl.

In another embodiment, $R^1$, $R^2$, $R^5$ and $R^6$ are independently methyl, ethyl or propyl.

In still another embodiment, $R^1$, $R^2$, $R^5$ and $R^6$ are independently thiomethyl, hydroxymethyl or cyano.

In another embodiment, $R^1$, $R^2$, $R^5$ and $R^6$ are independently vinyl or ethynyl.

In still another embodiment, $R^1$, $R^2$, $R^5$ and $R^6$ are independently fluoro, bromo, chloro or iodo.

In one embodiment of Formula X, $R^6$ is alkyl or fluoro. In yet another embodiment of Formula X, $R^1$, $R^2$ and $R^5$ are independently hydrogen or alkyl. In another embodiment, $R^1$ and $R^2$ are hydroxyl. In still another embodiment, $R^1$ and $R^2$ are independently hydroxyl or halogen. In another embodiment of Formula X, $R^1$, $R^2$, $R^5$ and $R^6$ are hydrogen.

In one embodiment of Formula X, $R^1$ is alkyl; and $R^2$, and $R^5$ are hydrogen. In another embodiment, of Formula X, $R^2$ is alkyl; and $R^1$ and $R^5$ are hydrogen. In still another embodiment, of Formula X, $R^5$ is alkyl; and $R^1$ and $R^2$ are hydrogen.

In one embodiment of Formula X, the dotted line between C4 and C5 represents a single bond and the dotted line between C5 and C6 represents a single bond.

In another embodiment of Formula X, the dotted line between C4 and C5 represents a single bond and the dotted line between C5 and C6 represents a double bond.

In another embodiment of Formula X, the dotted line between C4 and C5 represents a double bond and the dotted line between C5 and C6 represents a single bond.

In still another embodiment of Formula X, the dotted line between C1 and C2 represents a single bond. In still another embodiment, the dotted line between C1 and C2 represents a double bond.

In one embodiment of Formula X, the dotted lines between C4 and C5 and between C5 and C6 represent a single bond, and the hydrogen at the C5 bridgehead carbon is in the alpha configuration. In another embodiment, and the dotted lines between C4 and C5 and between C5 and C6 represent a single bond, the hydrogen at the C5 bridgehead carbon is in the beta configuration In one embodiment of Formula X, R comprises the side chain of a naturally occurring α-amino acid in the L-configuration. In another embodiment, R comprises a residue of L-alanine, L-leucine, L-isoleucine, L-proline, L-proline, L-phenylalanine, L-tryptophan, L-lysine, or L-valine. In another embodiment, R comprises an amino acid residue with the D-configuration.

In one embodiment, a compound of Formula X with the stereochemical configuration of Formula Xa is provided:

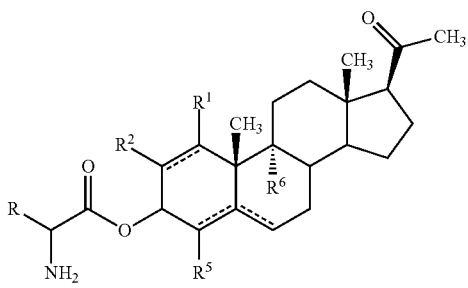

Xa wherein the definition of variables R, $R^1$, $R^2$, $R^5$, and $R^6$, are as defined in Formula X above.

In another embodiment, a compound of Formula X with the stereochemical configuration of Formula Xb is provided:

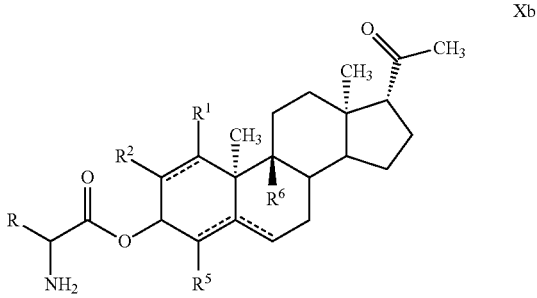

Xb wherein the definition of variables R, R$^1$, R$^2$, R$^5$, and R$^6$, are as defined in Formula X above.

In still another embodiment of the invention, a steroid analogue of Formula XI is provided:

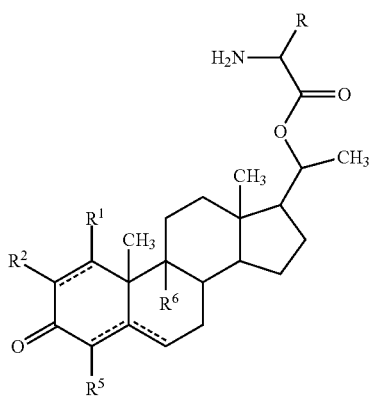

or a pharmaceutically acceptable salt, ester or prodrug thereof, where R is the side chain of a naturally occurring amino acid; and R$^1$, R$^2$, R$^5$ and R$^6$ are independently hydrogen, alkyl, halogen, hydroxyl cycloalkyl, cycloalkenyl, alkenyl, alkynyl, aryl, alkylaryl, arylalkyl, heterocyclic, heteroaryl, amino, thiol, alkoxy, sulfide, nitro, cyano, azide, sulfonyl, acyl, carboxyl, an ester, an amide, carbamate, carbonate, an amino acid residue or a carbohydrate; and with the proviso that R does not represent the side chain of aspartic acid, glutamic acid, gamma amino butyric acid or α-2-(hydroxy-ethylamino)-propionic acid.

In one embodiment, R$^1$, R$^2$, R$^5$ and R$^6$ are independently hydrogen, alkyl, halogen or hydroxyl.

In another embodiment, R$^1$, R$^2$, R$^5$ and R$^6$ are independently methyl, ethyl or propyl.

In still another embodiment, R$^1$, R$^2$, R$^5$ and R$^6$ are independently thiomethyl, hydroxymethyl or cyano.

In another embodiment, R$^1$, R$^2$, R$^5$ and R$^6$ are independently vinyl or ethynyl.

In still another embodiment, R$^1$, R$^2$, R$^5$ and R$^6$ are independently fluoro, bromo, chloro or iodo.

In one embodiment of Formula X, R$^6$ is alkyl or fluoro. In yet another embodiment of Formula X, R$^1$, R$^2$ and R$^5$ are independently hydrogen or alkyl. In another embodiment, R$^1$ and R$^2$ are hydroxyl. In still another embodiment, R$^1$ and R$^2$ are independently hydroxyl or halogen. In another embodiment of Formula X, R$^1$, R$^2$, R$^5$ and R$^6$ are hydrogen. In one embodiment of Formula X, R$^1$ is alkyl; and R$^2$, and R$^5$ are hydrogen. In another embodiment, of Formula X, R$^2$ is alkyl; and R$^1$ and R$^5$ are hydrogen. In still another embodiment, of Formula X, R$^5$ is alkyl; and R$^1$ and R$^2$ are hydrogen.

In one embodiment of Formula X, the dotted line between C4 and C5 represents a single bond and the dotted line between C5 and C6 represents a single bond.

In another embodiment of Formula X, the dotted line between C4 and C5 represents a single bond and the dotted line between C5 and C6 represents a double bond.

In another embodiment of Formula X, the dotted line between C4 and C5 represents a double bond and the dotted line between C5 and C6 represents a single bond.

In still another embodiment of Formula X, the dotted line between C1 and C2 represents a single bond. In still another embodiment, the dotted line between C1 and C2 represents a double bond.

In one embodiment of Formula X, the dotted lines between C4 and C5 and between C5 and C6 represent a single bond, and the hydrogen at the C5 bridgehead carbon is in the alpha configuration. In another embodiment, and the dotted lines between C4 and C5 and between C5 and C6 represent a single bond, the hydrogen at the C5 bridgehead carbon is in the beta configuration In one embodiment of Formula X, R comprises the side chain of a naturally occurring α-amino acid in the L-configuration. In another embodiment, R comprises a residue of L-alanine, L-leucine, L-isoleucine, L-proline, L-proline, L-phenylalanine, L-tryptophan, L-lysine, or L-valine. In another embodiment, R comprises an amino acid residue with the D-configuration.

In one embodiment, a compound of Formula XI with the stereochemical configuration of Formula XIa is provided:

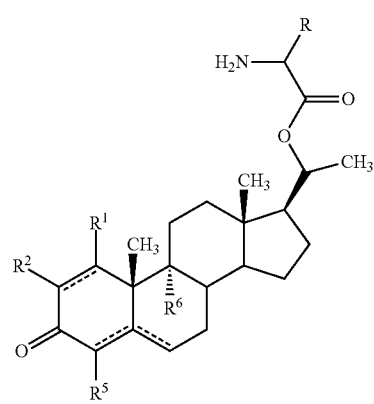

wherein the definition of variables R, R$^1$, R$^2$, R$^5$, and R$^6$, are as defined in Formula XI above.

In another embodiment, a compound of Formula XI with the stereochemical configuration of Formula XIb is provided:

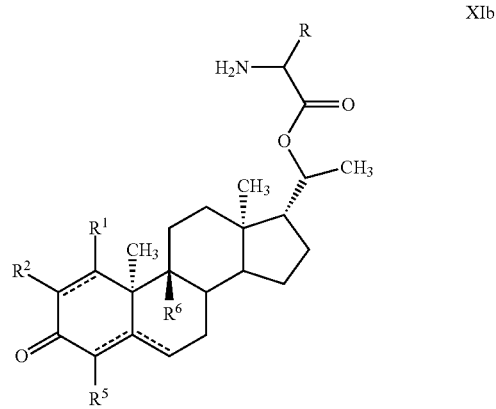

wherein the definition of variables R, R$^1$, R$^2$, R$^5$, and R$^6$, are as defined in Formula XI above.

In another embodiment, a steroid analogue of Formula XII is provided:

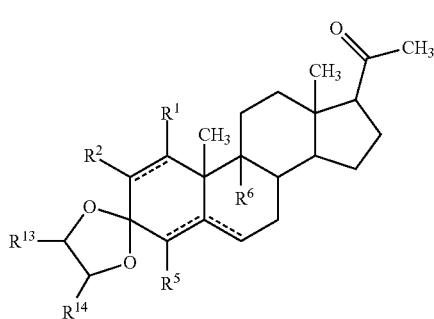

XII or a pharmaceutically acceptable salt, ester or prodrug thereof,
wherein the definition of variables $R^1$, $R^2$, $R^5$, and $R^6$, are as defined in Formula I; and
$R^{13}$ and $R^{14}$ are hydrogen, optionally substituted alkyl, carboxy, sulfonyl, sulfonic acid, sulfonamide, an ester, and amide, hydroxyalkyl, aminoalkyl, the residue of an amino acid, or a carbohydrate.

In another embodiment, a compound of Formula XII with the stereochemical configuration of Formula XIIa is provided:

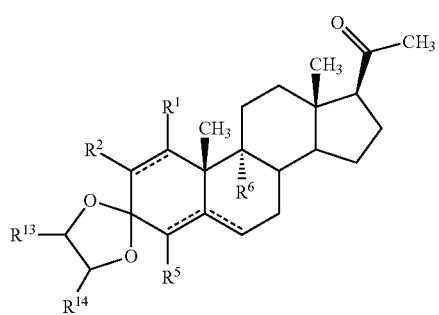

XIIa wherein variables $R^1$, $R^2$, $R^5$, $R^6$, $R^{13}$ and $R^{14}$ are as defined for Formula XII.

In another embodiment, a compound of Formula XII with the stereochemical configuration of Formula XIIb is provided:

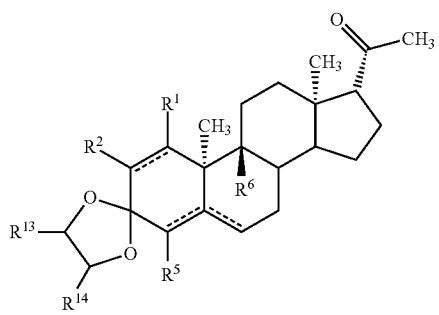

XIIb wherein variables $R^1$, $R^2$, $R^5$, $R^6$, $R^{13}$ and $R^{14}$ are as defined for Formula XII.

In still another embodiment of the invention, a steroid analogue of Formula XIII is provided:

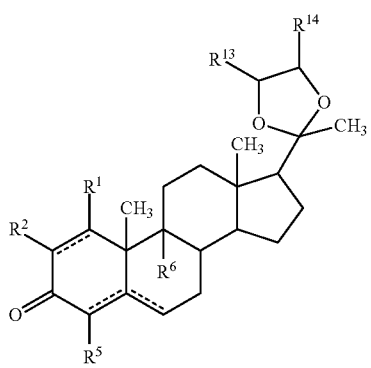

XIII or a pharmaceutically acceptable salt, ester or prodrug thereof,
wherein the definition of variables $R^1$, $R^2$, $R^5$, and $R^6$, are as defined in Formula I; and $R^{13}$ and $R^{14}$ are independently selected from hydrogen, optionally substituted alkyl, hydroxy, alkoxy, amino, alkylamino, dialkylamino, carboxy, sulfonyl, sulfonic acid, sulfonamide, an ester, and amide, hydroxyalkyl, aminoalkyl, alkylaminoalkyl, dialkylaminoalkyl, the residue of an amino acid, or a carbohydrate.

In some embodiments of Formula XIII, variables $R^1$, $R^2$, $R^5$, and $R^6$, are as defined in Formula I; and $R^{13}$ and $R^{14}$ are independently selected from hydrogen, optionally substituted alkyl, carboxy, sulfonyl, sulfonic acid, sulfonamide, an ester, and amide, hydroxyalkyl, aminoalkyl, alkylaminoalkyl, dialkylaminoalkyl, the residue of an amino acid, or a carbohydrate.

In another embodiment, a compound of Formula XIII with the stereochemical configuration of Formula XIIIa is provided:

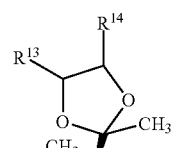

XIIIa wherein variables $R^1$, $R^2$, $R^5$, $R^6$, $R^{13}$ and $R^{14}$ are as defined for Formula XIII.

In another embodiment, a compound of Formula XIII with the stereochemical configuration of Formula XIIIb is provided:

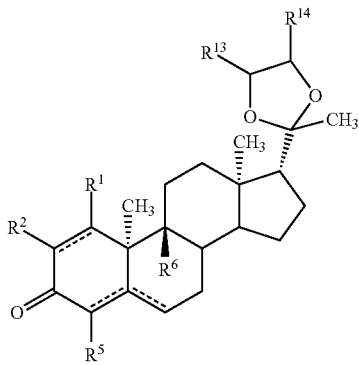

XIIIb wherein variables $R^1$, $R^2$, $R^5$, $R^6$, $R^{13}$ and $R^{14}$ are as defined for Formula XIII.

In still another embodiment, a compound of Formula XIV is provided:

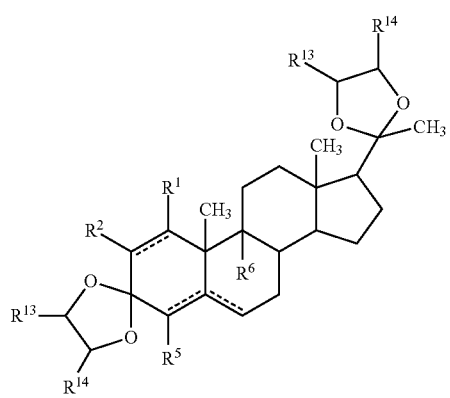

XIV or a pharmaceutically acceptable salt, ester or prodrug thereof, wherein the definition of variables $R^1$, $R^2$, $R^5$, and $R^6$, are as defined in Formula I; and $R^{13}$ and $R^{14}$ are hydrogen, optionally substituted alkyl, carboxy, sulfonyl, sulfonic acid, sulfonamide, an ester, and amide, hydroxyalkyl, aminoalkyl, alkylaminoalkyl, dialkylaminoalkyl, the residue of an amino acid, or a carbohydrate.

In another embodiment, a compound of Formula XIV with the stereochemical configuration of Formula XIVa is provided:

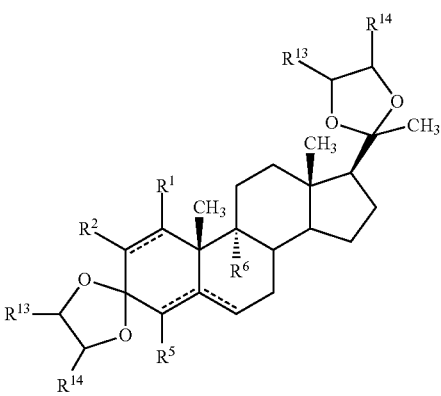

XIVa wherein variables $R^1$, $R^2$, $R^5$, $R^6$, $R^{13}$ and $R^{14}$ are as defined for Formula XIV.

In another embodiment, a compound of Formula XIV with the stereochemical configuration of Formula XIVb is provided:

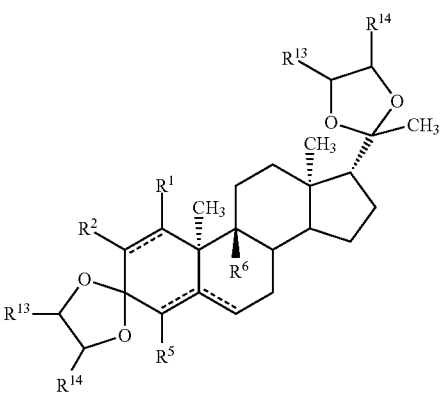

XIVb wherein variables $R^1$, $R^2$, $R^5$, $R^6$, $R^{13}$ and $R^{14}$ are as defined for Formula XIV.

In particular embodiments of the invention, the invention provides the steroid analogues having the Formulas presented in Table 1 below, or a pharmaceutically acceptable salts, esters or prodrugs thereof,

TABLE 1

| Compound # | Structure |
|---|---|
| P1-31 | 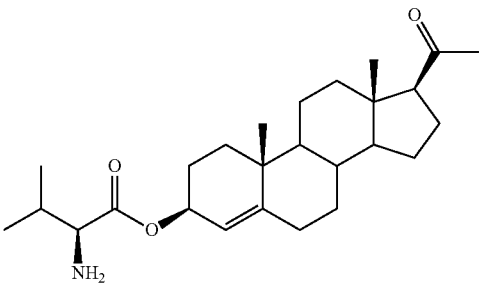 [SMILES: CC(=O)[C@H]1CCC2C3CCC4=C[C@@H](OC(=O)[C@@H](N)C(C)C)CC[C@]4(C)C3CC[C@@]21C] |

TABLE 1-continued

| Compound # | Structure |
|---|---|
| P1-57 | (steroid structure) |
| P1-79 | (steroid structure) |
| P1-113 | (steroid structure) E/Z mixture |
| P1-123 | (steroid structure) |
| P1-131 | (steroid structure) |
| P1-133 | (steroid structure) |
| P1-135 | (steroid structure) |
| P1-29 | (steroid structure) |
| P1-32 | (steroid structure) |
| P1-33 | (steroid structure) |

TABLE 1-continued

| Compound # | Structure |
|---|---|
| P1-34 | (structure: progesterone with tryptophan ester at 3-position) |
| P1-163 | (structure: progesterone with valine ester at 3-position) |
| P1-185 | (structure: progesterone 3-oxime linked via O to valine ester) |
| P1-186 | (structure: progesterone 3-oxime linked via O to valine ester) |
| P2-29-E | (structure: progesterone 3-hydrazone with valine, E-isomer) |
| P2-29-Z | (structure: progesterone 3-hydrazone with valine, Z-isomer) |
| P2-13 | (structure: progesterone with valine ester at 3-position) |
| | (structure: pregn-4-en-3-one with C20 oxime linked via O to amino acid ester) where R is a naturally-occurring amino acid sidechain |
| | (structure: pregn-5-en-3β-ol with C20 oxime linked via O to amino acid ester) where R is a naturally-occurring amino acid sidechain |

TABLE 1-continued

| Compound # | Structure |
|---|---|
| | Steroid with hydrazone linker to amino acid (H2N-CHR-CO-NH-N=C(CH3)- at C17; 3-oxo-Δ4 steroid A-ring) where R is a naturally-occurring amino acid sidechain |
| | Steroid with hydrazone linker to amino acid (H2N-CHR-CO-NH-N=C(CH3)- at C17; 3β-hydroxy-Δ5 steroid) where R is a naturally-occurring amino acid sidechain |
| | Pregnenolone glucuronide (3β-O-glucuronide of pregn-5-en-20-one) |
| | Progesterone semicarbazone amino acid conjugate (R-CH(CO2H)-NH-CO-NH-N=C(CH3)- at C17; 3-oxo-Δ4 steroid) where R is a sidechain of a naturally-occurring amino acid |
| | Progesterone 20-glucuronide oxime (glucuronic acid-O-N=C(CH3)- at C17; 3-oxo-Δ4 steroid) |
| | Progesterone 20-phosphate oxime ((HO)2P(O)-O-N=C(CH3)- at C17; 3-oxo-Δ4 steroid) |

TABLE 1-continued

| Compound # | Structure |
|---|---|
| | (steroid with 3-O-phosphate and 20-oxime-O-phosphate) |
| | (steroid 3-O-amino acid ester, Δ5, with 20-acetyl; R is the sidechain of a naturally occurring amino acid) |
| | (steroid 3-O-(amino acid)-oxime ester at C-20, Δ5, 3-O-amino acid ester; where each R is independently the sidechain of a naturally occurring amino acid) |
| | (steroid 3-O-(α-acyloxy) ester linked via oxime at C-20, 3β-OH, Δ5; where R is the sidechain of a naturally occurring amino acid) |
| | (3-(2-isopropyl-5-oxoimidazolidin-1-yl)imino steroid with 20-acetyl) |
| | (3-hydroxyimino-Δ4-pregnen-20-one) |
| | (3-hydroxyimino-Δ4-pregnen-20-one, isomer) |

TABLE 1-continued

| Compound # | Structure |
|---|---|
| | (steroid structure with bis-dioxolane dicarboxylic acid groups) |
| | (steroid structure with dioxolane dicarboxylic acid group) |
| | (steroid structure with dioxolane dicarboxylic acid groups at C-3) |
| | (steroid semicarbazone structure)<br>wherein R¹ and R² are as defined for formula I |

TABLE 1-continued

| Compound # | Structure |
|---|---|
| | (progesterone semicarbazide derivative)<br>wherein R¹ and R² are as defined for formula I |
| | (progesterone oxime with dihydroxypropyl ether) |
| | (progesterone oxime with dihydroxypropyl ether, isomer) |

Stereochemistry

It is understood that based on the number of asymmetric centers, a total number of $2^n$ possible stereochemical isomers is possible. The present invention includes all possible stereochemical configurations of the compounds.

In some embodiments the stereochemistry of the compounds of the invention will retain the natural stereochemistry of the natural steroid. For example, the stereochemistry at C8, C9, C10, C13, C14 and C17 will retain the stereochemistry of the natural steroid compounds. In contrast, the compounds of the invention include compounds with variable configurations at C-3 and C-5 of the steroid ring system. In some embodiments, the configuration of C-3 is alpha. In other embodiments, the configuration of C-3 is beta. Similarly, in some embodiments, the configuration of C-5 is alpha, and in other embodiments the configuration at C-5 is beta. All possible combinations of stereochemical configurations at C-3 and C-5 are embraced by the invention.

Unless otherwise indicated, the stereochemistry of the compounds of the invention will retain the natural stereochemistry of progesterone at the bridgehead carbon atoms C-8, C-9, C-14 and C-17. In addition, the stereochemistry of the quaternary carbons C-10 and C-13 will also retain the stereochemistry of the progesterone, unless indicated otherwise. In contrast, the compounds of the invention include compounds with variable configurations at C-3 and C-5 of the steroid ring system. In some embodiments, the configuration of C-3 is alpha. In other embodiments, the configuration of C-3 is beta. Similarly, in some embodiments, the configuration of C-5 is alpha, and in other embodiments the configuration at C-5 is beta. All possible combinations of stereochemical configurations at C-3 and C-5 are embraced by the invention.

In one embodiment of the invention, the pure E- or Z-isomers of the carbonyl-derivatives of the steroid compounds, such as oximes derivatives and the like, are provided. In another embodiment, the invention provides mixtures of E- and Z-isomers of the carbonyl derivatives of the neuroprotective compounds.

The present invention also encompasses all possible stereochemical configurations of asymmetric substituents, such as amino acids. As described above, the naturally occurring α-amino acids in L, D, and D,L configurations are encompassed. Furthermore, all possible stereochemical configurations of non-natural synthetic amino acids are encompassed by the invention.

II. Definitions

It should be understood that the various possible stereoisomers of the groups mentioned above and herein are within the meaning of the individual terms and examples, unless otherwise specified. As an illustrative example, "1-methyl-butyl" exists in both the (R) and the (S) form, thus, both (R)-1-methyl-butyl and (S)-1-methyl-butyl is covered by the term "1-methyl-butyl," unless otherwise specified. Several biological compounds are designed by the (D) and the (L) form, rather than the (R) and the (S) form, respectively. As an another illustrative example, "glycine" exists in both the (D) and the (L) form; therefore, both (D)-glycine and (L)-glycine are covered by the term "glycine" unless otherwise specified.

As used herein, the term "isolated enantiomer" refers to a composition that includes at least approximately 95% to 100%, or more preferably, over 97% of a single enantiomer of that compound.

As used herein, the term "substantially free of" or "substantially in the absence of" refers to a composition that includes at least 85 or 90% by weight, preferably 95% to 98% by weight, and even more preferably 99% to 100% by weight, of the designated enantiomer of that compound.

The term "independently" is used herein to indicate that the variable that is independently applied varies independently from application to application. Thus, in a compound such as R"XYR", wherein R" is "independently carbon or nitrogen," both R" can be carbon, both R" can be nitrogen, or one R" can be carbon and the other R" nitrogen.

Whenever a range is referred to herein, the range independently includes every element thereof. For example, the term "$C_{1-5}$ alkyl" independently includes $C_1$-alkyl, $C_2$-alkyl, $C_3$-alkyl, $C_4$-alkyl, $C_5$-alkyl.

The term "alkyl," as used herein unless otherwise specified, is intended to have its customary meaning in the art and includes optionally substituted saturated straight, branched, or cyclic, primary, secondary, or tertiary hydrocarbons. Alkyl, typically is $C_{1-16}$ alkyl but can also be lower alkyl, including $C_{1-10}$ or $C_{1-5}$ alkyl. In exemplary embodiments, alkyl includes methyl, ethyl, propyl, isopropyl, butyl, isobutyl, t-butyl, pentyl, cyclopentyl, isopentyl, neopentyl, hexyl isohexyl, cyclohexyl, cyclohexylmethyl, 3-methylpentyl, 2,2-dimethylbutyl and 2,3-dimethylbutyl. When the alkyl group is a cyclic group, it is typically between $C_{3-12}$ or between $C_{3-8}$ and can include one or more cycles. The alkyl group can be optionally substituted with one or more moieties. Examples of suitable substituents include alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, thiol, imine, sulfonic acid, sulfate, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the pharmacological activity of this compound, either unprotected, or protected as necessary, as known to those skilled in the art, for example, as taught in Greene et al., "Protective Groups in Organic Synthesis," John Wiley and Sons, 4$^{th}$ edition, 2007.

The term "protected" as used herein and unless otherwise defined refers to a group that is added to an oxygen, nitrogen, sulfur or phosphorus atom to prevent its further reaction or for other purposes. A wide variety of oxygen and nitrogen protecting groups are known to those skilled in the art or organic synthesis. Suitable protecting groups are described, for example, in Greene, et al., "Protective Groups in Organic Synthesis," John Wiley and Sons, 4$^{th}$ edition, 2007.

The term "aryl," as used herein, is intended to have its customary meaning in the art and includes, for example, phenyl, biphenyl, and naphthyl and the like. The aryl group can be optionally substituted. Non-limiting examples of substituents include hydroxyl, amino, amido, alkylamino, dialkylamino, haloalkyl, arylamino, alkoxy, aryloxy, halo, nitro, cyano, sulfonic acid, thiol, imine, sulfonyl, sulfanyl, fulfinyl, fulfamonyl, ester, sulfate, phosphonic acid, phosphate, phosphonyl, phosphinyl, phosphoryl, phosphonate, phosphine, thioester, thioether, acid halide, anhydride, oxime, hydrozine, carbamate or carboxyl, either unprotected, or protected as necessary, as known to those skilled in the art, for example, as taught in Greene, et al., "Protective Groups in Organic Synthesis," John Wiley and Sons, 4$^{th}$ edition, 2007.

The term "aralkyl," as used herein, and unless otherwise specified, refers to an optionally substituted aryl group as defined above linked to the molecule through an alkyl group as defined above. The term alkaryl or alkylaryl as used herein, and unless otherwise specified, refers to an alkyl group as defined above linked to the molecule through an aryl group as defined above. In each of these groups, the alkyl group can be optionally substituted as describe above and the aryl group can be optionally substituted as described above or with any other viable functional group that does not inhibit the pharmacological activity of this compound, either unprotected, or protected as necessary, as known to those skilled in the art, for example, as taught in Greene, et al., "Protective Groups in Organic Synthesis," John Wiley and Sons, 4$^{th}$ edition, 2007. Specifically included within the scope of the term aryl are phenyl; naphthyl; phenylmethyl; phenylethyl; 3,4,5-trihydroxyphenyl; 3,4,5-trimethoxyphenyl; 3,4,5-triethoxyphenyl; 4-chlorophenyl; 4-methylphenyl; 3,5-di-tertiarybutyl-4-hydroxyphenyl; 4-fluorophenyl; 4-chloro-1-naphthyl; 2-methyl-1-naphthylmethyl; 2-naphthylmethyl; 4-chlorophenylmethyl; 4-tertiarybutylphenyl; 4-tertiarybutylphenylmethyl and the like.

The term "halo" or "halogen," as used herein includes chloro, bromo, iodo and fluoro.

The term "heteroatom," as used herein, refers to oxygen, sulfur, nitrogen or phosphorus.

The term "alkylamino" or "arylamino" refers to an amino group that has one or two alkyl or aryl substituents, respectively.

The term "alkoxy," as used herein, and unless otherwise specified, refers to a moiety of the structure —O-alkyl, wherein alkyl is as defined above.

The term "acyl" refers to moiety of the Formula —C(O)R', wherein R' is alkyl, aryl, alkaryl, aralkyl, heteroaromatic, heterocyclic, alkoxyalkyl including methoxymethyl, arylalkyl including benzyl, aryloxyalkyl, such as phenoxymethyl, aryl including optionally substituted phenyl.

As used herein, a "leaving group" means a functional group that is cleaved from the molecule to which it is attached under appropriate conditions.

The term "heteroaryl" or "heteroaromatic," as used herein are intended to have their customary meaning in the art, and include an aromatic group that includes at least one sulfur, oxygen, nitrogen or phosphorus in the aromatic ring. The term "heterocyclic" refers to a nonaromatic cyclic group wherein there is at least one heteroatom, such as oxygen, sulfur, nitrogen or phosphorus in the ring. Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, or imidazole. The heteroaromatic group can be optionally substituted as described above for aryl. The heterocyclic group can be optionally substituted with one or more moieties. Non-limiting examples of suitable substituents include alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., "Protective Groups in Organic Synthesis," John Wiley and Sons, 4$^{th}$ edition, 2007. The heteroaromatic can be partially or totally hydrogenated as desired. As a non-limiting example, dihydropyridine can be used in place of pyridine. Functional oxygen and nitrogen groups on the heteroaryl group can be protected as necessary or desired. Suitable protecting groups are well known to those skilled in the art, and include, but are not limited to, 9-fluorenylmethoxycarbonyl (Fmoc), benzyl, trimethylsilyl, dimethylhexylsilyl, t-butyldimethylsilyl, and t-butyldiphenylsilyl, trityl or substituted trityl, alkyl groups, acyl groups such as acetyl, benzoyl, and propionyl, methanesulfonyl, and p-toluenesulfonyl.

Unless otherwise specified, the term "amino acid" includes naturally occurring and synthetic α, βγ or δ amino acids. The naturally occurring amino acids are glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine.

The term "residue of an amino acid" is intended to mean that an amino acid is bonded to the compound at any substitutable position, including for example, through an ester bond to the carboxyl group of the amino acid. Other substitutable positions include the amino group or the sidechain of the amino acid.

The term "side chain of a naturally occurring amino acid" refers to the side chains of the 20 naturally occurring amino acids, including hydrogen (i.e. the sidechain of glycine). The side chains of the naturally occurring amino acids are shown below:

| Alanine | A, Ala | $CH_3$— |
| Arginine | R, Arg | $HN=C(NH_2)$—$NH$—$(CH_2)_3$— |
| Asparagine | N, Asn | $H_2N$—$CO$—$CH_2$— |
| Aspartic acid | D, Asp | $HOOC$—$CH_2$— |
| Cysteine | C, Cys | $HS$—$CH_2$— |
| Glutamine | Q, Gln | $H_2N$—$CO$—$(CH_2)_2$— |
| Glutamic acid | E, Glu | $HOOC$—$(CH_2)_2$— |
| Glycine | G, Gly | H— |
| Histidine | H, His | $N=CH$—$NH$—$CH=C$—$CH_2$— |
| Isoleucine | I, Ile | $CH_3$—$CH_2$—$CH(CH_3)$— |
| Leucine | L, Leu | $(CH_3)_2$—$CH$—$CH_2$— |
| Lysine | K, Lys | $H_2N$—$(CH_2)_4$— |
| Methionine | M, Met | $CH_3$—$S$—$(CH_2)_2$— |
| Phenylalanine | F, Phe | Phenyl-$CH_2$— |
| Proline | P, Pro | —$N$—$(CH_2)_3$—$CH$— |
| Serine | S, Ser | $HO$—$CH_2$— |
| Threonine | T, Thr | $CH_3$—$CH(OH)$— |
| Tryptophan | W, Trp | Phenyl-$NH$—$CH=C$—$CH_2$— |
| Tyrosine | Y, Tyr | 4-OH-Phenyl-$CH_2$— |
| Valine | V, Val | $CH_3$—$CH(CH_2)$— |

In certain embodiments, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. When the term amino acid is used, it is considered to be a specific and independent disclosure of each of the esters of α, β γ or δ glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine in the D and L-configurations.

The term "thio" refers to a sulfur covalently bound to a hydrogen or a carbon based group. Some non-limiting examples include methylmercapto, ethylmercapto, n-propylmercapto, isopropylmercapto or n-butylmercapto, ethylthio, n-propylthio or isopropylthio group. The thio group also can be optionally substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., "Protective Groups in Organic Synthesis," John Wiley and Sons, 4$^{th}$ edition, 2007.

The term "ester" refers to a carbonyl flanked by an alkoxy group and a carbon based group. Esters may be formed from the reaction of a hydroxy group on the compound of the invention with a carboxyl group of another group. Alternatively, an ester may be formed by reaction of a carboxyl group on the compound of the invention with a hydroxy group of another molecule. Some non-limiting examples include hydroxycarbonyl, methoxycarbonyl, ethoxycarbonyl, n-propyloxycarbonyl, isopropyloxycarbonyl, n-butyloxycarbonyl, isobutyloxycarbonyl, tert-butyloxycarbonyl or 1-(cinnamyloxycarbonyloxy)-ethoxy-carbonyl. Esters of amino acids, as used herein, include groups where a carboxyl group of the amino acid forms an ester bond with a hydroxyl group of the molecule. Also included are groups where a hydroxyl group on the amino acid forms a ester bond with a carboxyl group on the molecule. The ester group also can be optionally substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, or any other viable functional group that does not inhibit the pharmacological activity of this compound, either unprotected, or protected as necessary, as known to those skilled in the art, for example, as taught in Greene, et al., "Protective Groups in Organic Synthesis," John Wiley and Sons, 4$^{th}$ edition, 2007.

III. Pharmaceutically Acceptable Salt formulations

Modifications of the active compound can affect the bioavailability and rate of metabolism of the active species, thus providing control over the delivery of the active species. Further, the modifications can affect the activity of the compound, in some cases increasing the activity over the parent compound. This can easily be assessed by preparing the derivative and testing its activity according to the methods described herein, or other method known to those skilled in the art.

In cases where compounds are sufficiently basic or acidic to form stable nontoxic acid or base salts, administration of the compound as a pharmaceutically acceptable salt may be appropriate. The term "pharmaceutically acceptable salts" or "complexes" refers to salts or complexes that retain the desired biological activity of the compounds of the present invention and exhibit minimal undesired toxicological effects.

Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts may also be formed, including, hydrochloride, sulfate, nitrate, bicarbonate and carbonate salts. Alternatively, the pharmaceutically acceptable salts may be made with sufficiently basic compounds such as an amine with a suitable acid affording a physiologically acceptable anion. Alkali metal (for example, sodium, potassium or lithium) or alkaline earth metal (for example calcium) salts of carboxylic acids can also be made.

Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalcturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the Formula —NR$^+$A$^-$, wherein R is as defined above and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

Any of the compounds described herein can be administered as a prodrug to increase the activity, bioavailability, stability or otherwise alter the properties of the compound. A number of prodrug ligands are known. In general, alkylation, acylation or other lipophilic modification of the compound will increase the stability of the compound. Examples of substituent groups that can replace one or more hydrogens on the compound are alkyl, aryl, steroids, carbohydrates, including sugars, 1,2-diacylglycerol and alcohols. Any of these can be used in combination with the disclosed compounds to achieve a desired effect.

IV. Treatment of CNS Damage

The present invention provides methods and compositions for the treatment or prevention of neurodegeneration following an injury to the central nervous system or due to certain neurodegenerative disorders comprising administering an effective amount of steroid analog, or a pharmaceutically acceptable salt, ester or prodrug thereof to a host in need thereof. Multiple physiological events lead to neurodegeneration. These events include, for example, increase in the immune and inflammatory response, demyelinization, and lipid peroxidation. The present invention provides compositions and methods for reducing or eliminating neuronal cell death, edema, ischemia, and enhancing tissue viability following injury to the central nervous system or certain disorders. The analogues, salts, esters or prodrugs of the steroid or secosteroid analogs may be optionally administered with a pharmaceutically acceptable carrier or diluent.

By "treatment or prevention" is intended any enhanced survival, proliferation, and/or neurite outgrowth of the neurons that either prevents or retards neurodegeneration, the progressive loss of neurons. As used herein, "neuroprotection" is the prevention, arrest or reverse progression of neurodegeneration following a central nervous system injury. The neuroprotective effect includes both improved morphological (i.e., enhanced tissue viability) and/or behavioral recovery. CNS injuries that are encompassed within the scope of treatment of the present invention include both traumatic injuries, in particular TBI, and physiological insults such as an ischemic or hemorrhagic stroke. In both instances, a progressive loss of neurons after the initial insult occurs and can be alleviated by use of the inventive compounds.

In certain embodiments, a method of preventing or reducing inflammatory reactions in a patient is provided that includes administering a steroid analog to a host in need thereof. In certain embodiments, methods of neuroprotection are provided comprising administering a compound of the invention, its physiologically acceptable salt or prodrug, optionally in a pharmaceutically acceptable carrier, to a patient at risk of suffering from a stroke. In other embodiments, methods of treating or preventing neuronal damage are provided comprising administering a compound of the invention or its physiologically acceptable salt or prodrug, optionally in a pharmaceutically acceptable carrier, to a patient who has suffered from an ischemic stroke. The method can reduce or prevent neurodegeneration such as that caused by excitotoxic or inflammatory reactions, or can enhance neuronal proliferation, growth or differentiation in the period after the injury. In yet further embodiments, methods of treating or preventing cognitive or behavioral deficits after a stroke is provided comprising administering a compound of the invention or its physiologically acceptable salt or prodrug, optionally in a pharmaceutically acceptable carrier, to a patient who has suffered a stroke. In certain embodiments, the stroke is an ischemic stroke, but it can alternatively be a hemorrhagic stroke.

In other embodiments, the present invention provides a method to achieve a neuroprotective effect following a traumatic CNS injury in a mammal, in particular in a human, comprising administering a therapeutically effective amount of steroid analogue of the invention. A traumatic injury to the CNS is characterized by a physical impact to the central nervous system. The physical forces resulting in a traumatic brain injury cause their effects by inducing three types of injury: skull fracture, parenchymal injury, and vascular injury. A blow to the surface of the brain typically leads to rapid tissue displacement, disruption of vascular channels, and subsequent hemorrhage, tissue injury and edema. Morphological evidence of injury in the neuronal cell body includes pyknosis of nucleus, eosinophilia of the cytoplasm, and disintegration of the cell. Furthermore, axonal swelling can develop in the vicinity of damage neurons and also at great distances away from the site of impact.

In certain embodiments, the compound is administered within twelve hours after onset of a stroke. In certain embodiments, the steroid analogue of the invention is administered within twelve hours after an injury, such as a TBI. In some embodiments, the compounds are administered within 11 hours of a TBI, stroke or other injury to the brain, or within 10 hours, or within 9 hours, or within 8 hours, or within 7 hours, or within 6 hours, or within 5 hours, or within 4 hours, or within 3 hours, such as within two or one hour. In some other embodiments, the compounds are administered within one day (i.e. 24 hours) of the injury. In certain embodiments, the compounds are provided to individuals at risk of a stroke, such as those who are suffering from atherosclerosis or have a family history of heart disease. These compounds can be provided to individuals as a preventative therapy to decrease neural trauma.

In another embodiment, a method for decreasing ischemia following a brain injury is provided comprising administering an effective amount of a steroid analogue of the invention. The methods of the invention provide a means to reduce or eliminate the inflammatory immune reactions that follow a CNS injury. By reducing the inflammatory response, the steroid analogues of the present invention can substantially reduce brain swelling and reduce the amount of neurotoxic substances (e.g., free radicals and excitotoxins) that are released from the site of injury.

The present invention provides for a method of treating a brain injury by administering to a subject steroid analogue of the invention, a pharmaceutically acceptable salt or a prodrug or ester thereof. The concentration of the steroid analogue or salt, ester or prodrug thereof, in accordance with the present invention is effective in the treatment or prevention of neuronal damage that follows either a traumatic, ischemic or hemorrhagic injury to the CNS and hence, elicits a neuroprotective effect. The therapeutically effective amount will depend on many factors including, for example, the specific activity of the steroid analogue administered, the type of injury, the severity and pattern of the injury, the resulting neuronal damage, the responsiveness of the patient, the weight of the patient along with other intraperson variability, the method of administration, and the formulation used.

It is recognized that a traumatic injury to the CNS results in multiple physiological events that impact the extent and rate of neurodegeneration, and thus the final clinical outcome of the injury. The treatment of a traumatic injury to the CNS, as defined by the present invention, encompasses any reduction and/or prevention in one or more of the various physiological events that follow the initial impact. For example, cerebral edema frequently develops following a traumatic injury to the CNS and is a leading cause of death and disability. Cortical contusions, for example, produce massive increases in brain tissue water content which, in turn, can cause increased intracranial pressure leading to reduced cerebral blood flow and additional neuronal loss. Hence, the methods of the invention find use in reducing and/or eliminating cerebral edema and/or reducing the duration of the edemic event following a traumatic injury to the CNS. Assays to determine a reduction in edema are known in the art and include, but are not limited to, a decrease in tissue water content following the administration of the progestin or the progestin metabolite (Betz et al. (1990) Stroke 21:1199-204, which is herein incorporated by reference). Furthermore, an overall improvement in behavioral recovery can also be used as a measure for a decrease in edema. A decrease in edema in the effected tissue by at least about 15% to 30%, about 30% to 45%, about 45% to 60%, about 60% to 80%, or about 80% to 95% or greater will be therapeutically beneficial, as will any reduction in the duration of the edemic event.

Further physiological effects of brain injury include an inflammatory response. In particular, some studies indicate that the acute inflammatory response contributes significantly to injury after ischemia (see Perera, et al. (2005) Inflammation following stroke. *J. Clin. Neurosc.* 13:1-8; Barone and Feuerstein (1999) Inflammatory mediators and stroke: new opportunities for novel therapeutics). The stroke process triggers an inflammatory reaction that may last up to several months. Suppression of inflammation can reduce infarct volume and improve clinical outcomes even with the initiation of therapy after 3 hours of onset of stroke. In addition, an immune response can be triggered both by strokes. Infiltrating leukocytes are thought to contribute to secondary ischemic damage by producing toxic substances that kill brain cells and disrupt the blood-brain barrier (see del Zoppo, et al. (2000) Advances in the vascular pathophysiology of ischemic stroke. *Thromb Res.* 98:73-81) Infiltration occurs when leukocytes bind endothelial intercellular adhesion molecule-1 (ICAM-1) and ICAM-1 is upregulated after ischemia.

TBI also elicits inflammatory, and in particular a immune responses. See, for example, Soares et al. (1995) J. Neurosci. 15:8223-33; Holmin et al. (1995) Acta Neurochir. 132:110-9; Arvin et al. (1996) Neurosci. Biobehay. Rev. 20:445-52. Following a cortical impact, severe inflammatory reactions and gliosis at the impact site and at brain areas distal to the primary site of injury occurs. The inflammatory response is characterized by the expression of adhesion molecules on the vascular surfaces, resulting in the adherence of immune cells and subsequent extravasation into the brain parenchyma. By releasing cytokines, the invading macrophages and neutrophils stimulate reactive astrocytosis. Release of different chemokines by other cell types induces these immune cells to become phagocytic, with the simultaneous release of free radicals and pro-inflammatory compounds, e.g., cytokines, prostaglandins, and excitotoxins (Arvin et al. (1996) Neurosci. Biobehay. Ref 20:445-52; Raivich et al. (1996) Kelo J. Med. 45:239-47; Mattson et al. (1997) Brain Res. Rev. 23:47-61; all of which are herein incorporated by reference).

Assays for assessing the efficacy of the compounds described herein include assays to determine a decrease in an ischemic event include, for example, a decrease in infarct area, improved body weight, and improved neurological outcome. Assays to measure a reduction in lipid peroxidation in both brain homogenate and in mitochondria are known in the art and include, for example, the thiobarbituric acid method (Roof et al. (1997) Mol. Chem. Neuropathol. 31: 1-11; Subramanian et al. (1993) Neurosci. Lett. 155: 151-4; Goodman et al. (1996) J. Neurochem. 66:1836-44; Vedder et al. (1999) J. Neurochem. 72:2531-8; all of which are herein incorporated by reference) and various in vitro free radical generating systems. Furthermore, alterations in the levels of critical free radical scavenger enzymes, such as mitochondrial glutathione can be assayed. See, for example, Subramanian et al. (1993) Neurosci. Lett. 155:151-4; and Vedder et al. (1999) J. Neurochem. 72:2531-8; both of which are herein incorporated by reference.

Methods to quantify the extent of central nervous system damage (i.e., neurodegeneration) and to determine if neuronal damage was treated or prevented following the administration of a progesterone or steroid analogue are well known in the art. Such neuroprotective effects can be assayed at various levels, including, for example, by promoting behavioral and morphological (i.e., enhancing tissue viability) recovery after traumatic brain injury. A variety of anatomical, immunocytochemical and immunological assays to determine the effect of the progestin metabolite on necrosis, apoptosis, and neuronal glial repair are known in the art. As such, the neuroprotection resulting from the methods of the present invention will result in at least about a 10% to 20%, 20% to 30%, 30% to 40%, 40% to 60%, 60% to 80% or greater increase in neuronal survival and/or behavioral recovery as compared to the control groups.

Histological and molecular marker assays for an increase in neuronal survival are known. For example, Growth Associated Protein 43 (GAP-43) can be used as a marker for new axonal growth following a CNS insult. See, for example, Stroemer et al. (1995) Stroke 26:2135-2144, Vaudano et al. (1995) J. of Neurosci 15:3594-3611. Other histological markers can include a decrease in astrogliosis and microgliosis. Alternatively, a delay in cellular death can be assayed using TUNEL labeling in injured tissue. Further anatomical measures that can be used to determine an increase in neuroprotection include counting specific neuronal cell types to determine if the progestin or the progestin metabolite is preferentially preserving a particular cell type (e.g., cholinergic cells) or neurons in general.

In addition, behavioral assays can be used to determine the rate and extent of behavior recovery in response to the treatment. Improved patient motor skills, spatial learning performance, cognitive function, sensory perception, speech and/or a decrease in the propensity to seizure may also be used to measure the neuroprotective effect. Such functional/behavioral tests used to assess sensorimortor and reflex function are described in, for example, Bederson et al. (1986) Stroke 17:472-476, DeRyck et al. (1992) Brain Res. 573:44-60, Markgraf et al. (1992) Brain Res. 575:238-246, Alexis et al. (1995) Stroke 26:2336-2346; all of which are herein incorporated by reference. Enhancement of neuronal survival may also be measured using the Scandinavian Stroke Scale (SSS) or the Barthl Index. Behavioral recovery can be further assessed using the recommendations of the Subcommittee of the NIH/NINDS Head Injury Centers in Humans (Hannay et al. (1996) J. Head Trauma Rehabil. 11:41-50), herein incorporated by reference. Behavioral recovery can be further assessed using the methods described in, for example, Beaumont et al. (1999) Neurol Res. 21:742-754; Becker et al. (1980) Brain Res. 200:07-320; Buresov et al. (1983) Techniques and Basic Experiments for the Study of Brain and Behavior; Kline et al. (1994) Pharmacol. Biochem. Behay. 48:773-779; Lindner et al. (1998) J. Neurotrauma 15:199-216; Morris (1984) J. Neurosci. Methods 11:47-60; Schallert et al. (1983) Pharmacol. Biochem. Behay. 18:753-759.

Assays that can be used to determine if the steroid analogue of the invention is imparting an anti-inflammatory and a nonspecific suppressive effect on the immune system following a traumatic CNS injury include, for example, a reduction in cytokine induced microglial proliferation in vitro (Hoffman et al. (1994) J. Neurotrauma 11:417-31; Garcia-Estrada et al. (1993) Brain Res. 628:271-8; both of which are herein incorporated by reference); a reduction in the generation of cytotoxic free radicals by activated macrophages (Chao et al. (1994) Am. J. Reprod. Immunol. 32:43-52; Robert et al. (1997) Nitric Oxide 1:453-62; Kelly et al. (1997) Biochem. Biophys. Res. Commun. 239:557-61; Ganter et al. (1992) J. Neurosci. Res. 33:218-30; all of which are herein incorporated by reference); a reduction in the expression of inducible nitric oxide synthetase and the amount of nitric oxide release by macrophages (Robert et al. (1997) Nitric Oxide 1:453-62; Miller et al. (1996) J. Leukoc. Biol. 59:442-50; both of which are herein incorporated by reference); the release of a "progesterone-induced blocking factor" that inhibits natural killer cell activity (Cheek et al. (1997) Am. J. Reprod. Immunol. 37:17-20; Szekeres-Bartho et al. (1997) Cell Immunol. 177:194-9; Szekeres-Bartho et al. (1996) Am. J. Reprod. Immunol. 35:348-51; all of which are herein incorporated by reference); a decrease in the number of GFAP-positive astrocytes after brain injury which is suggestive of less secondary damage (Garcia-Estrada et al. (1993) Brain Res. 628:271-8; Garcie-Estrada et al. (1999) Int. J. Dev. Neurosci. 17:145-51; Cheek et al. (1997) Am. J. Reprod. Immunol. 37:17-20; Szekeres-Bartho et al. (1997) Cell Immunol. 177:194-9; Szekeres-Bartho et al. (1996)

Am. J. Reprod. Immunol. 35:348-51; all of which are herein incorporated by reference); a reduction in the number of inflammatory immune cells (OX42-positive cells); a reduction in the loss of ChAT-positive and COX-positive neurons; a reduction in the number of TUNEL-positive and MnSOD-positive neurons; and an increase in the intensity of succinate dehydrogenase and cytochrome oxidase activity.

Furthermore, a reduction in the inflammatory immune reactions following a traumatic brain injury can be assayed by measuring the cytokines level following the injury in the sham controls versus the progestin treated subjects. Cytokines are mediators of inflammation and are released in high concentrations after brain injury. The level of pro-inflammatory cytokines (e.g., interleukin 1-beta, tumor necrosis factor, and interleukin 6) and the level of anti-inflammatory cytokines (e.g., interleukin 10 and transforming growth factor-beta) can be measured. For instance, "real-time" polymerase chain reactions (PCR) can be used to measure the strength of the mRNA signal and ELISA can be used to determine protein levels. In addition, histological analysis for different inflammatory cell types (e.g., reactive astrocytes, macrophages and microglia) can be used to measure a reduction in the inflammatory response.

The compounds of the invention can also have potential for use in other disorders including multiple sclerosis, catamenial epilepsy, diabetic neuropathy, inflammatory disorders (e.g., rheumatoid arthritis, inflammatory bowel disease), hemorrhagic shock, Niemann-Pick disorder, cerebral palsy, and congenital heart disorders.

In specific embodiments, a method of treatment or prevention of neural degeneration related to Amyotrophic Lateral Sclerosis (ALS), is provided comprising administering a steroid analog described herein, or a pharmaceutically acceptable salt, ester or prodrug thereof, to a patient suffering from or at risk of suffering from ALS. ALS, more commonly known as Lou Gehrig's Disease, strikes both males and females, typically between the ages of 40 and 70. This is a motor neuron disorder in which both the upper and lower motor neurons are affected. Patients' muscles atrophy as the motor neurons cease sending signals to initiate movement. This affects not only muscles required for locomotion but also the muscles used in swallowing. Up until the age of 60, males are disproportionally affected at a ratio of 1.5 to 1. After the age of 60, the numbers are equal across genders. The incidence of ALS is approximately ½ that of multiple sclerosis. Life expectancy post-diagnosis is 2-5 years. There are 120,000 cases of ALS diagnosed worldwide and 350,000 patients coping with the disease at any given time. A treatment for ALS will clearly qualify for orphan drug status. The cause of ALS has not been identified. The pathogenesis is poorly understood but excitotoxicity, inflammation, oxidative stress and protein aggregation have been shown. In some cases, super oxide dismutase 1 (SOD1) has been determined to be aberrant. Glutamate toxicity is now generally accepted as part of AS pathology. Progesterone has proven to protect neurons from the effects of this toxicity. The only compound approved for the treatment of ALS is Rilutek™ which may reduce glutamate levels. It is not curative but has reduced the rate of progression in some patients.

In another specific embodiments, a method of treatment or prevention of neural degeneration related to Parkinson's Disease (PD), is provided comprising administering a steroid analog described herein, or a pharmaceutically acceptable salt, ester or prodrug thereof, to a patient suffering from or at risk of suffering from PD. PD is a neurodegenerative disease of unknown etiology that results in the progressive loss of nerve cell function in the brain. Life expectancy is 15-25 years post-diagnosis; however, there is no cure. It is estimated that one million people in the U.S. are living with Parkinson's; a number that is greater than the combined total of multiple sclerosis, muscular dystrophy and amyotrophic lateral sclerosis patients. The incidence of PD increases with age. Nearly 40,000 people are diagnosed each year with PD, of which ~15% will be less than 50 years in age. The cost of PD annually exceeds $25 billion when both direct and indirect costs are combined. In PD, cells in the substania nigra of the brain cease to function properly and die. These cells produce dopamine, a neurotransmitter. Dopamine regulates those parts of the brain which control the initiation of movement and coordination. Without dopamine, a patient will begin to experience tremors, bradykinesia, postural instability, rigidity of limbs and trunk, and/or impaired balance and coordination. Not all patients experience all symptoms nor do they progress at the same rate. PD is ultimately debilitating for many sufferers who require assistance in everyday living.

In another specific embodiments, a method of treatment or prevention of neural degeneration related to spinal cord trauma is provided comprising administering a steroid analog described herein, or a pharmaceutically acceptable salt, ester or prodrug thereof, to a patient in need thereof. In another specific embodiments, a method of treatment or prevention of neural degeneration related to hypoxia is provided comprising administering a steroid analog described herein, or a pharmaceutically acceptable salt, ester or prodrug thereof, to a patient in need thereof.

V. Combination and Alternation Therapy

In further embodiments of the present invention, the steroid analogues of the invention may be administered in combination or alternation with at least one additional neuroprotective agent to enhance neuroprotection following a traumatic CNS injury. In one embodiment, the inventive steroid analogues of the invention may be administered in combination or alternation with other steroid analogues or with progesterone.

Other neuroprotective agents of interest include, for example, compounds that reduce glutamate excitotoxicity and enhance neuronal regeneration. Such agents may be selected from, but not limited to, the group comprising growth factors. As used herein, "growth factor" refers to an extracellular polypeptide-signaling molecule that stimulates a cell to grow or proliferate. Preferred growth factors are those to which a broad range of cell types respond. Examples of neurotrophic growth factors include, but are no limited to, fibroblast growth factor family members such as basic fibroblast growth factor (bFGF) (Abraham et al. (1986) Science 233:545-48), acidic fibroblast growth factor (aFGF) (Jaye et al. (1986) Science 233:541-45), the hst/Kfgf gene product, FGF-3 (Dickson et al. (1987) Nature 326-833), FGF-4 (Zhan et al. (1988) Mol. Cell. Biol. 8:3487-3495), FGF-6 (deLapeyriere et al. (1990) Oncogene 5:823-831), keratinocyte growth factor (KGF) (Finch et al. (1989) Science 245:752-755), and androgen-induced growth factor (AIGF) (Tanaka et al. (1992) Proc. Natl. Acad. Sci. USA 89:8928-8923).

Additional neuroprotective agents include, ciliary neurotrophic factor (CNTF), nerve growth factor (NGF) (Seiler, M. (1984) Brain Research 300:33-39; Hagg T. et al. (1988) Exp Neurol 101:303-312; Kromer L. F. (1987) Science 235:214-216; and Hagg T. et al. (1990) J. Neurosci 10(9): 3087-3092), brain derived neurotrophic factor (BDNF) (Kiprianova, I. et al. (1999) J. Neurosci. Res. 56:21-27), Neurotrophin 3 (NT3), Neurotrophin 4 (NT4), transforming growth factor-β1 (TGF-β1) (Henrick-Noack, P. et al. (1996) Stroke 27:1609-14), bone morphogenic protein (BMP-2) (Hattori, A. et al. (1999) J. Neurochem. 72:2264-71), glial-cell line derived neurotrophic factor (GDNF) (Miyazaki, H. et al. (1999) Neuroscience 89:643-7), activity-dependant neurotrophic factor (ADNF) (Zamostiano, R. et al. (1999) Neurosci Letter 264:9-12), cytokine leukemia inhibiting factor (LIF) (Blesch, A. et al. (1999) J. Neurosci. 19:3356-66), oncostatin M, interleukin, and the insulin-like growth factors 1 and 2.

Other forms of neuroprotective therapeutic agents include, for example, Clomethiazole (Zendra) (Marshal, J. W. et al. (1999) Exp. Neurol. 156:121-9); kynurenic acid (KYNA) (Salvati, P. et al. (1999) Prog Neruopsychopharmacol Biol Psychiatry 23:741-52), Semax (Miasoedova, N. F. et al. (1999) Zh Nevrol Psikhiatr Imss Korsakova 99:15-19), FK506 (tacrolimus) (Gold, B. G. et al. (1999) J. Pharmacol. Exp. Ther. 289:1202-10), L-threo-1-phenyl-2-decanoylamino-3-morpholino-1-propanol (Inokuchi, J. et al. (1998) Act Biochim Pol 45:479-92), andrenocorticotropin-(4-9) analoge (ORG 2766) and dizolcipine (MK-801) (Herz, R. C. et al. (1998) Eur J. Pharmacol 346:159-65), cerebral interleukin-6) (Loddick, S. A. et al. (1998) J. Cereb Blood Flow Metab 18:176-9), selegiline (Semkova, I. et al. (1996) Eur J. Pharmacol 315:19-30), MK-801 (Barth, A. et al. (1996) Neuro Report 7:1461-4; glutamate antagonist such as, NPS1506, GV1505260, MK801 (Baumgartner, W. A. et al. (1999) Ann Thorac Surg 67:1871-3), GV150526 (Dyker, A. G. et al. (1999) Stroke 30:986-92); AMPA antagonist such as NBQX (Baumgartner, W. A. (1999) et al Ann Thorac Surg 67:1871-3, PD152247 (PNQX) (Schielke, G. P. et al. (1999) Stroke 30:1472-7), SPD 502 (Nielsen, E. O. et al. (1999) J. Pharmacol Exp Ther 289:1492-501), LY303070 and LY300164 (May, P. C. et al. (1999) Neuroscience Lett 262:219-221).

When the steroid analogues of the present invention are administered in combination or alternation with other pharmaceutically active agents, (i.e., other neuroprotective agents) even less of the steroid analogue may be therapeutically effective. The steroid analogue may be administered once or several times a day. The duration of the treatment may be once per day for a period of from two to three weeks and may continue for a period of months or even years. The daily dose can be administered either by a single dose in the form of an individual dosage unit or several smaller dosage units or by multiple administration of subdivided dosages at certain intervals.

For example, a dosage unit can be administered from 0 hours to 1 hr, 1 hr to 24 hr or 24 hours to at least 100 hours post injury. Alternatively, the dosage unit can be administered from about 0.5, 1, 2, 3, 4, 5, 6, 7, 8, 9, 10, 11, 12, 13, 14, 15, 16, 17, 18, 19, 20, 21, 22, 23, 24, 30, 40, 48, 72, 96, 120 hours or longer post injury. Subsequent dosage units can be administered any time following the initial administration such that a therapeutic effect is achieved. For instance, additional dosage units can be administered to protect the subject from the secondary wave of edema that may occur over the first several days post-injury.

In combination therapy, effective dosages of two or more agents are administered together, whereas during alternation therapy an effective dosage of each agent is administered serially. The dosages will depend on absorption, inactivation and excretion rates of the drug as well as other factors known to those of skill in the art. It Dosage values will also vary with the severity of the condition to be alleviated. For any particular subject, specific dosage regimens and schedules should be adjusted over time according to the individual need and the professional judgment of the person administering or supervising the administration of the compositions.

When the compounds or compositions of the present invention are administered in combination or alternation with other pharmaceutically active agents, (i.e., other neuroprotective agents) a lower level of the steroid analog in certain embodiments may be used. The compositions may be administered once or several times a day. The duration of the treatment may be once per day for a period of from two to three weeks and may continue for a period of months or even years. The daily dose can be administered either by a single dose in the form of an individual dosage unit or several smaller dosage units or by multiple administration of subdivided dosages at certain intervals.

For example, a dosage unit can be administered from 0 hours to 1 hr, 1 hr to 24 hr or 24 hours to at least 100 hours post injury. Alternatively, the dosage unit can be administered from about 0.5, 1, 2, 3, 4, 5, 6, 7, 8, 9, 10, 11, 12, 13, 14, 15, 16, 17, 18, 19, 20, 21, 22, 23, 24, 30, 40, 48, 72, 96, 120 hours or longer post injury. Subsequent dosage units can be administered any time following the initial administration such that a therapeutic effect is achieved. For instance, additional dosage units can be administered to protect the subject from the secondary wave of edema that may occur over the first several days post-injury.

In combination therapy, effective dosages of two or more agents are administered together, whereas during alternation therapy an effective dosage of each agent is administered serially. The dosages will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

The efficacy of a drug can be prolonged, augmented, or restored by administering the compound in combination or alternation with a second, and perhaps third, agent. Alternatively, the pharmacokinetics, biodistribution or other parameter of the drug can be altered by such combination or alternation therapy. In general, combination therapy is typically preferred over alternation therapy because it induces multiple simultaneous stresses on the condition.

In another embodiment, the active compound is administered in combination or alternation with one or more other non-steroidal anti-inflammatory drug(s) (NSAIDS). Examples of NSAIDS that can be used in alternation or combination therapy are carboxylic acids, propionic acids, fenamates, acetic acids, pyrazolones, oxicans, alkanones, gold compounds and others that inhibit prostaglandin synthesis, preferably by selectively inhibiting cylcooxygenase-2 (COX-2). Some nonlimiting examples of COX-2 inhibitors are Celebrex (celecoxib) and Vioxx (rofacoxib). Some non-limiting examples of NSAIDS are aspirin (acetylsalicylic acid), Dolobid (diflunisal), Disalcid (salsalate, salicylsalicylate), Trisilate (choline magnesium trisalicylate), sodium salicylate, Cuprimine (penicillamine), Tolectin (tolmetin), ibuprofen (Motrin, Advil, Nuprin Rufen), Naprosyn (naproxen, Anaprox, naproxen sodium), Nalfon (fenoprofen), Orudis (ketoprofen), Ansaid (flurbiprofen), Daypro (oxaprozin), meclofenamate (meclofanamic acid, Meclomen), mefenamic acid, Indocin (indomethacin), Clinoril (sulindac), tolmetin, Voltaren (diclofenac), Lodine (etodolac), ketorolac, Butazolidin (phenylbutazone), Tandearil (oxyphenbutazone), piroxicam (Feldene), Relafen (nabumetone), Myochrysine (gold sodium thiomalate), Ridaura (auranofin), Solganal (aurothioglucose), acetaminophen, colchicine, Zyloprim (allopurinol), Benemid (probenecid), Anturane (sufinpyrizone), Plaquenil (hydroxychloroquine), Aceclofenac, Acemetacin, Acetanilide, Actarit, Alclofenac, Alminoprofen, Aloxiprin, Aluminium Aspirin, Amfenac Sodium, Amidopyrine, Aminopropylone, Ammonium Salicylate, Ampiroxicam, Amyl Salicylate, Anirolac, Aspirin, Auranofin, Aurothioglucose, Aurotioprol, Azapropazone, Bendazac (Bendazac Lysine), Benorylate, Benoxaprofen, Benzpiperylone, Benzydamine hydrochloride, Bomyl Salicylate, Bromfenac Sodium, Bufexamac, Bumadizone Calcium, Butibufen Sodium, Capsaicin, Carbaspirin Calcium, Carprofen, Chlorthenoxazin, Choline Magnesium Trisalicylate, Choline Salicylate, Cinmetacin, Clofexamide, Clofezone, Clometacin, Clonixin, Cloracetadol, Cymene, Diacerein, Diclofenac (Diclofenac Diethylammonium Salt, Diclofenac Potassium, Diclofenac Sodium), Diethylamine Salicylate, Diethylsalicylamide, Difenpiramide, Diflunisal, Dipyrone, Droxicam, Epirizole, Etenzamide, Etersalate, Ethyl Salicylate, Etodolac, Etofenamate, Felbinac, Fenbufen, Fenclofenac, Fenoprofen Calcium, Fentiazac, Fepradinol, Feprazone, Floctafenine, Flufenamic, Flunoxaprofen, Flurbiprofen (Flurbiprofen Sodium), Fosfosal, Furprofen, Glafenine, Glucametacin, Glycol Salicylate, Gold Keratinate, Harpagophytum Procumbens, Ibufenac, Ibuprofen, Ibuproxam, Imidazole Salicylate, Indomethacin (Indomethacin Sodium), Indoprofen, Isamifazone, Isonixin, Isoxicam, Kebuzone, Ketoprofen, Ketorolac Trometamol, Lithium Salicylate, Lonazolac Calcium, Lomoxicam, Loxoprofen Sodium, Lysine Aspirin, Magnesium Salicylate, Meclofenamae Sodium, Mefenamic Acid, Meloxicam, Methyl Butetisalicylate, Methyl Gentisate, Methyl Salicylate, Metiazinic Acid, Metifenazone, Mofebutazone, Mofezolac, Morazone Hydrochloride, Morniflumate, Morpholine Salicylate, Nabumetone, Naproxen (Naproxen Sodium), Nifenazone, Niflumic Acid, Nimesulide, Oxametacin, Oxaprozin, Oxindanac, Oxyphenbutazone, Parsalmide, Phenybutazone, Phenyramidol Hydrochloride, Picenadol Hydrochloride, Picolamine Salicylate, Piketoprofen, Pirazolac, Piroxicam, Pirprofen, Pranoprofen, Pranosal, Proglumetacin Maleate, Proquazone, Protizinic Acid, Ramifenazone, Salacetamide, Salamidacetic Acid, Salicylamide, Salix, Salol, Salsalate, Sodium Aurothiomalate, Sodium Gentisate, Sodium Salicylate, Sodium Thiosalicylate, Sulindac, Superoxide Dismutase (Orgotein, Pegorgotein, Sudismase), Suprofen, Suxibuzone, Tenidap Sodium, Tenoxicam, Tetrydamine, Thurfyl Salicylate, Tiaprofenic, Tiaramide Hydrochloride, Tinoridine Hydrochloride, Tolfenamic Acid, Tometin Sodium, Triethanolamine Salicylate, Ufenamate, Zaltoprofen, Zidometacin and Zomepirac Sodium.

VI. Pharmaceutical Compositions

The described compounds can be formulated as pharmaceutical compositions and administered for the treatment or prevention of CNS injury from trauma or disease, and in particular for injury resulting from traumatic brain injury or stroke. The compositions can be administered in any of a variety of forms adapted to the chosen route of administration, including systemically, such as orally, or parenterally, by intravenous, intramuscular, topical, transdermal or subcutaneous routes.

The compound can be included in the pharmaceutically acceptable carrier or diluent in an amount sufficient to deliver to a patient a therapeutically effective amount of compound to treat traumatic CNS injury in vivo without causing serious toxic effects in the patient treated.

The steroid analogues used in the methods of the invention may further comprise an inorganic or organic, solid or liquid, pharmaceutically acceptable carrier. The carrier may also contain preservatives, wetting agents, emulsifiers, solubilizing agents, stabilizing agents, buffers, solvents and salts. Compositions may be sterilized and exist as solids, particulants or powders, solutions, suspensions or emulsions.

The steroid analogues can be formulated according to known methods to prepare pharmaceutically useful compositions, such as by admixture with a pharmaceutically acceptable carrier vehicle. Suitable vehicles and their formulation are described, for example, in Remington: The Science and Practice of Pharmacy, 21st ed, Lippincott Williams & Wilkins (2005 ( ). In order to form a pharmaceutically acceptable composition suitable for effective administration, such compositions will contain an effective amount of the steroid analogue, either alone, or with a suitable amount of carrier vehicle.

The pharmaceutically acceptable carrier of the present invention will vary depending on the method of drug administration. The pharmaceutical carrier employed may be, for example, either a solid, liquid, or time release. Representative solid carriers are lactose, terra alba, sucrose, talc, geletin, agar, pectin, acacia, magnesium stearate, stearic acid, microcrystallin cellulose, polymer hydrogels, and the like. Typical liquid carriers include syrup, peanut oil, olive oil, cyclodextrin, and the like emulsions. Those skilled in the art are familiar with appropriate carriers for each of the commonly utilized methods of administration. Furthermore, it is recognized that the total amount of steroid analogue administered as a therapeutic effective dose will depend on both the pharmaceutical composition being administered (i.e., the carrier being used) and the mode of administration.

In one embodiment, a steroid analogue, pharmaceutically acceptable salt, ester or prodrug thereof, is administered via parenteral administration in a dose of about 0.1 ng to about 100 g per kg of body weight, about 10 ng to about 50 g per kg of body weight, from about 100 ng to about 1 g per kg of body weight, from about 1 μg to about 100 mg per kg of body weight, from about 1 μg to about 50 mg per kg of body weight, from about 1 mg to about 500 mg per kg of body weight; and from about 1 mg to about 50 mg per kg of body weight. Alternatively, the amount of steroid analogue administered to achieve a therapeutic effective dose is about 0.1 ng, 1 ng, 10 ng, 100 ng, 1 μg, 10 μg, 100 μg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

In certain embodiments, the compounds described herein are compounded with a suitable pharmaceutically acceptable carrier in a unit dosage form. A unit dosage form, such as a preselected amount of liquid composition, can, for example, contain the compound in amounts ranging from about 5 to about 1000 mg, or from about 250 to about 750 mg. Expressed in proportions, the active compound is generally present in from about 10 to about 750 mg/ml of carrier. Liquid formulations of steroid analogs can comprise about 1-100 mg/ml of vehicle. In the case of compositions containing supplementary active ingredients, the dosages are determined by reference to the usual dose and manner of administration of the said ingredients.

The active ingredients can exhibit activity, particularly in treatment or prevention of secondary reactions from brain injuries such as TBI or stroke when administered in amounts ranging from about 0.1 mg to about 100 mg per kilogram of body weight per day. A preferred dosage regimen for optimum results would be from about 0.5 mg to about 50 mg per kilogram of body weight per day, and such dosage units are employed that a total of from about 0.25 gram to about 3.0 grams of the active compound for a subject of about 70 kg of body weight are administered in a 24-hour period. This dosage regimen may be adjusted to provide the optimum therapeutic response and can be administered one to three times a day in dosages of about 600 mg per administration. For example, several divided doses may be administered daily or the dose may be proportionally reduced as indicated by the exigencies of the therapeutic situation.

In one embodiment of the present invention, the neuroprotective steroid is administered once or several times a day. The duration of the treatment may be once per day for a period of about 1, 2, 3, 4, 5, 6, 7 days or more. The daily dose can be administered either by a single dose in the form of an individual dosage unit or several smaller dosage units or by multiple administration of subdivided dosages at certain intervals. For instance, a dosage unit can be administered from about 0 hours to about 1 hr, about 1 hr to about 24 hr, about 1 to about 72 hours, about 1 to about 120 hours, or about 24 hours to at least about 120 hours post injury. Alternatively, the dosage unit can be administered from about 0.5, 1, 2, 3, 4, 5, 6, 7, 8, 9, 10, 11, 12, 13, 14, 15, 16, 17, 18, 19, 20, 21, 22, 23, 24, 30, 40, 48, 72, 96, 120 hours or longer post injury. The duration of the constant dosing regimen is about 12, 24, 36, 60, 72, 84, or 120 hours or about 1 to 24 hours, about 12 to 36 hours, about 24 to 48 hours, about 36 to 60 hours, about 48 to 72 hours, about 60 to 96 hours, about 72 to 108 hours, about 96 to 120 hours, or about 108 to 136 hours. Subsequent dosage units can be administered any time following the initial administration such that a therapeutic effect is achieved. For instance, additional dosage units can be administered to protect the subject from the secondary wave of edema that may occur over the first several days post-injury. In specific embodiments, the subject undergoing the therapy with is administered a constant neuroprotective steroid dosing regimen. By "constant dosing regimen" is intended the subject undergoing therapy is administered a constant total hourly infusion dose over the course of treatment.

Administration of the steroid analogues of the invention may be performed by many methods known in the art. The present invention comprises all forms of dose administration including, but not limited to, systemic injection, parenteral administration, intravenous, intraperitoneal, intramuscular, transdermal, buccal, subcutaneous and intracerebroventricular administration. Alternatively, the steroid analogue may be administered directly into the brain or cerebrospinal fluid by any intracerebroventricular technique including, for example, lateral cerebro ventricular injection, lumbar puncture or a surgically inserted shunt into the cerebro ventricle of a patient. Methods of administering may be by dose or by control release vehicles.

If administered intravenously, preferred carriers are physiological saline or phosphate buffered saline (PBS).

While the methods of the invention are not bound by any theory, it is believed that a traumatic CNS injury, may make the blood/brain barrier more permeable allowing entry of large molecules that would not normally cross the blood/brain barrier to enter the cerebral spinal fluid. For examples of intravenous, intraperitoneal, intramuscular, and subcutaneous administration of neurotrophic agents to treat CNS injuries see, for example, U.S. Pat. No. 5,733,871 and WO 97/21449, both of which are herein incorporated by reference.

Additional pharmaceutical methods may be employed to control the duration of action. Controlled release preparations may be achieved by the use of polymers to complex or absorb the steroid analogue. The controlled delivery may be exercised by selecting appropriate macromolecules (for example, polyesters, polyamino acids, polyvinyl pyrrolidone, ethylene-vinylacetate, methylcellulose, carboxymethylcellulose, or protamine sulfate). The rate of drug release may also be controlled by altering the concentration of such macromolecules.

Another possible method for controlling the duration of action comprises incorporating the therapeutic agents into particles of a polymeric substance such as polyesters, polyamino acids, hydrogels, poly(lactic acid) or ethylene vinylacetate copolymers. Alternatively, it is possible to entrap the therapeutic agents in microcapsules prepared, for example, by coacervation techniques or by interfacial polymerization, for example, by the use of hydroxymethyl cellulose or gelatin-microcapsules or poly(methylmethacrylate) microcapsules, respectively, or in a colloid drug delivery system, for example, liposomes, albumin, microspheres, microemulsions, nanoparticles, nanocapsules, or in macroemulsions. Such teachings are disclosed in Remington's Pharmaceutical Sciences (1980). Ideally the compounds should be administered to achieve peak plasma concentrations of the active compound of from about 0.2 to 70 µM, preferably about 1.0 to 10 µM. This may be achieved, for example, by the intravenous injection of an appropriate concentration of the active ingredient, optionally in saline, or administered as a bolus of the active ingredient.

The concentration of the compounds in the drug composition will depend on absorption, inactivation and excretion rates of the extract as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The compounds may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compounds can be administered as a component of an elixir, suspension, syrup, wafer, chewing gum or the like. A syrup may contain, in addition to the active compounds, sucrose as a sweetening agent and certain preservatives, dyes and colorings and flavors. The compounds can also be mixed with other active materials that do not impair the desired action, or with materials that supplement the desired action, such as antibiotics, antifungals, anti-inflammatories, or other anti-autoimmune compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

Formulations suitable for parental administration conveniently comprise a sterile aqueous preparation of the active compound, which can be isotonic with the blood of the recipient.

Nasal spray formulations comprise purified aqueous solutions of the active agent with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media such as mineral oil, petroleum, polyhydroxy alcohols or other bases used for topical formulations. The addition of other accessory ingredients as noted above may be desirable.

Further, the present invention provides liposomal formulations of the steroid analogues, salts, esters and prodrugs thereof. The technology for forming liposomal suspensions is well known in the art. When the steroid analogue or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer that forms the structure of the liposome. In either instance, the liposomes that are produced may be reduced in size, as through the use of standard sonication and homogenization techniques. The liposomal formulations containing the progesterone analogue or salts thereof, may be lyophilized to produce a lyophilizate which may be reconstituted with a pharmaceutically acceptable carrier, such as water, to regenerate a liposomal suspension.

Pharmaceutical formulations are also provided which are suitable for administration as an aerosol, by inhalation. These formulations comprise a solution or suspension of the desired steroid analogue or a salt thereof or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts.

In another embodiment, the compounds are prepared with carriers that will protect them against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art.

VII. Synthesis of the Active Compounds

General schemes 1-8 below describe the preparation of selected steroid analogues. It is understood that the specific synthetic steps are not limited to the reactions shown in the schemes and that many alternative reaction sequences known in the art are suitable for the preparation of the analogues. Furthermore, it is understood that any naturally occurring or synthetic amino acid in the D, L or D,L configuration may be used. The invention is not limited by the type of protecting group and any suitable protecting group may be used. Protecting groups for amino groups and ketone groups are well known in the art and described by Greene et al. "Protective Groups in Organic Synthesis," John Wiley and Sons, 4$^{th}$ edition, 2007.

Progesterone Analogues Substituted at the 3-Position:

Compounds derivatized at the 3-position of the steroid ring system to comprise an ester of an amino acid may be prepared using the general process described in Scheme 1 below. Starting from progesterone, the carbonyl group at the 3-position is selectively reduced to produce the allylic alcohol 2. One example of a selective reduction is the Luche Reduction which use sodium borohydride and cerium trichloride in methanol (see Luche, J.-L. *J. Am. Chem. Soc.*, 1978, 100, 2226). Typically, the reduction is run at low temperature to avoid over-reduction of the C-20 carbonyl. Alcohol 2 is then esterified with a suitable amino acid derivative form the progesterone analogue 3. The protecting group is removed and a suitable salt, such as an HCl salt, may be formed, if desired.

Scheme 1

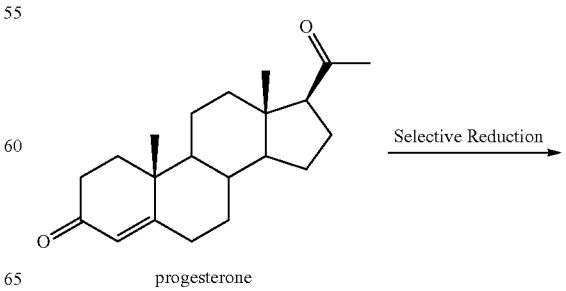

progesterone

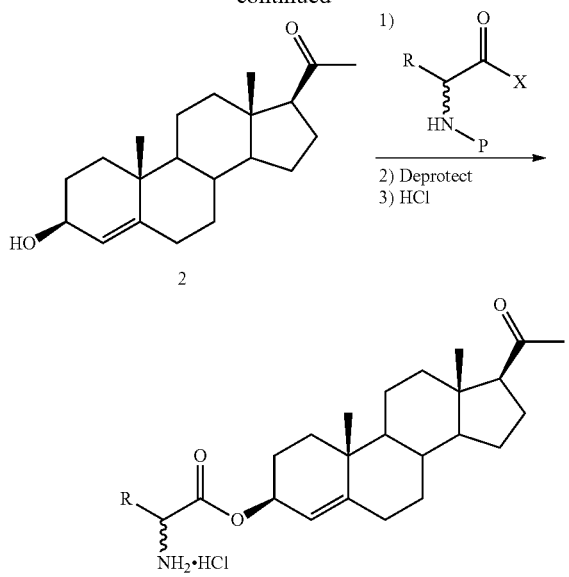

R = amino acid side chain
P = protecting group
X = leaving group

In one embodiment, the ester bond may be formed by reaction of the hydroxyl group of 2 with a protected amino acid acyl halide, where X is chloro, bromo, iodo or fluoro. In another embodiment, the ester bond may be formed by reacting the hydroxyl group with an activated carboxylic acid, where X is an activated leaving group. Many reagents are known that will activate carboxyl groups to react with nucleophiles. For example, a variety of peptide coupling reagents well known in the art are used to activate carboxyl groups in-situ to react with amino groups of amino acids to form peptide bonds. These reagents can also activate carboxylic acids to form reactive intermediates that will react with hydroxy groups on the steroid compound. Non-limiting examples of the carboxyl activating groups include carbodiimide reagents, phosphonium reagents such as benzotriazolyloxy-tris-(dimethylamino) phosphonium hexafluorophosphate (BOP) and the like, uronium or carbonium reagents such as O-(benzotriazol-1-yl)-N,N,N',N'-tetramethyluronium hexafluorophosphate (HBTU), benzotriazol-1-yl-oxy-tripyrrolidinophosphonium hexafluorophosphate (PyBOP) and the like; 1-ethoxycarbonyl-2-ethoxy-1,2-dihydroqunoline (EEDQ); 1-methyl-2-chloropyridinium iodide (Muikaiyama's reagent) and the like. In other embodiments, the ester may be formed by trans-esterification of another ester group including active esters such as a p-nitrophenyl ester, a pentafluorophenylester, an N-hydroxysuccinimidyl ester, a 1-hydroxybenzotriazolyl ester and the like. An acyl azide group may also be used to form the ester bond. In another embodiment, the ester may also be formed by reaction of the hydroxy with a symmetric or mixed anhydride (X is RC(O)O—). Catalysts such as 4-dimethylaminopyridine (DMAP) and the like may be used to facilitate the ester formation.

Progesterone Analogues Substituted at the 20-Position:

Scheme 2 below illustrates the general synthetic process for the formation of steroid analogues that comprise amino acid residues at the 20-position of the ring. In this process, progesterone is reduced to the diol using a strong reducing reagent, such as lithium aluminum hydride. The allylic hydroxyl group is then selectively oxidized to produce the enone 4, with the C-20 hydroxyl group intact. Any suitable oxidizing agent that will selectively oxidize an allylic alcohol may be used. One non-limiting example is manganese dioxide ($MnO_2$). The resulting alcohol 3 is then esterified to produce the desired steroid analogue 5 comprising an amino acid residue at the 20-position. As described above for Scheme 1, the esterification reaction may be accomplished with a variety of reagents, including a protected amino acid halide or with a protected amino acid using a coupling reagent known in the art to activate carboxylate groups.

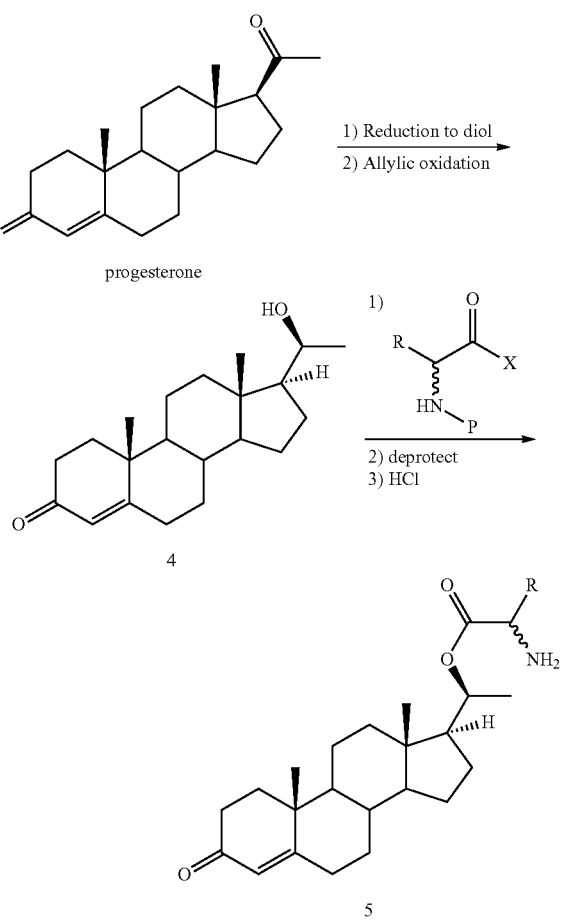

R = amino acid side chain
P = protecting group
X = leaving group

C-3 Progesterone —C=NR Derivatives

Scheme 3 below illustrates the preparation of an analogue of Formula VII, substituted at C-3 with the group =N—$R^3$ where $R^3$ is —$OR^{11}$, and $R^{11}$ is an amino acid residue. The C20 carbonyl is first protected with a suitable protecting group such as the cyclic ketal 6 to prevent reaction with the nucleophilic hydroxylamine. The remaining enone is reacted with hydroxylamine to produce a mixture of E/Z 7a and 7b. The E-oxime 7a is then esterified with a suitably protected amino acid halide or using a protected amino acid with a coupling reagent as described above for Scheme 1 to produce the E-isomer of protected analogue 8a. Removal of the cyclic acetal under acidic conditions followed by removal of the amino protecting group under typically basic conditions provides the C3 analogue 9a, which is converted to the hydrochloride salt upon treatment with HCl. The corresponding Z-isomers 8b and 9b are prepared using Z-oxime 7b in the same manner.

Scheme 3

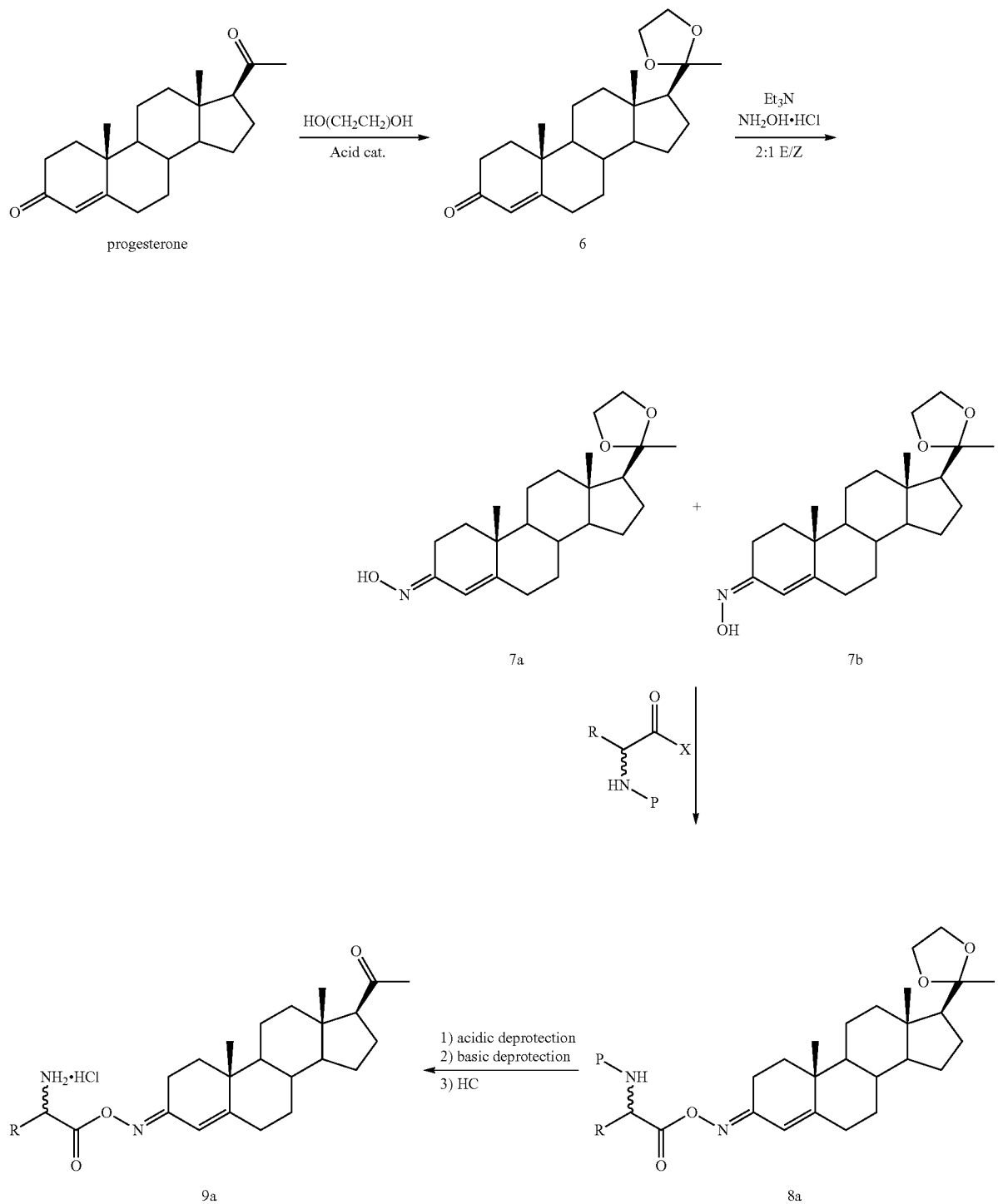

R = amino acid side chain
P = amino protecting group
X = leaving group

Scheme 4 shows the general synthesis of an analogue of Formula IV substituted at C-3 with the group $R^5$—N═C where $R^5$ is R—NH—, and R is an amino acid residue. Starting from protected intermediate 6, the C-3 carbonyl is reacted with hydrazine to produce the hydrazone 10. The hydrazone is then reacted with a suitable reactive amino acid derivative as described above for Scheme 1 to yield the hydrazide 11. The hydrazide may be converted to a pharmaceutically acceptable salt by treatment with a pharmaceutically acceptable acid, such as HCl.

Scheme 4

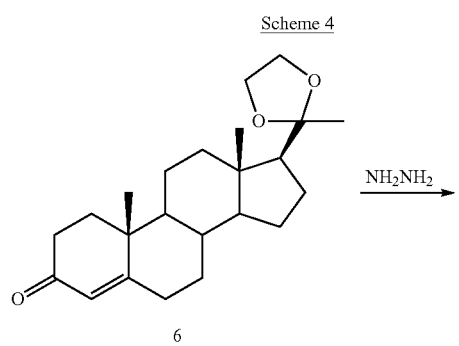

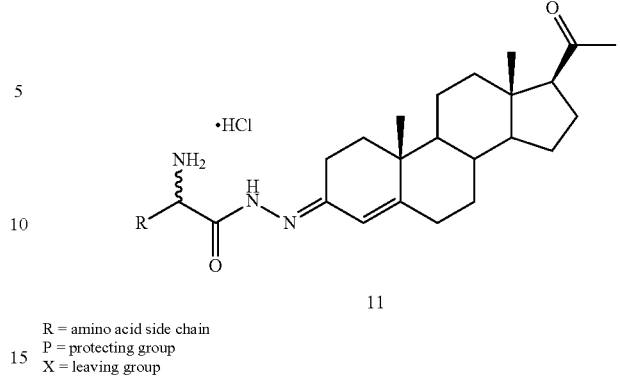

R = amino acid side chain
P = protecting group
X = leaving group

C-3 Pregnanolone and Allopregnanolone Derivatives

Scheme 5 below shows the preparation of allopregnanolone (ALLO) analogues substituted at C-3 with an amino acid residue. Pregnenolone is first reduced with hydrogen catalyzed by palladium on carbon to produce compound 12 in the 3-beta, 5-alpha configuration. Compound 12 is then esterified as described for Scheme 1 above with a reactive protected amino acid reagent followed by deprotection to produce compound 13 substituted at the C-3 position with an amino acid residue. The HCl salt is formed by treatment with HCl as before.

To produce compound 15, in which the amino acid substituent has the opposite stereoisomeric configuration at C-3, the stereo configuration of the hydroxyl group in compound 12 is inverted using Mitsunobu conditions (see Mitsunobu et al., *Bull. Chem. Soc. Japan* 1967, 40, 2380-2382 and Mitsunobu et al., *Synthesis* 1981, 1-28 and Castro et al., *Org. React.* 1983, 29, 1) to form compound 14 with the 3-alpha, 5-alpha configuration. Compound 14 is esterified as described above to produce compound 15 with the 3-alpha, 5-alpha configuration, followed by treatment with HCl to form the salt.

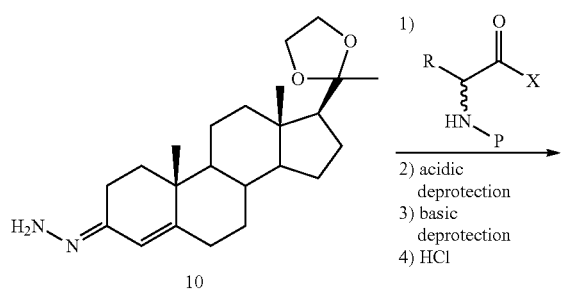

Scheme 5

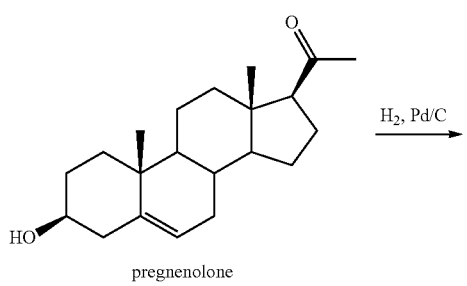

pregnenolone

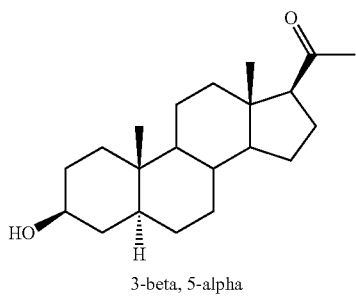

3-beta, 5-alpha
12

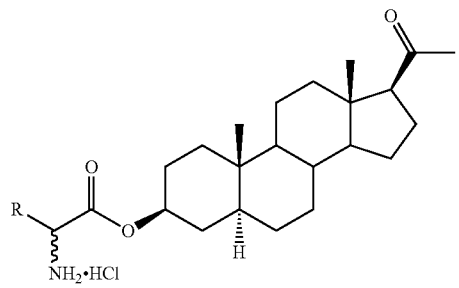

13

Inversion of stereochemistry
Mitsunobu conditions

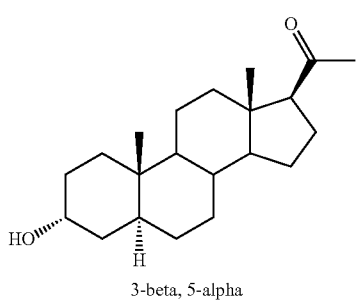

3-beta, 5-alpha
14

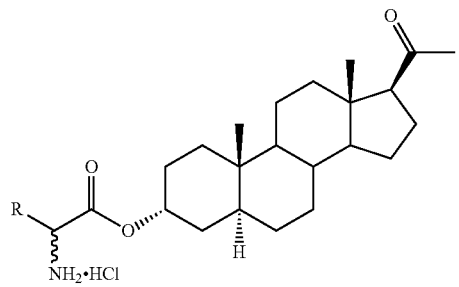

15

R = amino acid side chain
P = protecting group
X = leaving group

Scheme 6 below shows a general process for the preparation of C-3 substituted pregnanolone analogues in different stereoisomeric configurations. Starting from progesterone, reduction of the enone with hydrogen under palladium on carbon forms compound 16. Reduction of the cyclic ketone, using a suitable reducing agent such as sodium borohydride, forms a mixture of alcohols 17a and 17b. Esterification of alcohols 17a and 17b followed by removal of the protecting group and salt formation provides pregnanolone analogues 18a and 18b.

Scheme 6

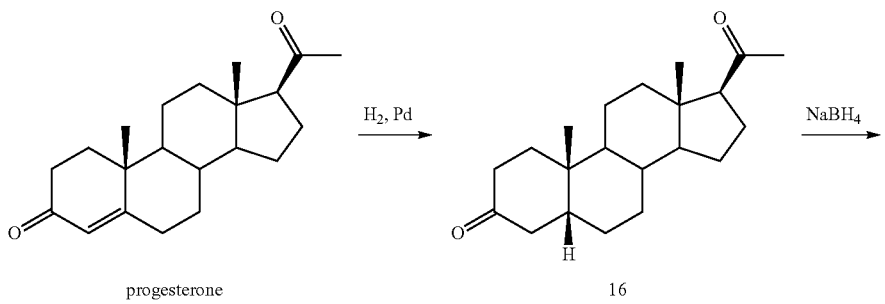

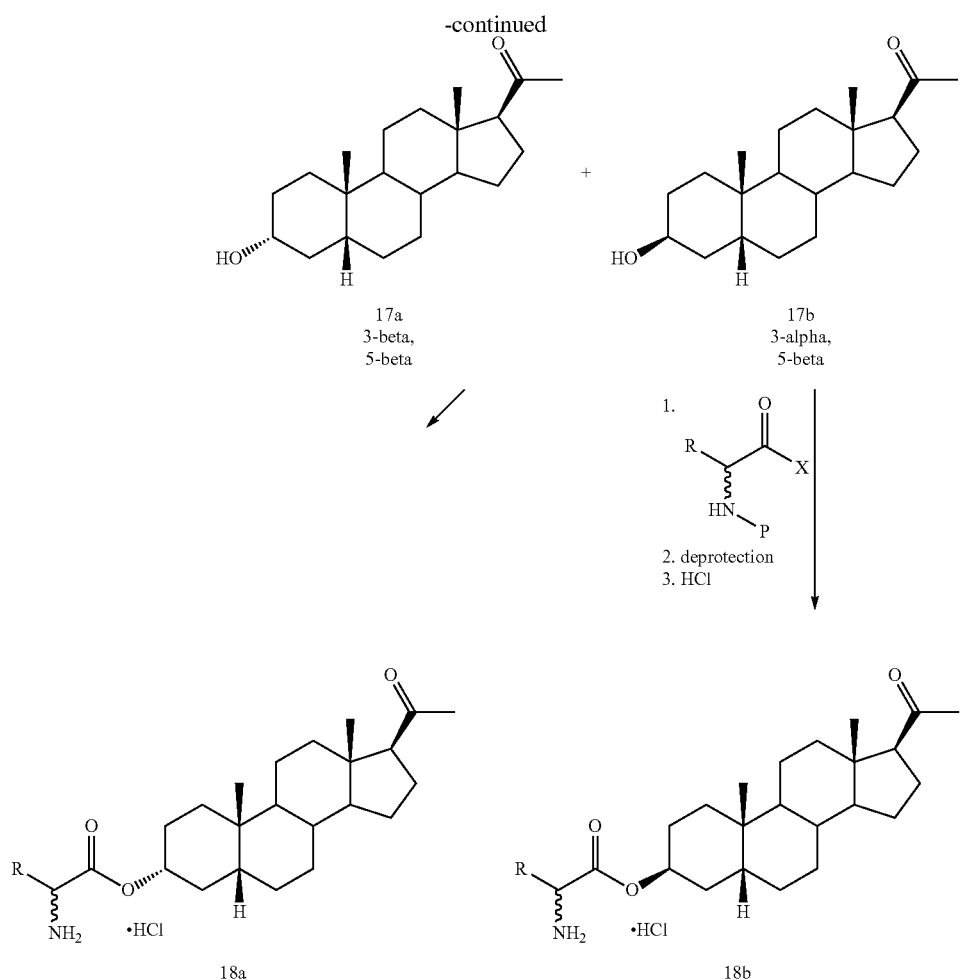
R = amino acid side chain
P = protecting group
X = leaving group
Steroid analogues with a double bond between the C5 and C6 positions may be prepared according to the general process shown in Scheme 7 below.
Scheme 7
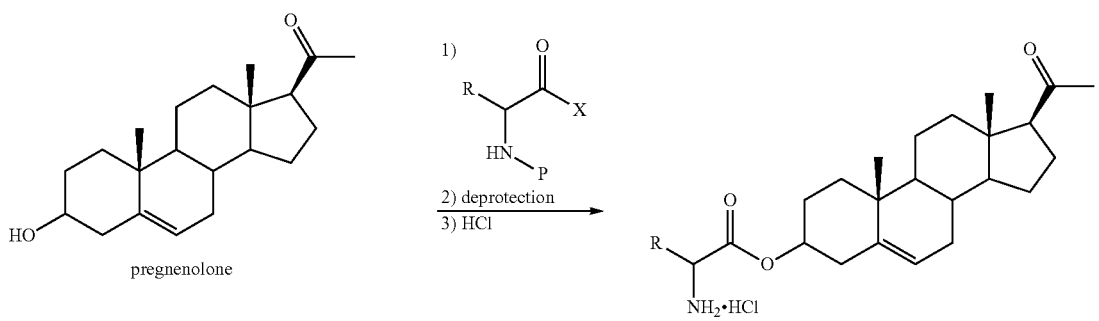

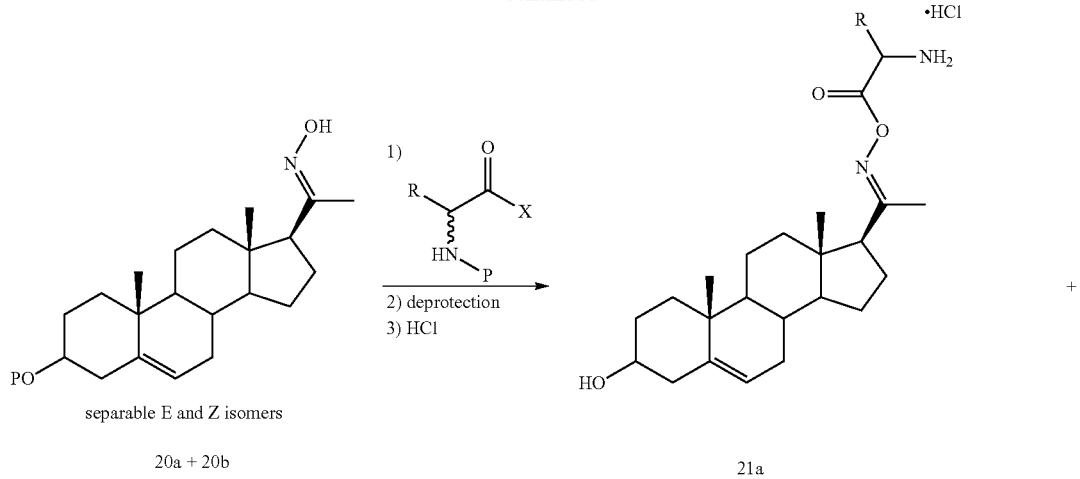

20a + 20b

21a

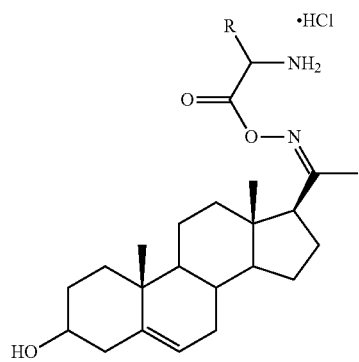

21a

R = amino acid side chain
P = protecting group
X = leaving group

Esterification of pregnenolone with a suitably protected amino acid as described for scheme 1 above provides compound 19, with an amino acid residue at the 3-position. Protection of the hydroxyl of pregnenolone followed by reaction with hydroxylamine provides the E- and Z-isomers 20a and 20 b. If desired, the isomers may be separated at this stage. Reaction of 20a and 20b with a suitably protected amino acid, followed by deprotection and treatment with HCl provides compounds 21a and 21b.

Modification of the process shown in Scheme 7 leads to related compounds with a double bond between C5 and C6. For example, to obtain the steroid analogues corresponding to compounds 21a and 21b in which the C-3 hydroxyl is in the ketone oxidation state, compounds 20a and 20b may be deprotected to the alcohol and oxidized to form the ketone prior to reaction with the activated amino acids reagent. Reduction of compound 19 will provide the corresponding C20 alcohol, which may be esterified as described above to form an analogue substituted at both C3 and C20 positions.

Reduction of protected pregnenolone followed by esterification of the resulting C20 hydroxyl group with a suitably protected activated amino acid will provide the C20 amino acid substituted derivative after removal of the protecting group.

Protection of the C20 ketone, for example as a cyclic ketal, followed by oxidation of the C3 hydroxyl to the corresponding ketone and then reaction with hydroxylamine will provide the corresponding C3 oximes, which can be reacted with suitably protected activated amino acids to prepare the =N—NR$^{11}$R$^{12}$ compounds.

Analogues with a double bond between the C1 and C2 carbons may be prepared according to the process depicted in Scheme 8 below.

Scheme 8

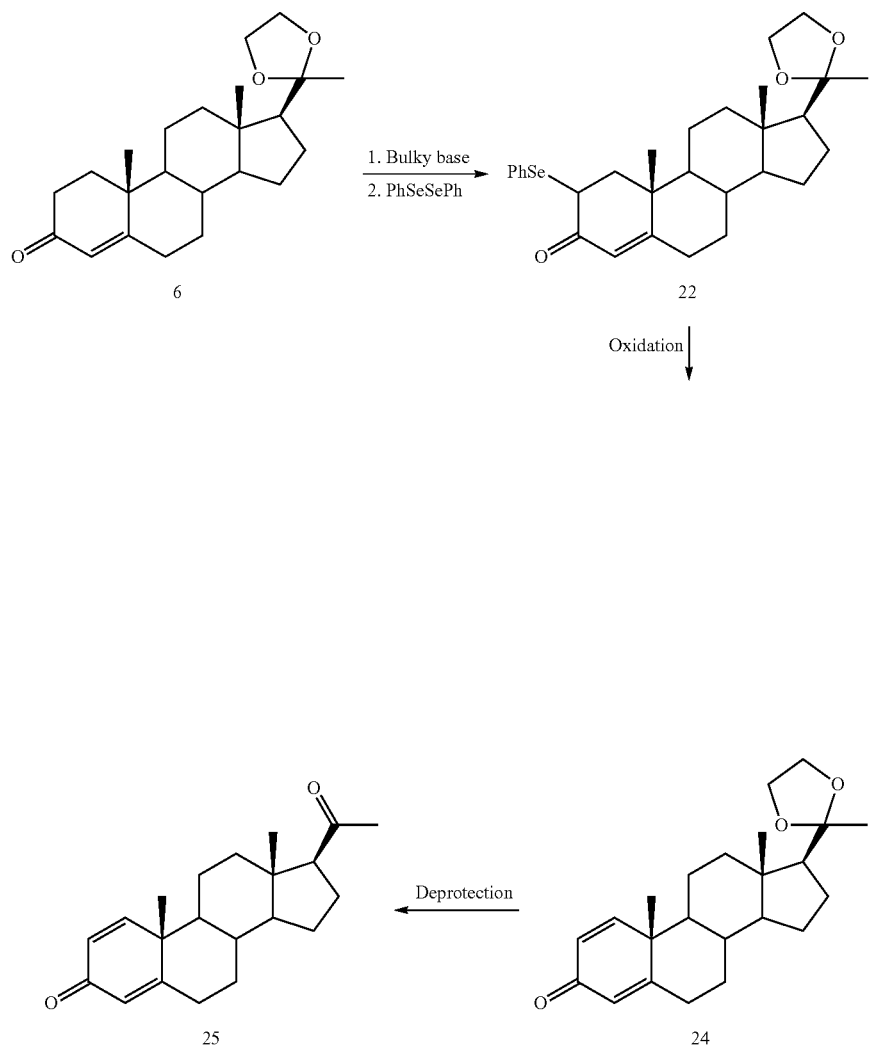

Starting from protected compound 6, treatment with a bulky base such as lithium diisopropylamide (LDA) or the like, to form the enolate species, followed by reaction with a suitable source of electrophilic selenium, such as diphenyldiselenide, provides compound 22. Treatment of compound 22 with a suitable oxidizing agent, such as hydrogen peroxide, provides compound 24, which is deprotected to provide compound 25.

Enantiomeric Progesterone Compounds

In one embodiment, the invention provides enantiomeric progesterone and neuroprotective steroid compounds. The enantiomer of progesterone (ent-PROG) has shown similar efficacy to progesterone and allopregnanolone across several measures relevant to neuroprotection, including the reduction of cerebral edema, reduction of pro-inflammatory cytokine expression, and reduction in proapoptotic p53 protein expression. Ent-PROG treatment was also shown to result in significantly increased glutathione reductase activity, a measure of its potential to minimize oxidative stress following TBI, relative to both progesterone and allopregnanolone. Although it binds with moderate affinity to the classical progesterone receptor (PR), ent-PROG does not activate PR-mediated gene transcription. Thus it is thought that ent-PROG is able to achieve its neuroprotective effects either through transcription-independent PR-mediated signaling or via PR-independent pathways. In light of these findings, and with the goal of providing a compound of improved efficacy relative to PROG or allopregnanolone, the development of a complementary set of ent-PROG based analogue compounds was pursued.

Addition of methyl vinyl ketone (MVK) to 2-methyl-1,3-cyclopentadione (37, Scheme 9) gave the triketone 38. The organocatalyst D-proline was then used in order to achieve asymmetric cyclization of 38 to give the Hajos-Parrish ketone (39). Sodium borohydride reduction of 39 was followed by protection of the newly formed secondary alcohol 40 as its tert-butyl ether (41). Introduction of an α-methylene group was achieved through initial carbonation of 41 with Stiles' reagent, methyl magnesium carbonate (MMC), in DMF. Selective reduction of the C-4-C-5 double bond of compound 43 was immediately followed by decarboxylation of the unstable saturated intermediate 44 to give the enone 45 with trans ring junction.

Scheme 9. Synthesis of enone 45, CD ring fragment of ent-PROG.

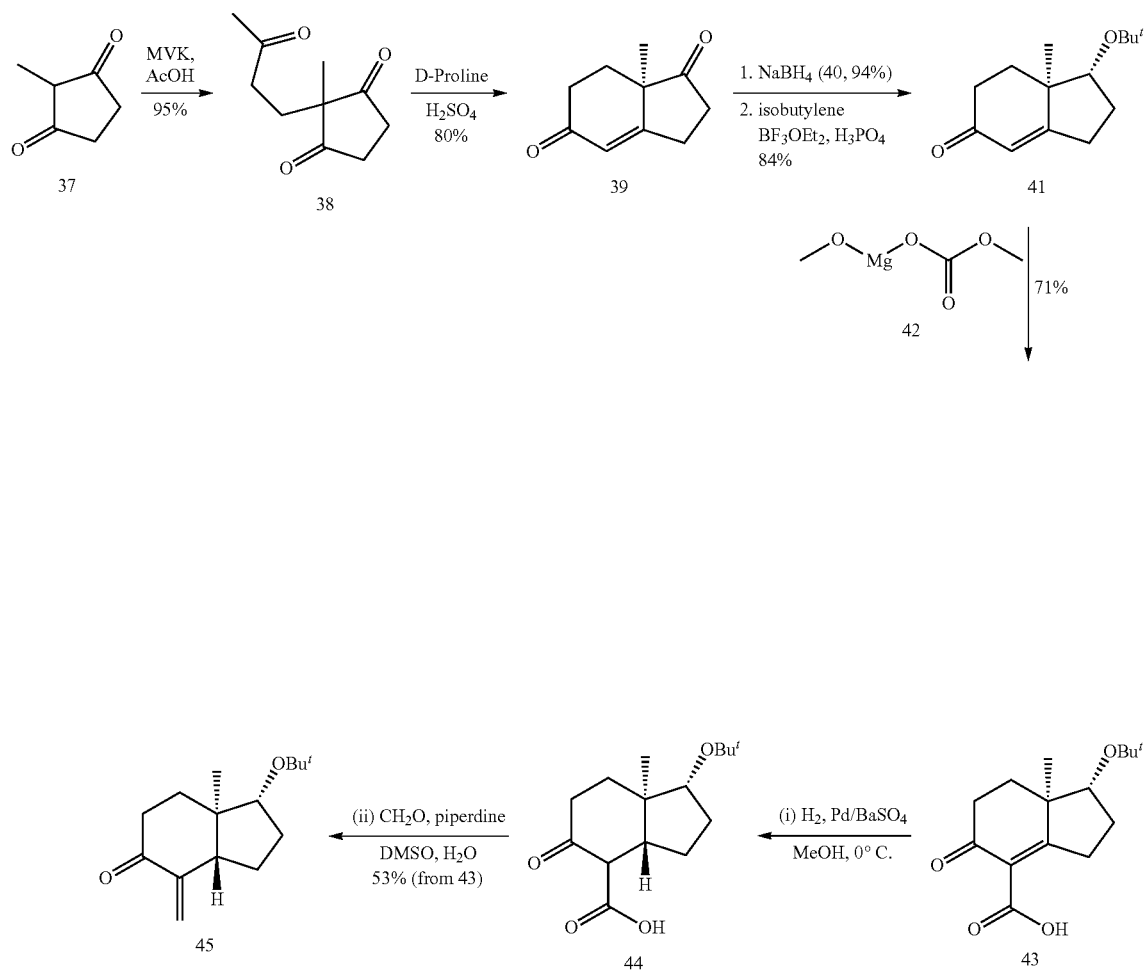

Synthesis of the β-keto ester annulating agent 50 began with ketalization of ethyl-5-oxohexanoate and subsequent reduction of the ester 47 with LiAlH4 to give alcohol 48 (Scheme 10). Swern oxidation of 48 was followed by tin(II) chloride catalyzed coupling with ethyl diazoacetate to give the P-keto ester 50.

Scheme 10

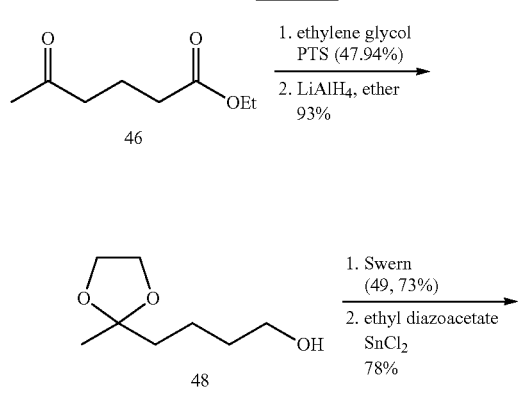

-continued

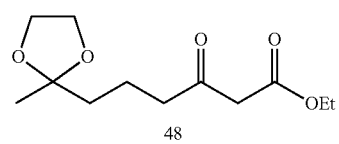

Michael addition of 6-keto ester 50 to enone 45, along with in situ Robinson annulation, saponification, and finally decarboxylation, gave the BCD ring system 51. Reductive alkylation served to introduce what would become the C-19 methyl group of ent-PROG. Reflux of 52 overnight in methanolic HCl gave ent-testosterone (53). Ent-testosterone was then prepared as the C-3 ketal 54 and the C-17 secondary alcohol was oxidized using pyridinium chlorochromate (PCC) to give ketone 55. Treatment of 55 with ethyltriphenylphosphonium bromide under Wittig conditions gave the alkene 56. A final three step sequence involving hydroboration, oxidation, and acid catalyzed removal of the ketal was carried out without intermediate purification steps to give ent-PROG (57) in good yield.

Scheme 11. Completion of ent-PROG (57) synthesis.

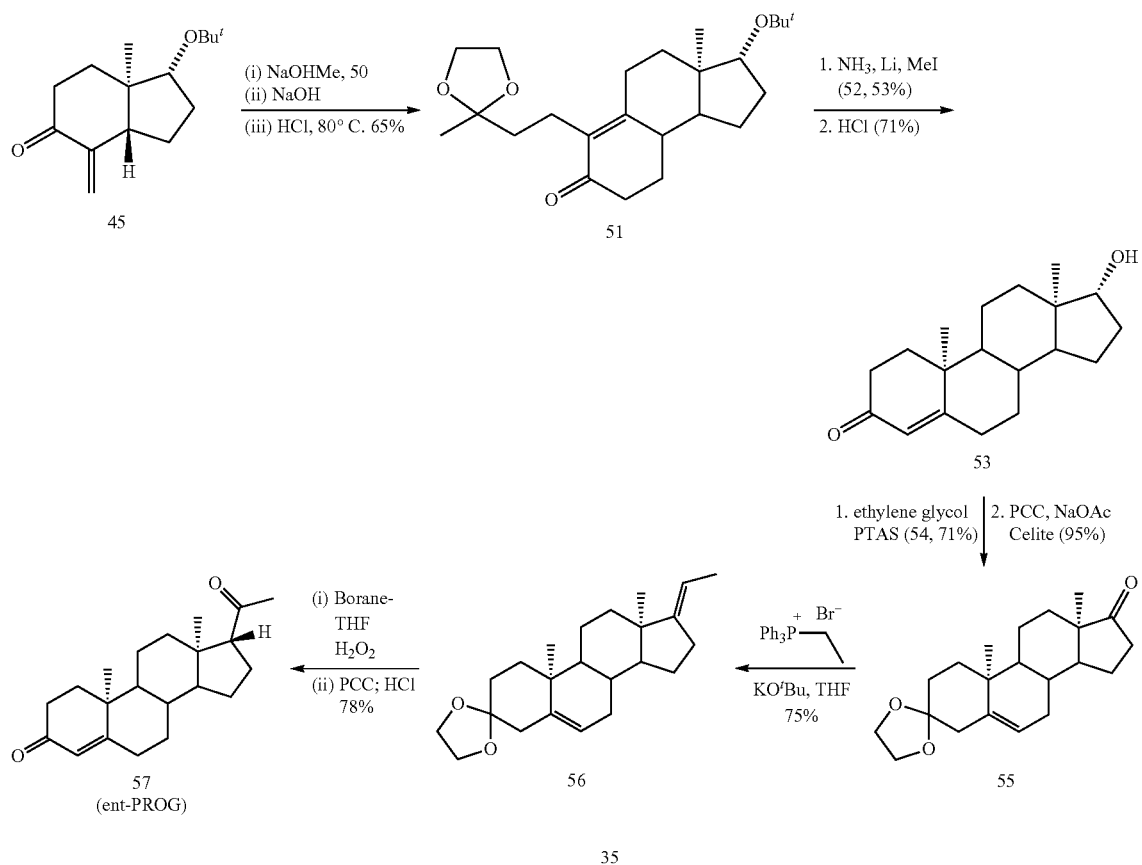

Luche reduction of ent-PROG gave the C-3 a-hydroxy compound 58 (Scheme 12). The same series of reactions involving amino acid coupling, Fmoc cleavage, and HCl salt formation that had been developed for the C-3 nut-PROG series of compounds was applied here to give the ent-PROG derivative P2-13. Additional neuroprotective analogues derived from ent-PROG are prepared according to the description provided above and in the following examples.

Scheme 12. Synthesis of ent-PROG derivative P2-13

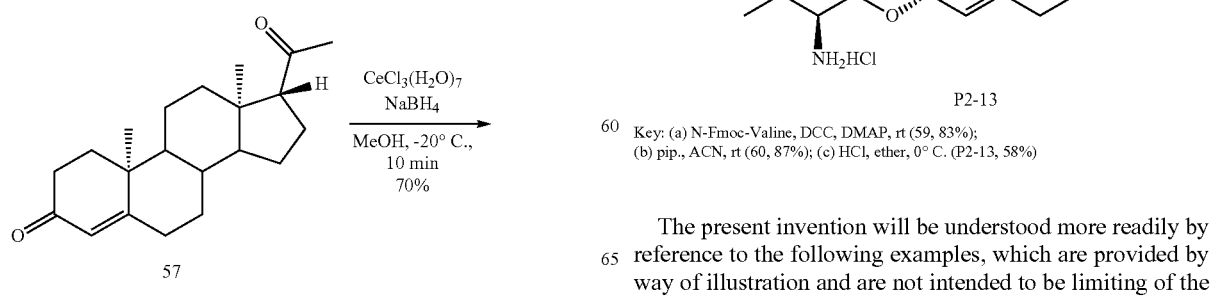

Key: (a) N-Fmoc-Valine, DCC, DMAP, rt (59, 83%); (b) pip., ACN, rt (60, 87%); (c) HCl, ether, 0° C. (P2-13, 58%)

The present invention will be understood more readily by reference to the following examples, which are provided by way of illustration and are not intended to be limiting of the invention.

EXAMPLES

Example 1

Effectiveness of Progesterone Analogues in Reducing Post-Injury Edema

A well established whole animal model of TBI was employed in order to investigate the potential efficacy of the PROG analogue compounds relative to PROG in reducing cerebral edema following injury. Anesthetized male rats were first subjected to cortical contusion and were then given two 8 mg/kg doses of the test compound, the first at 1 h post-surgery and the second at 6 h. The animals were then sacrificed and tissue samples were taken from both injured and non-injured sections of the brain. Wet and dry weights were collected for each sample and cerebral edema (% water content) was determined as the difference in wet and dry weights divided by the wet weight. A "% mean difference" value could then be calculated based on the relative edema difference between injured and non-injured tissue samples for a given animal. The "sham" animals did not receive an injury but served as a control group for possible anesthesia and stress factors. The "vehicle" group were subjected to cortical injury but received only the drug carrier (22.5% 2-hydroxypropyl-β-cyclodextrine in water). All experimental treatments given by injection were made in stock solutions using 2-Hydroxypropyl-b-cyclodextrin (HBC; 45% w/v solution in $H_2O$) as the solvent. These experimental solutions were then diluted 1:1 with sterile water for a final concentration of HBC of 22.5%. Several of the analogues showed equivalent efficacy to progesterone in the cerebral edema assay, including the valine tethered C-3-β-hydroxy PROG derivative P1-31 and the oxime based prodrug compound P1-185. Compound P1-131, the valine coupled derivative of ALLO itself, showed the greatest edema reduction among the ALLO isomer group. Perhaps most notably though was the activity of oxime prodrug P1-186, which showed an average reduction in edema levels almost twice that of PROG.

Results:

FIG. 1 shows the % difference edema results for brain tissue 24 hours post brain injury. The mean % difference calculated for sham, vehicle, progesterone, Compound 31, Compound 57 and Compound 79 subjects were 0.6%, 1.2%, 2.0%, 2.2%, 3.3% and 1.9%, respectively. Samples treated with progesterone, and Compounds 31, 57 and 79 all showed a decrease in edema compared to subjects treated with vehicle.

Example 2

Preparation of Compounds General Experimental

All reagents were obtained from Aldrich. Reactions requiring anhydrous conditions were performed in oven-dried glassware under dry argon. All solvents used were anhydrous or kept dry over activated 4 Å molecular sieves. Convection was achieved by use of a magnetic stirring bar unless otherwise noted. The following abbreviations may be used: dichloromethane (DCM), diethyl ether (ether), water (DI), hexane (hex), ethyl acetate (ea), dimethylformamide (DMF), acetonitrile (ACN), tetrahydrofuran (THF), round bottomed flask (RBF), hours (h), minutes (min), millimole (mmol), equivalents (eq). Reaction progress was monitored via thin-layer chromatography (TLC) on pre-coated glass-backed plates (silica gel 60 Å $F_{254}$, 0.25 mm thickness) purchased from EM Science. Flash chromatography was carried out with silica gel 60 Å (230-400 mesh) from Sorbent Technologies. Automated chromatography was performed on an Isco Combiflash Companion. Unless otherwise stated, organic extracts were dried over commercially available magnesium sulfate and the solvents were removed by rotary evaporation. Brine refers to a saturated sodium chloride solution. $^1H$ and $^{13}C$ NMR spectra were recorded on either a 400 MHz Inova spectrometer or 600 MHz Inova spectrometer in deuterated chloroform ($CDCl_3$) and referenced to the residual solvent peak ($^1H$ δ 7.27 ppm, $^{13}C$ δ 77.23 ppm). Chemical shifts are reported in parts per million (δ), and coupling constants are reported in hertz (Hz). The following abbreviations will be used: singlet (s), doublet (d), triplet (t), quartet (q), multiplet (m). Mass spectra were obtained on either a VG 70-S Nier Johnson or JEOL Mass Spectrometer. Elemental analyses were performed by Atlantic Microlab (Norcross, Ga.).

The abbreviations PROG and ALLO are used for progesterone and allopregnanolone, respectively. Scheme 13 below depicts the synthesis of various C3 amino acid derivatives of the invention, along with representative reaction conditions and reagents.

Scheme 13

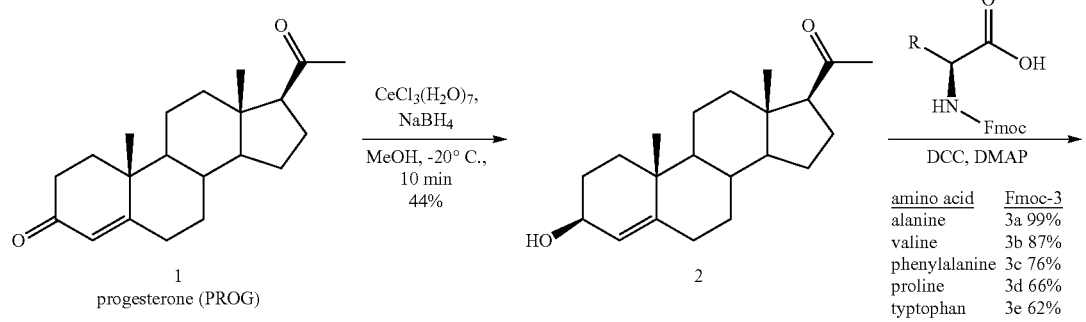

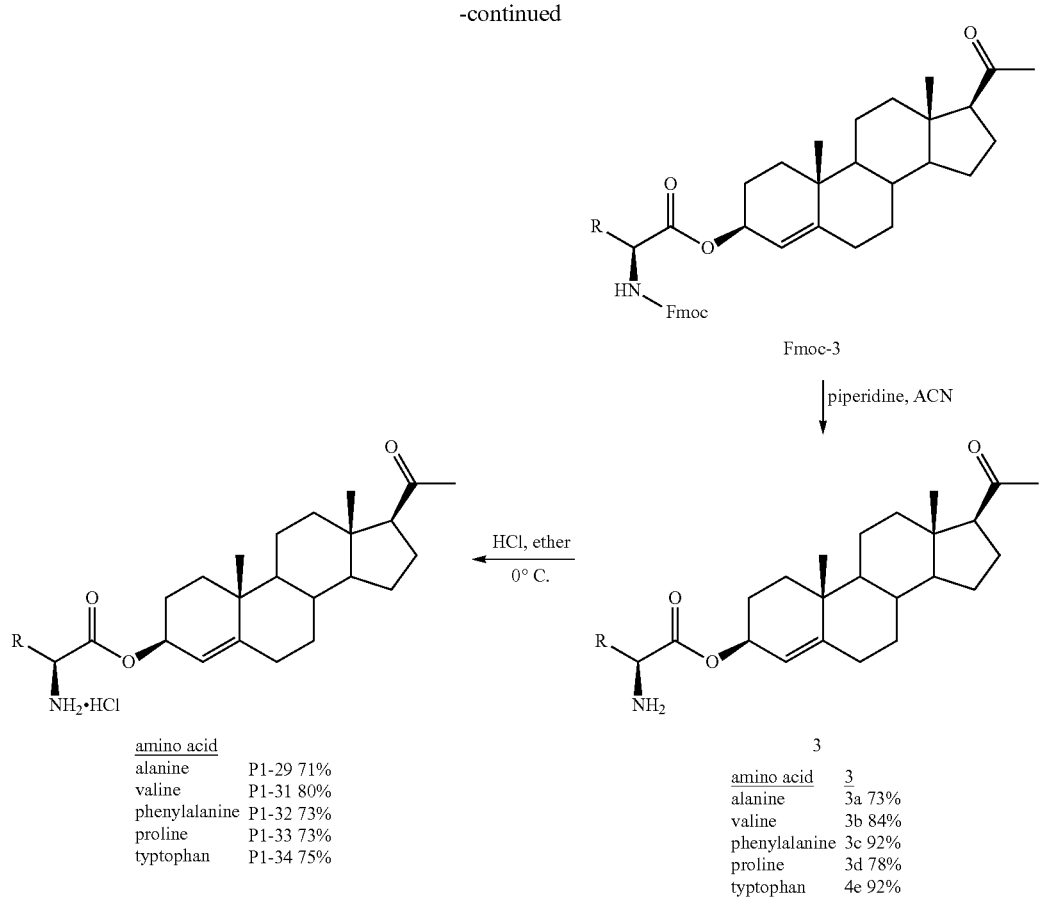

Fmoc-3

↓ piperidine, ACN

| amino acid | P1- | |
|---|---|---|
| alanine | P1-29 | 71% |
| valine | P1-31 | 80% |
| phenylalanine | P1-32 | 73% |
| proline | P1-33 | 73% |
| typtophan | P1-34 | 75% |

| amino acid | 3 | |
|---|---|---|
| alanine | 3a | 73% |
| valine | 3b | 84% |
| phenylalanine | 3c | 92% |
| proline | 3d | 78% |
| typtophan | 4e | 92% |

Example 3

C-3 Progesterone Derivatives

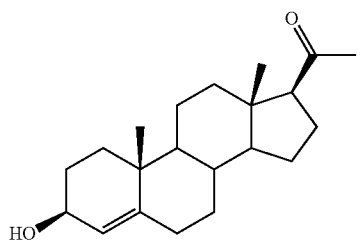 [SMILES: CC(=O)[C@H]1CCC2C3CCC4=C[C@@H](O)CC[C@]4(C)C3CC[C@@]21C]

3-β-Hydroxy-progesterone (2). Progesterone (3.14 g, 10.0 mmol) was added with cerium chloride heptahydrate (3.73 g, 10.0 mmol, 1.00 eq) to an oven dried three necked 250 mL RBF with thermometer. Methanol (100 mL) was added under argon and the solution was chilled to −20° C. Sodium borohydride (0.189 g, 5.00 mmol, 0.500 eq) was then added in bulk. Solution temperature raised briefly up to −16° C. After 15 minutes, 37 mL acetone was added and the solution was warmed to ambient temperature. Water (25 mL) was added and the solvent volume was reduced by approximately 100 mL. Ether was added, along with more water, which caused the solution to become clear and colorless. The aqueous layer was extracted with ether. The organic layers were combined, washed with brine, dried, filtered, and concentrated to give 3.14 g white solid. The solid was prepared as a silica cake, loaded onto a 500 mL silica column, and eluted with 3 L 20% ethyl acetate in hexanes, followed by 2 L 25% ethyl acetate in hexanes. Initially eluting pure fractions were combined and concentrated to give 1.56 g white solid that was 90% pure as determined by proton NMR (other 10% was progesterone). (44%) white solid; $R_f$=0.38 (1:1 EA/hex, PMA stain); $^1$H NMR (400 MHz, CDCl$_3$) δ 5.29 (d, 1H, J=1.6 Hz), 4.18-4.12 (m, 1 H), 2.51 (t, 1 H, J=8.8 Hz), 2.25-0.77 (m, 20 H), 2.11 (s, 3 H), 1.04 (s, 3 H), 0.62 (s, 3 H); $^{13}$C NMR (100 MHz, CDCl$_3$) δ 209.9, 147.4, 123.8, 68.1, 63.9, 56.5, 54.5, 44.3, 39.1, 37.5, 36.1, 35.6, 33.1, 32.3, 31.7, 29.6, 24.6, 22.9, 21.2, 19.1, 13.6.

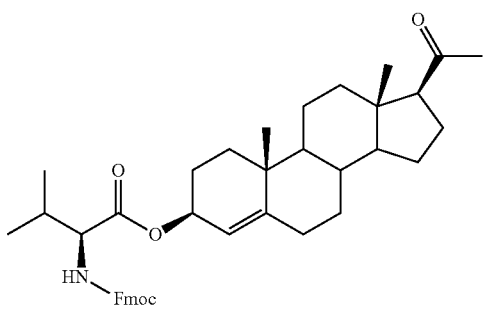

N-Fmoc-L-valine-3-β-progesterone (Fmoc 3a). An oven dried 50 mL RBF was charged with 90% 3-beta-hydroxy-progesterone (0.352 g, 1.00 mmol), N-Fmoc-L-valine (0.339 g, 1.00 mmol, 1.00 eq), and dimethylaminopyridine (DMAP) (0.0244 g, 0.200 mmol, 0.200 eq). The flask was sealed, evacuated, and inert gas flushed and 15 mL anhydrous dichloromethane was added, followed by addition of 1.10 mL (1.10 mmol, 1.10 eq) 1 M dicyclohexylcarbodiimide (DCC) in dichloromethane. The solution was stirred overnight then filtered through Celite. The filtrate was concentrated, prepared as a silica cake and eluted on a 40 g silica column with a 0-25% ethyl acetate in hexanes gradient. The main product was isolated as 0.554 g (87%) clear oil that foamed on drying. $R_f$=0.40 (1:1 EA/hex, PMA stain); $^1$H NMR (600 MHz, CDCl$_3$) δ 7.78 (d, 2H, J=7.2 Hz), 7.63-7.61 (m, 2H), 7.41 (t, 2H, J=7.2 Hz), 7.33 (t, 2H, J=7.2 Hz), 5.35 (d, 1H, J=9.0 Hz), 5.31 (t, 1H, J=7.8 Hz), 5.21 (s, 1H), 4.40 (d, 2H, J=7.2 Hz), 4.31 (dd, 1H, J=9.0, 4.2 Hz), 4.25 (t, 1H, J=7.2 Hz), 2.52 (t, 1H, J=9.0 Hz), 2.23-2.16 (m, 3H), 2.12 (s, 3H), 2.05-1.96 (m, 3H), 1.78-1.55 (m, 6H), 1.50-1.33 (m, 4H), 1.25-1.10 (m, 2H), 1.06 (s, 3H), 1.00 (d, 3H, J=7.2 Hz), 0.93 (d, 3H, J=7.2 Hz), 0.90-0.79 (m, 2H), 0.64 (s, 3H).

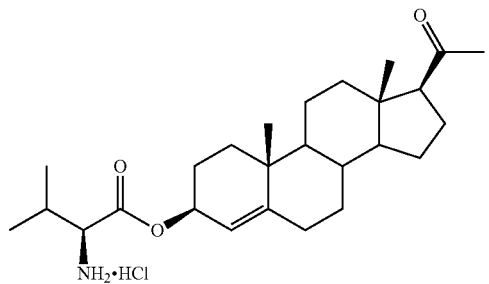

3β-L-Valine-progesterone-HCl (P1-31). A 10 mL RBF with stir bar was charged with 83 mg compound 4 and the flask was evacuated and flushed with argon. Anhydrous ether (2 mL) was added and the solution was chilled in an ice bath. Hydrogen chloride solution (0.10 mL 2.0 M in ether, 0.20 mmol, 1.0 eq) was added dropwise. A white precipitate formed in solution. The precipitate was filtered and washed with chilled ether. The product was recovered as 68 mg (75%) off-white solid.

The following compounds were prepared by the methods as described above:

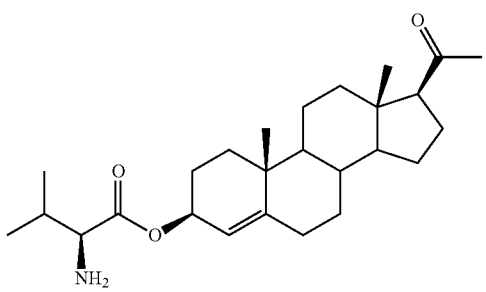 [SMILES: CC(=O)[C@H]1CCC2C3CCC4=C[C@@H](OC(=O)[C@@H](N)C(C)C)CC[C@]4(C)C3CC[C@@]21C]

3-β-L-Valine-progesterone (3a). A 25 mL RBF was charged with 0.340 g (0.533 mmol) compound 3a. The flask was evacuated and inert gas flushed and 5 mL each of acetonitrile and dimethylformamide were added. A 0.527 mL (5.33 mmol, 10.0 eq) volume of piperidine was added and the clear colorless solution was stirred at room temperature for 30 min. The solvent was removed with addition of toluene for complete removal of DMF. A white solid formed that was redissolved in a minimum amount of toluene and loaded neat onto a 12 g silica column and eluted with 0-75% ea in hexanes. Main product containing fractions were combined and dried to give 0.196 g (89%) white foam. $^1$H NMR (400 MHz, CDCl$_3$) δ 5.29-5.23 (m, 1H), 5.20 (d, 1H, J=1.6 Hz), 3.27 (d, 1H, J=4.8 Hz), 2.52 (t, 1H, J=9.2 Hz), 2.36-1.93 (m, 6H), 2.11 (s, 3H), 1.79-1.08 (m, 14H), 1.06 (s, 3H), 0.98 (d, 3H, J=6.8 Hz), 0.95-0.77 (m, 3H), 0.90 (d, 3H, J=6.8 Hz), 0.62 (s, 2H); $^{13}$C NMR (100 MHz, CDCl$_3$) δ 209.8, 175.6, 149.3, 119.3, 71.3, 63.8, 60.2, 56.4, 54.2, 44.3, 39.0, 37.5, 36.0, 35.2, 33.0, 32.3 (2 C), 31.7, 25.3, 24.6, 22.9, 21.1, 19.6, 19.0, 17.3, 13.6; IR (solid): 2934, 2843, 1724, 1705, 1384, 1354, 1166, 1146, 978, 873, 852 cm$^{-1}$; HRMS-ESI m/z 416.3156 ([M+H]$^+$, C$_{26}$H$_{42}$NO$_3$ requires 416.3159).

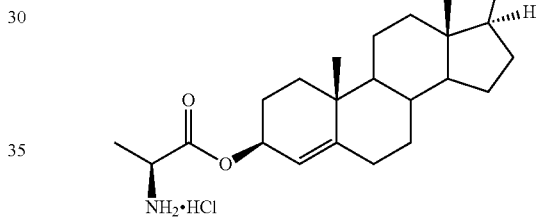

3β-L-Alanine-progesterone-HCl (P1-29). (52% from P1-30) white solid. $^1$H NMR (400 MHz, CDCl$_3$) δ 8.63 (bs, 2H), 5.25 (t, 1H, J=7.6 Hz), 5.14 (s, 1H), 4.12 (d, 1H, J=7.6 Hz), 2.64 (bs, 1H), 2.43 (t, 1H, J=8.8 Hz), 2.20-0.68 (m, 21H), 2.04 (s, 3H), 1.65 (d, 3H, J=7.2 Hz), 0.99 (s, 3H), 0.57 (s, 3H); $^{13}$C NMR (100 MHz, CDCl$_3$) δ 209.7, 170.1, 150.1, 118.4, 73.4, 63.8, 56.4, 54.1, 49.5, 44.2, 39.0, 37.5, 36.0, 35.0, 33.0, 32.3, 31.7, 25.0, 24.6, 23.0, 21.2, 19.0, 16.4, 13.5; hR (film): 2934, 2849, 1741, 1703, 1237, 1207, 1113, 916, 731 cm'; HRMS-ESI m/z 388.2847 ([M-Cl]$^+$, C$_{24}$H$_{38}$NO$_3$ requires 388.2846); Anal. Calcd for C$_{24}$H$_{38}$ClNO$_3$+%2H$_2$O: C, 66.57; H, 9.08; N, 3.23. Found C, 66.42; H, 9.01; N, 3.19.

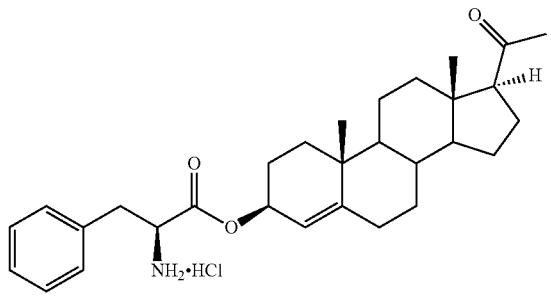

3β-L-Phenylalanine-progesterone-HCl (P1-32). (51% from P1-30) white solid. ¹H NMR (400 MHz, CDCl₃) δ 8.71 (bs, 2H), 7.30-7.21 (m, 5H), 5.17 (bs, 1H), 4.97 (s, 1H), 4.32 (bs, 1H), 3.47-3.29 (m, 2H), 2.48 (t, 1H, J=8.6 Hz), 2.20-0.68 (m, 20H), 2.10 (s, 3H), 0.97 (s, 3H), 0.60 (s, 3H); ¹³C NMR (100 MHz, CDCl₃) δ 209.7, 168.8, 149.9, 134.2, 130.1, 129.0, 127.8, 118.2, 73.6, 63.8, 56.4, 54.5, 54.1, 44.2, 39.0, 37.4, 36.6, 36.0, 34.8, 33.0, 32.2, 31.7, 24.9, 24.6, 23.0, 21.2, 18.9, 13.6; IR (film): 2929, 2848, 1732, 1701, 1233, 1202, 1109, 912, 729, 700 cm⁻¹; HRMS-ESI m/z 464.3160 ([M-Cl]+, $C_{30}H_{42}NO_3$ requires 464.3159); Anal. Calcd for $C_{30}H_{42}ClNO_3 + \frac{1}{2}H_2O$: C, 70.77; H, 8.51; N, 2.75. Found C, 70.74; H, 8.31; N, 2.78.

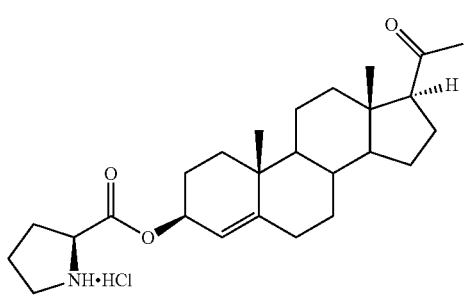

3β-L-Proline-progesterone-HCl (P1-33). (38% from P1-30) white solid. ¹H NMR (400 MHz, DMSO) δ 10.32 (bs, 1H), 9.02 (bs, 1H), 5.26 (s, 1H), 5.22 (s, 1H), 4.33 (s, 1H), 3.40 (s, 1H), 3.20 (d, 2H, J=7.2 Hz), 2.56 (t, 1H, J=8.6 Hz), 2.30-0.73 (m, 23H), 2.05 (s, 3H), 1.02 (s, 3H), 0.54 (s, 3H); ¹³C NMR (100 MHz, CDCl₃) δ 209.6, 168.9, 150.6, 118.0, 74.1, 63.8, 59.5, 56.4, 54.0, 46.6, 44.2, 38.9, 37.5, 35.9, 34.8, 33.0, 32.6, 31.7, 29.4, 25.1, 24.5, 24.0, 22.9, 21.1, 19.0, 13.5; IR (film): cm⁻¹; HRMS-ESI m/z 414.3005 ([M-Cl]⁺, $C_{26}H_{40}NO_3$ requires 414.3003); Anal. Calcd. for $C_{26}H_{40}ClNO_3 + \frac{1}{2}H_2O$: C, 68.03; H, 9.00; N, 3.05. Found C, 68.21; H, 8.89; N, 3.02.

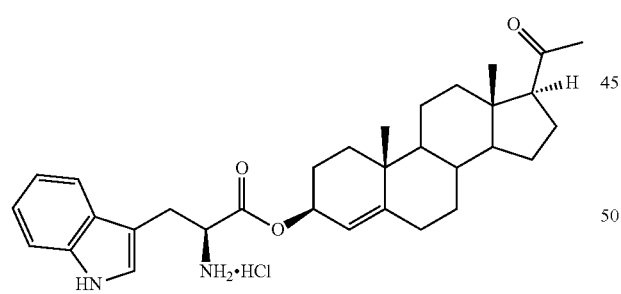

3β-L-Tryptophan-progesterone-HCl (P1-34). (43% from P1-30) white solid. ¹H NMR (400 MHz, DMSO) δ 11.1 (bs, 1H), 8.62 (bs, 2H), 7.53 (d, 1H, J=7.6 Hz), 7.36 (d, 1H, J=7.6 Hz), 7.24 (s, 1H), 7.08 (t, 1H, J=7.4 Hz), 6.99 (t, 1H, J=7.4 Hz), 5.07 (bs, 1H), 4.73 (s, 1H), 4.14 (bs, 1H), 3.46-3.20 (m, 2H), 2.54 (t, 1H, J=8.8 Hz), 2.20-0.67 (m, 20H), 2.05 (s, 3H), 0.95 (s, 3H), 0.53 (s, 3H); ¹³C NMR (100 MHz, CDCl₃) δ 209.7, 169.3, 150.3, 136.4, 126.9, 126.6, 122.0, 119.3, 118.5, 118.1, 112.1, 105.9, 74.1, 63.8, 56.4, 54.0, 53.6, 44.2, 39.0, 37.5, 35.9, 34.7, 33.0, 32.3, 31.7, 26.1, 25.0, 24.6, 23.0, 21.1, 19.0, 13.6; IR (film): 2929, 2849, 1.732, 1701, 1456, 1435, 1354, 1218, 1108, 730 cm⁻¹; HRMS-ESI m/z 503.3271 ([M-Cl]⁺, $C_{32}H_{43}N_2O_3$ requires 503.3268); Anal.

Calcd for $C_{32}H_{43}ClN_2O_3 + \frac{3}{4}H_2O$: C, 69.54; H, 8.12; N, 5.07. Found C, 69.57; H, 8.06; N, 5.04.

Scheme 14 below depicts the synthesis of C3 valine derivative, where the C3 hydroxy group is in the β configuration. Similar conditions may be used for the synthesis of other amino acid derivatives.

Scheme 14

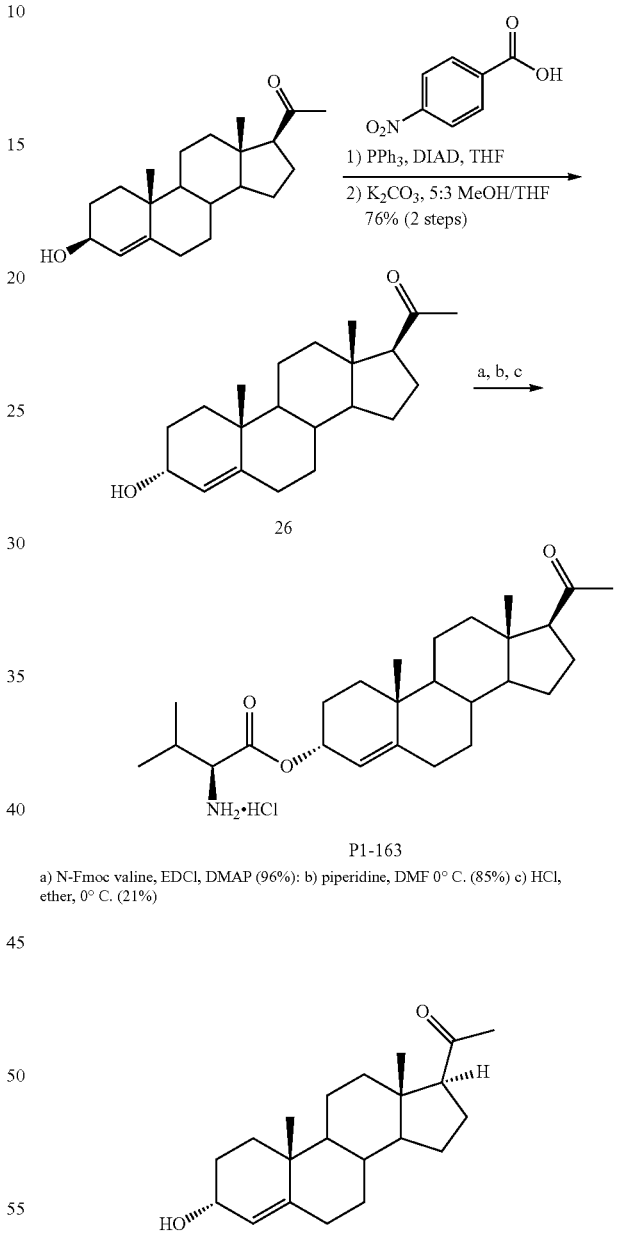

a) N-Fmoc valine, EDCl, DMAP (96%): b) piperidine, DMF 0° C. (85%) c) HCl, ether, 0° C. (21%)

3α-Hydroxy-progesterone (26). Ester formation: Compound 12 (0.560 g, 1.59 mmol), triphenylphosphine (0.877 g, 3.34 mmol, 2.10 eq), and p-nitrophenylbenzoic acid (0.559 g, 3.34 mmol, 2.10 eq) were added to a 100 mL oven dried flask that was evacuated and inert gas flushed. A 20 mL volume of anhydrous THF was added. The solution was cooled to 0° C. and diisopropylazodicarbonate (0.693 mL in 10 mL THF solution, 3.34 mmol, 2.10 eq) was added dropwise over 1 h. The solution was stirred at 0° C. for an additional 1 h. The reaction was diluted with 50 mL ether and washed with saturated sodium bicarbonate solution (3×25 mL). The aqueous layers were combined and extracted with ether. The organic layers were combined, dried, filtered, and concentrated to give a pale orange oil. The oil was loaded onto a 40 g silica column in a minimum amount of DCM and eluted with 0-25% ea in hex over 35 min. Main peak fractions were combined and concentrated to give a clear oil that crystallized on standing. Crude wet mass was 0.820 g. Saponification: The esterification product (0.613 g, 1.32 mmol) was dissolved in 12 mL 5:3 MeOH/THF in a 25 mL RBF and potassium carbonate (0.364 g, 2.63 mmol, 2.00 eq), dissolved in 2 mL DI, was added. A white precipitate formed in solution that gradually dissolved over the course of 1 h. The solvents were removed and the aqueous layer was extracted with ether. The organic layers were combined, washed with brine, dried, filtered, and concentrated. The resulting white solid was re-dissolved in a minimum amount of DCM and eluted on a 40 g silica column with 0-35% ea in hexanes gradient over 40 min. The desired major product was isolated as 0.380 g (91%) white solid. $R_f$=0.31 (1:1 EA/hex, PMA stain); $^1$H NMR (400 MHz, CDCl$_3$) δ 5.47 (dd, 1 H, J=4.8, 1.6 Hz), 4.10-4.06 (m, 1H), 2.53 (t, 1H, J=9.2 Hz), 2.27-0.82 (m, 20H), 2.12 (s, 3H), 0.99 (s, 3H), 0.64 (s, 3H); $^{13}$C NMR. (100 MHz, CDCl$_3$) δ 209.8, 150.1, 121.1, 64.4, 63.9, 56.5, 54.1, 44.4, 39.2, 37.7, 36.0, 32.9, 32.5, 31.9, 31.7, 28.0, 24.6, 23.0, 21.7, 18.3, 13.6; TR (solid): 3485, 3414, 2929, 2842, 1694, 1356, 1.015 cmi$^{-1}$ HRMS-ESI m/z 299.2366 ([M+H—H$_2$O]$^+$, C$_{21}$H$_{31}$O requires 299.2369).

N-Fmoc-L-valine-3a-progesterone (Fmoc P1-163). Compound 14 (0.100 g, 0.314 mmol), N-Fmoc-valine (0.213 g, 0.628 mmol, 2.00 eq), N-(3-dimethylaminopropyl)-N'-ethylcarbodiimide hydrochloride (EDCI) (0.120 g, 0.628 mmol, 2.00 eq), and DMAP (4 mg, 0.10 eq) were added to an oven dried 25 mL RBF. The flask was evacuated and inert gas flushed and 6 mL anhydrous DCM was added. The reaction was stirred at room temperature for 36 h. The solution was quenched and washed with saturated ammonium chloride solution (2×20 mL). The aqueous layers were combined and extracted with DCM. The organic layers were combined, washed with brine, dried, filtered, and concentrated. The clear oil was loaded in a minimum amount of DCM. onto a 12 g silica column and eluted with a 0-15% ea in hex gradient over 45 minutes. The desired product was obtained as 0.193 g (96%) white foam. $R_f$=0.63 (1:1 EA/hex); $^1$H NVIR (400 MHz, CDCl$_3$) δ 7.77 (d, 211, J=7.6 Hz), 7.63 (d, 2H, J=7.2 Hz), 7.41 (t, 2H, J=7.2 Hz), 7.33 (dt, 2H, J=7.2, 0.8 Hz), 5.44 (d, 1H, J=4.4 Hz), 5.36 (d, 1H, J=8.8 Hz), 5.19 (d, 1H, J=2.4 Hz), 4.48-4.44 (m, 1H), 4.35-4.23 (m, 3H), 2.43 (t, 1H, J=8.8 Hz), 2.28-0.79 (m, 20H), 2.09 (s, 3H), 1.00 (d, 3H, J=6.8 Hz), 0.99 (s, 3H), 0.94 (d, 3H, J=7.2 Hz), 0.62 (s, 3H); $^{13}$C NMR (100 MHz, CDCl$_3$) δ 209.8, 172.0, 156.5, 152.9, 144.2, 143.9, 141.5, 127.9, 127.3, 125.5, 125.4, 120.2, 116.5, 69.0, 67.2, 63.8, 59.2, 56.2, 53.9, 47.5, 44.2, 38.9, 37.6, 35.8, 32.5, 31.7, 31.6, 25.1, 24.5, 22.9, 21.6, 19.3, 1.8.1, 17.6, 13.5; IR (solid): 3335, 2935, 1700, 1449, 1237, 1195, 759, 740 cm$^{-1}$

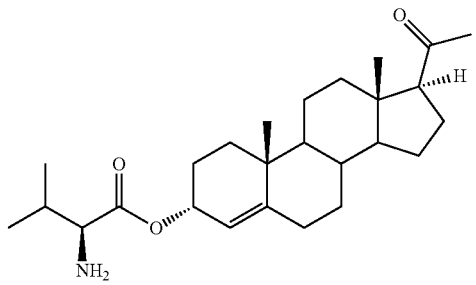

3α-L-Valine-progesterone (PI163 free base). Prepared according to the method described for compound 5b. (85%) clear oil; $^1$H NMR (600 MHz, CDCl$_3$) δ 5.44 (d, 1H, 1$^-$4.8 Hz), 5.17 (s, 1H), 3.28 (d, 111, J=4.8 Hz), 2.53 (t, 1H, J=9.0 Hz), 2.27-0.86 (m, 2211), 2.12 (s, 3H), 1.01 (s, 3H), 1.00 (d, 3H, J=6.6 Hz), 0.91 (d, 3H, J=7.2 Hz), 0.65 (s, 3H); $^{13}$C NMR (150 MHz, CDCl$_3$) δ 209.8, 175.5, 152.5, 117.1, 68.1, 63.9, 60.1, 56.4, 54.0, 44.3, 39.1, 37.6, 35.9, 32.6, 32.5 (2C), 32.4, 31.7, 25.2, 24.6, 23.0, 21.6, 19.6, 18.2, 17.3, 13.6; IR (solid): 2933, 2872, 1722, 1704, 1383, 1358, 1237, 1178, 976 cm$^{-1}$; H12MS-ESI m/z 416.3155 ([.M+H]$^+$, C$_{26}$H$_{42}$NO$_3$ requires 416.3159).

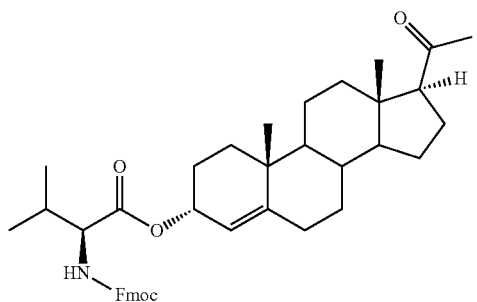

3α-L-Valine-progesterone-HCl (P1-163). Prepared according to the method described for compound P1-31. (21%) white powdery solid; $^1$H NMR (400 MHz, CDCl$_3$) 5.45 (d, 1H, J=4.4 Hz), 5.25 (s, 1H), 3.82 (d, 1H, J=3.2 Hz), 2.53 (t, 1TI, J=9.2 Hz), 2.48-2.37 (m, 1H), 2.29-0.79 (m, 22H), 2.12 (s, 3H), 1.15 (d, 3H, J=6.8 Hz), 1.11. (d, 3H, J=6.8 Hz), 1.00 (s, 3H), 0.64 (s, 3H); $^{13}$C NMR. (100 MHz, CDCl$_3$) δ 209.8, 169.7, 153.3, 116.3, 70.0, 63.9, 59.0, 56.3, 53.9, 44.3, 39.0, 37.6, 35.9, 32.5, 32.4 (2C), 31.7, 30.6, 25.0, 24.6, 23.0, 21.6, 18.7, 18.2 (2C), 13.6; IR (film): 2935, 2876, 2620, 1734, 1703, 1383, 1357, 1228, 731 cm$^{-1}$; Anal. Calcd for C$_{26}$H$_{42}$ClNO$_3$+½H$_2$O: C, 67.73; H, 9.40; N, 3.04. Found C, 67.00; H, 9.53; N, 3.04.

Example 4

C-20 Progesterone Derivatives

Scheme 15 describes the synthesis of C20 valine derivative P1-57 with representative reagents and conditions. This procedure may be used to prepare C20 derivatives of other amino acid using the same or alternate reagents.

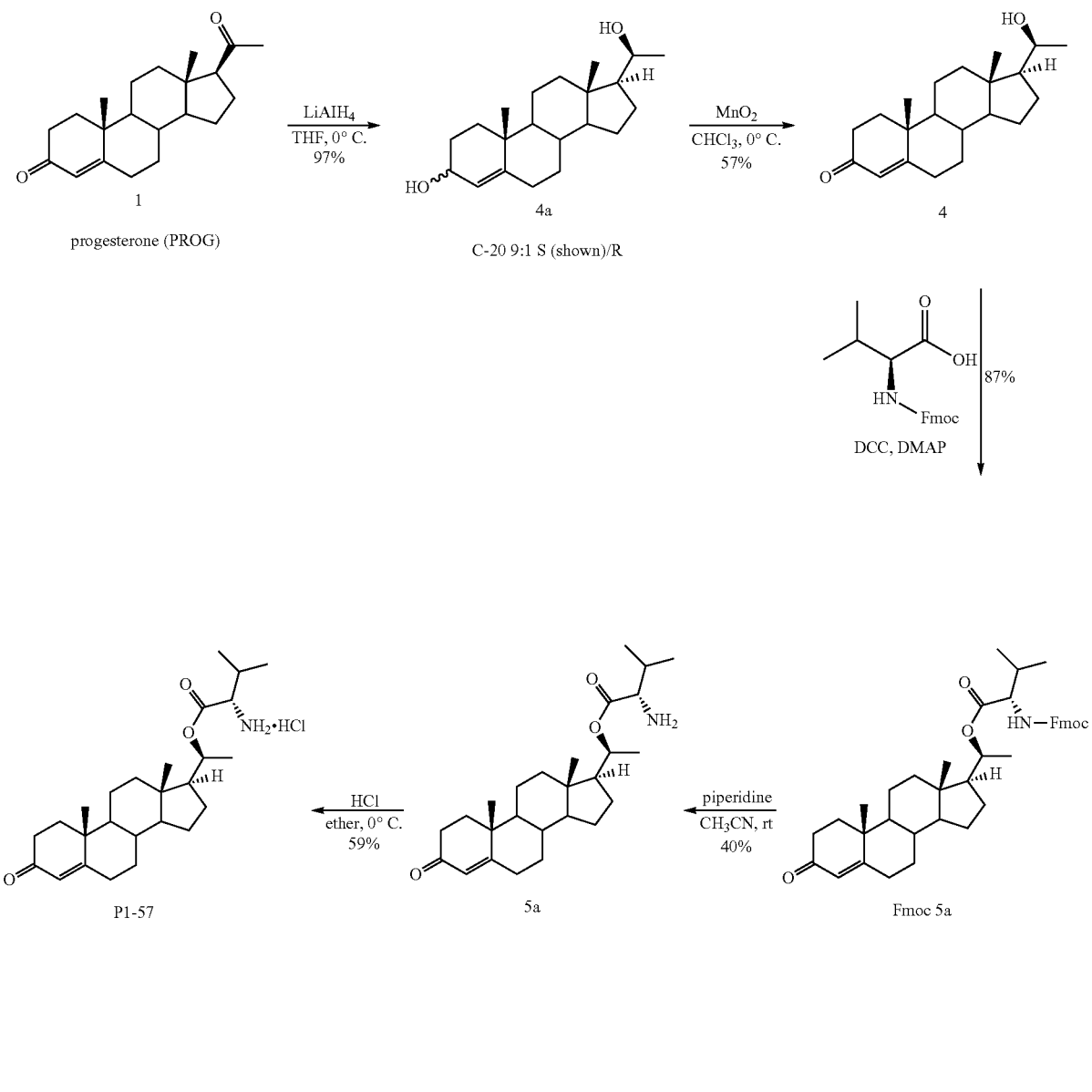

Scheme 15

3,20-Hydroxy-progesterone (4a). An oven dried RBF was charged with 25 mL anhydrous THF and chilled in an ice bath. A 4.50 mL volume (9.00 mmol, 2.25 eq) of 2.0 M lithium aluminum hydride in THF was added. A separate ~10 mL solution of progesterone (1.26 g, 4.00 mmol) in anhydrous THF was prepared in a dry flask. The solution was transferred to the reaction flask dropwise over 30 minutes. The mixture was heated under reflux for 1 h, cooled to room temperature, and quenched by the addition of ethyl acetate, followed by aqueous sodium sulfate. Solid sodium sulfate was added to remove excess water. The remaining salts were filtered and washed with THF. The organic filtrates were combined and concentrated to give 1.24 g (97%, recovered with 8% progesterone) white crystalline solid.

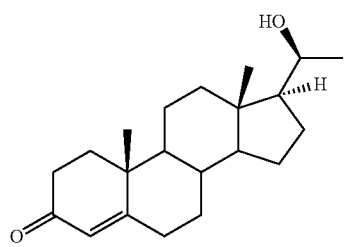 [SMILES: C[C@H](O)[C@H]1CCC2C3CCC4=CC(=O)CC[C@]4(C)C3CC[C@@]21C]

20-S-Hydroxy-progesterone (4). A 100 mL RBF was charged with 1.00 g crude compound 5 and 5.00 g manganese dioxide (activated by heating in oven for 2 days then cooled in a dessicator) and the reactants were suspended in 30 mL chloroform. The mixture was stirred at room temperature overnight. The mixture was then filtered through a pad of Celite and rinsed with chloroform. The clear, colorless filtrate was evaporated to dryness to give an off-white solid. The solid was recrystallized from ethyl acetate/hexane to give 0.565 g (57%) white solid.

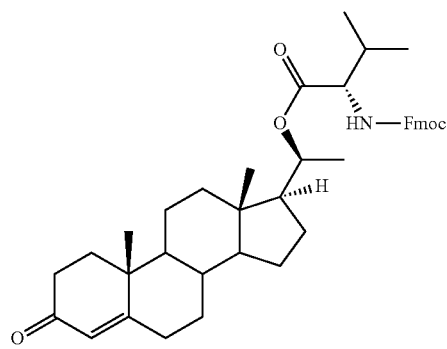

20-S—N-Fmoc-L-valine-progesterone (Fmoc 5a). An oven dried 50 mL RBF was charged with compound 4 (0.250 g, 0.790 mmol), N-Fmoc-L-valine (0.271 g, 0.798 mmol, 1.01 eq), and DMAP (0.010 g, 0.079 mmol, 0.100 eq). The flask was sealed, evacuated, and inert gas flushed and 10 mL anhydrous dichloromethane was added, followed by addition of 0.869 mL (0.434 mmol, 1.10 eq) 1 M DCC in dichloromethane. The solution was stirred overnight and then filtered through Celite and washed with dichloromethane. The crude product was loaded as a silica cake on a 40 g silica column and eluted with a 0-25% ethyl acetate in hexanes gradient over 45 min. Main product containing fractions were combined and dried under vacuum to give 0.436 g (87%) white foam.

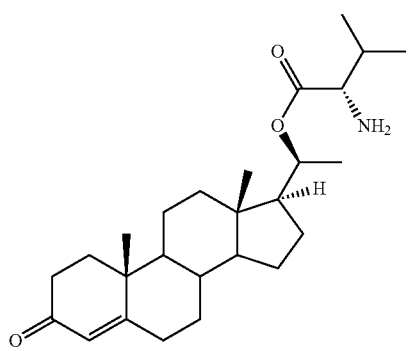 [SMILES: CC(C)[C@H](N)C(=O)O[C@@H](C)[C@H]1CCC2C3CCC4=CC(=O)CC[C@]4(C)C3CC[C@@]21C]

20-S-L-Valine-progesterone (5b). Compound 5a (0.374 g, 0.586 mmol) was dissolved in 6 mL anhydrous acetonitrile in a 25 mL RBF under argon. Piperidine (0.646 mL, 6.54 mmol, 10.0 eq) was added quickly dropwise at room temperature. A white clumping precipitate was observed in solution after 20 minutes. The precipitate was filtered and rinsed with acetonitrile. The filtrate was concentrated and the resulting white solid was redissolved in dichloromethane and concentrated in the presence of 1 g silica. The silica cake was eluted with 0-75% ethyl acetate in hexanes over 45 minutes on a 12 g silica column. Main product containing fractions were combined and concentrated to give a white solid. The solid was recrystallized from hexanes/ethyl acetate to give 0.097 g (40%) white powdery solid. $R_f$=0.06 (1:1 EA/hex); [1] H NMR (400 MHz, CDCl$_3$) δ 5.72 (s, 1 H), 4.93-4.86 (m, 1 H), 3.23 (d, 1 H, J=4.4 Hz), 2.46-2.23 (m, 5 H), 2.10-0.80 (m, 18H), 1.17 (s, 3H), 1.16 (d, 3H, J=6.4 Hz), 0.98 (d, 3 H, J=7.2 Hz), 0.88 (d, 3 H, J=6.8 Hz), 0.68 (s, 3 H); $^{13}$C NMR (100 MHz, CDCl$_3$) δ 199.8, 175.1, 171.5, 124.0, 73.4, 59.9, 55.4, 55.1, 54.0, 42.5, 39.2, 38.8, 35.9, 35.6, 34.2, 33.0, 32.2 (2 C), 25.6, 24.4, 21.1, 20.0, 19.5, 17.6, 17.1, 12.7; IR (film): 2933, 1721, 1672, 1381, 1187, 1071, 864 cm$^{-1}$; HRMS-ESI m/z 416.3156 ([M+H]$^+$, C$_{26}$H$_{42}$NO$_3$ requires 416.3159).

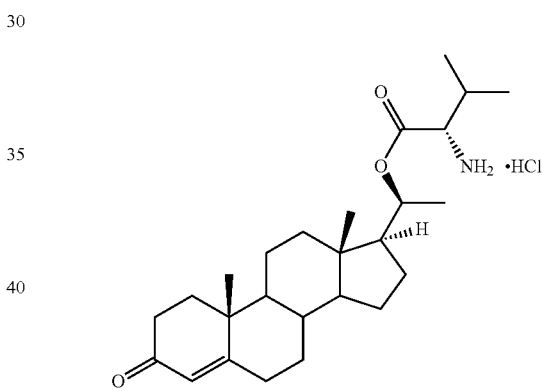

20-S-L-Valine-progesterone HCl salt (P1-57). Compound 8 (62 mg, 0.150 mmol) was dissolved in 1.5 mL anhydrous ether in a 5 mL RBF under argon and the solution was chilled in an ice bath. A 0.158 mL volume (0.158 mmol, 1.05 eq) of 1.00 M hydrochloric acid in diethyl ether was added. A precipitate formed in solution. The precipitate was filtered and washed with chilled ether to give 40 mg (59%) off-white solid.

Example 5

Progesterone Prodrug Compounds

Scheme 15 depicts the synthesis of P1-79, a C20 tryptophan oxime derivative. Similar reagents and conditions may be used to prepare C20 oxime derivatives.

Scheme 15
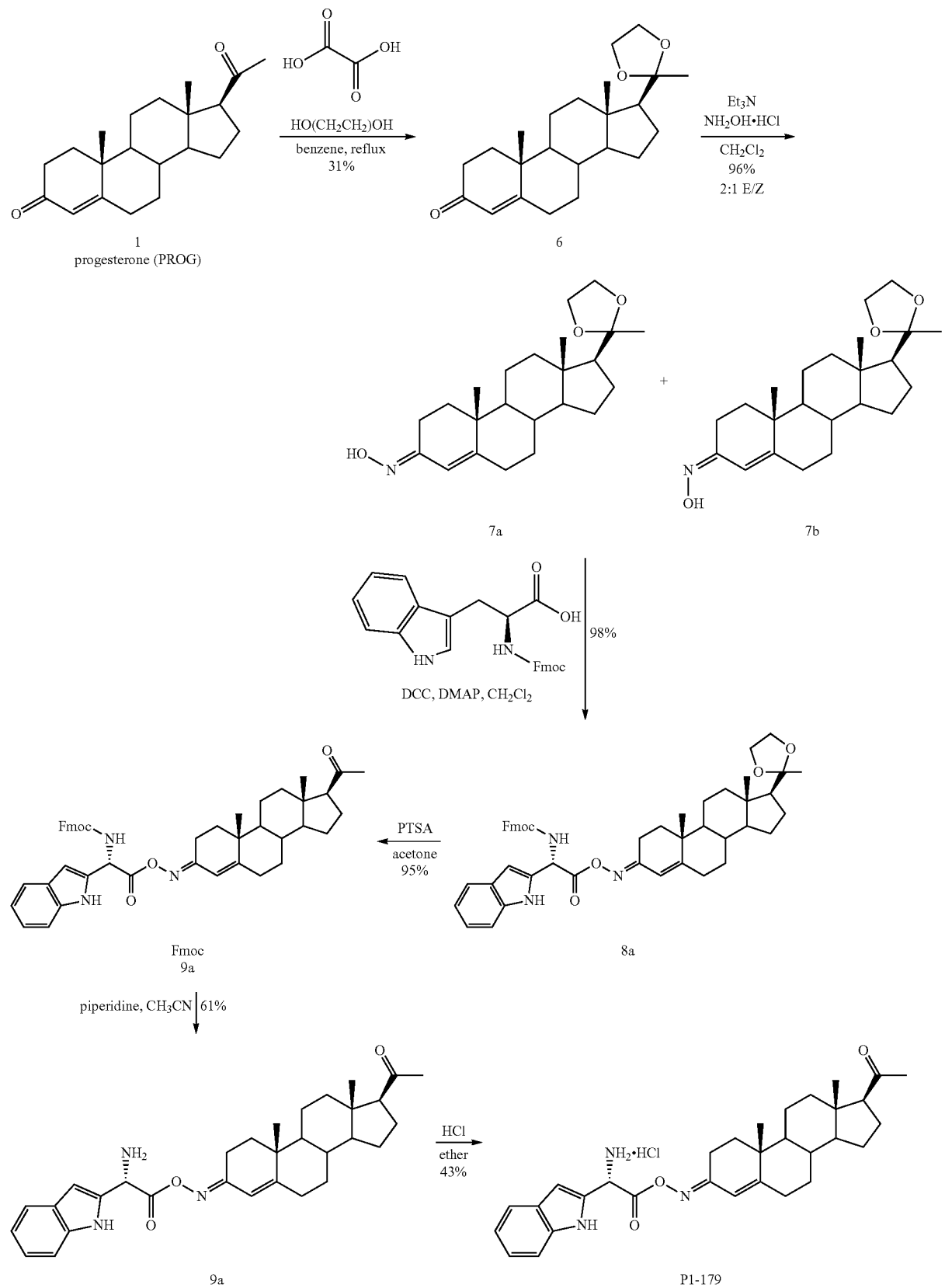

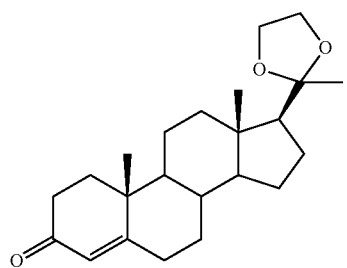 [SMILES: CC1([C@H]2CCC3C4CCC5=CC(=O)CC[C@]5(C)C4CC[C@@]32C)OCCO1]

20-Ketal-progesterone (6). Progesterone (25.0 g, 79.5 mmol), oxalic acid (7.16 g, 79.5 mmol, 1.00 eq) and 350 mL benzene were added to a 1 L RBF with stir bar, followed by 75.4 mL (1.35 mol, 17.0 eq) ethylene glycol. The flask was fitted with a condenser topped Dean Stark apparatus and refluxed for 48 h. The solution was cooled and quenched with saturated sodium bicarbonate solution. The aqueous phase was extracted with benzene. The organic layers were combined and washed with DI. The organic layer was treated with magnesium sulfate to the point of free flowing solid and stirred at room temperature overnight. The solution was filtered and concentrated to give a sticky white solid. The solid was recrystallized from petroleum ether/acetone to give 9.30 g (31% at 94% purity) white solid.

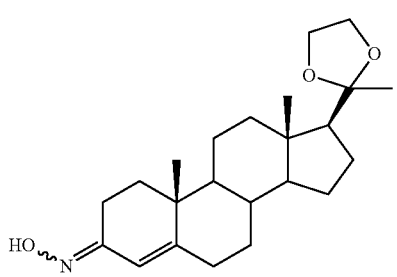 [SMILES: CC1([C@H]2CCC3C4CCC5=CC(=NO)CC[C@]5(C)C4CC[C@@]32C)OCCO1]

3-Hydroxy-oxime-20-ketal-progesterone (7a/7b). Hydroxylamine HCl (2.78 g, 40.0 mmol, 4.00 eq) was added to a 100 mL oven dried RBF with 15 mL anhydrous dichloromethane. Triethylamine (6.97 mL, 50.0 mmol, 5.00 eq) was added and the mixture was stirred for 45 minutes. Compound 6 was dissolved in 20 mL anhydrous DCM and added quickly dropwise to the reaction mixture. The reaction was stirred for 24 h at room temp. The solution was quenched with the addition of DI. The organic layer was washed with water. The aqueous washes were combined and extracted with dichloromethane. The organic layers were combined, dried, filtered, and concentrated with 10 g silica. The silica cake was eluted with a 0-25% ea in hex gradient over 60 minutes on a 120 g silica column. Main product were recovered as 2.23 g (60%) E oxime and 1.33 g (36%) Z oxime, both as white solids.

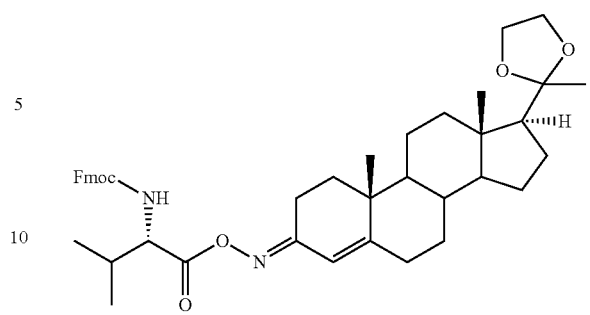

N-Fmoc-valine-3-E-oxime-20-ketal-progesterone (29). Prepared according to the method described for compound 4b. (99%) clear oil that foamed on drying; $R_f$=0.54 (1:1 EA/hex); $^1$H NIIVIR (600 MHz, CDCl$_3$) δ 7.77 (d, 2H, J=7.8 Hz), 7.61 (dd, 2H, J=7.2, 3.0 Hz), 7.42-7.39 (m, 2H), 7.32 (t, 211, J=7.6 Hz), 5.98 (s, 1H), 5.46 (d, 1H, J=9.6 Hz), 4.44-4.40 (m, 3H), 4.24 (t, 1H, J=7.2 Hz), 4.02-3.86 (m, 4H), 3.01 (d, 1H, J=16.8), 2.37-0.81 (m, 20H), 1.30 (s, 3H), 1.08 (s, 3H), 1.02 (d, 3H, J=7.2 Hz), 0.99 (d, 3H, J=7.2 Hz), 0.80 (s, 3H); $^{13}$C NMR (150 MHz, CDCl$_3$) δ 170.1, 164.2, 162.4, 156.4, 144.1, 143.9, 127.9, 127.3, 125.3, 120.2, 115.9, 112.0, 67.3, 65.4, 63.4, 58.4, 58.3, 56.0, 53.7, 47.3, 42.0, 39.5, 38.3, 35.3, 34.4, 33.1, 32.1, 31.9, 24.7, 23.9, 23.1, 21.2, 21.0, 19.1, 18.0, 17.8, 13.1; IR (film): 3347, 2937, 2880, 1756, 1718, 1513, 1374, 1339, 1239, 911, 710 cm$^{-1}$; HRMS-ESI m/z 695.4059 ([M+H]$^+$, C$_{43}$H$_{55}$N$_2$O$_6$ requires 695.4055).

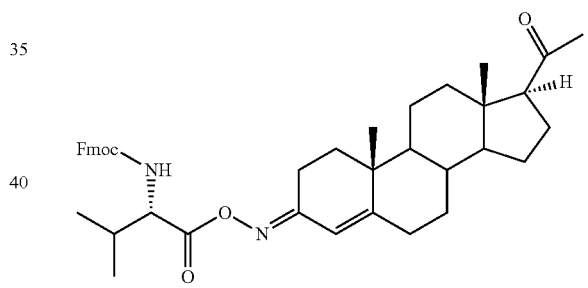

N-Fmoc-valine-3-E-oxime-progesterone (30). Compound 29 (0.265 g, 0.38 1 mmol) was dissolved in 15 mL acetone and 0.0164 g (0.0953 mmol, 0.250 eq) PTSA was added. The reaction was stirred at room temperature for 2 h then heated to 40° C. for 1 h. Ethyl acetate was added and the reaction was concentrated to remove acetone. Ethyl acetate was added and washed with water (2×10 mL). The aqueous layers were combined and extracted with ethyl acetate. The organic layers were combined, washed with brine, dried, and concentrated. The recovered oil was re-dissolved in DCM and prepared as a silica cake with 0.750 g silica. The cake was eluted on a 12 g silica column with a 0-35% EA in hex gradient over 45 minutes. The main product was recovered as 0.245 g (99%) waxy off-white solid. $R_f$=0.52 (1:1 EA/hex, PMA stain); $^1$H NMR (600 MHz, CDCl$_3$) δ 7.77 (d, 2H, J=7.8 Hz), 7.61 (dd, 2H, J=7.2, 2.4 Hz), 7.42-7.39 (m, 2H), 7.32 (t, 2H, J=7.2 Hz), 6.00 (s, 1H), 5.46 (d, 2H, J=9.6 Hz), 4.40-4.40 (m, 3H), 4.24 (t, 1H, J=7.2 Hz), 3.03 (d, 1H, J=17.4 Hz), 2.53 (t, 1H, J=9.6 Hz), 2.37-0.85 (m, 19H), 2.12 (s, 3H), 1.08 (s, 3H), 1.02 (d, 3H, J=7.2 Hz), 0.99 (d, 3H, J=6.6 Hz), 0.65 (s, 3H); $^{13}$C NMR (150 MHz, CDCl$_3$) δ 209.6, 170.1, 164.1, 161.8, 156.4, 144.1, 143.9, 141.5, 127.9, 127.3, 125.3, 120.2, 116.2, 67.4, 63.7, 58.4, 56.3, 53.6, 47.4, 44.1, 38.9, 38.3, 35.8, 34.4, 32.9, 32.1, 31.9, 31.7, 24.6, 23.0, 21.4, 21.0, 19.1, 18.1, 17.8, 13.5; HRMS-ESI m/z 651.3799 ([M+H]$^+$, C$_{41}$H$_{51}$N$_2$O$_5$ requires 651.3793).

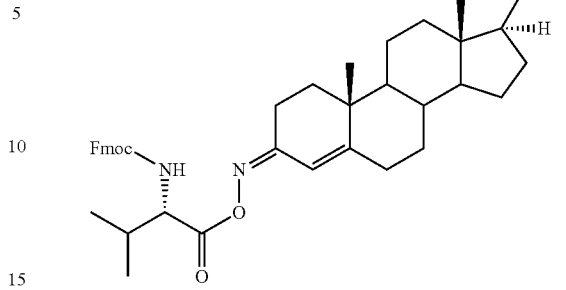

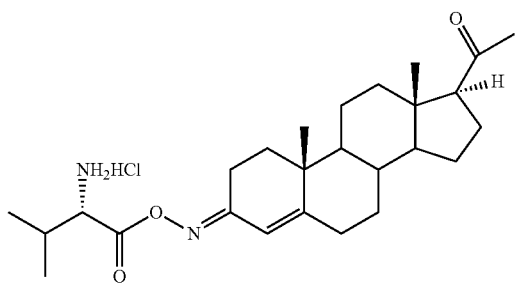

3-Valine-E-oxime-progesterone HCl (P1-185). Oxime compound 30 (0.260 g, 0.400 mmol) was added to an oven dried 50 mL RBF and the flask was evacuated and inert gas flushed. Anhydrous ACN (20 mL) was added and the clear colorless solution was chilled to 0° C. Freshly distilled piperidine (0.395 mL, 4.00 mmol, 10.0 eq) was added and the solution was stirred and allowed to gradually equilibrate to room temperature over 30 mm. The reaction was concentrated with added toluene to give a clear oil. The oil was loaded neat with minimum DCM rinse onto a 12 g silica column and eluted with 0-80% ea in hexane over 40 min. Main product containing fractions were combined and concentrated by rotary evaporation at 10° C. After being brought to complete dryness and re-dissolved in 10 mL ethyl acetate, the sample was concentrated and dried under high vacuum while being chilled in an ice bath. Anhydrous ether (7-8 mL) was added and the clear colorless solution was allowed to cool to 0° C. HCl ether solution (0.195 mL, 2.0 M. 1.0 eq) was added dropwise to the rapidly stirring solution. A white precipitate was observed. The mixture was stirred for 15 minutes at 0° C., then filtered through a 15 mL fine fit glass ground filter and washed with ice chilled anhydrous ether. (67%, two steps) white solid; R$_f$=0.25 (1:1 EA/hex, PMA stain); $^1$H NMR (400 MHz, DMSO) δ 8.71 (bs, 2H), 5.90 (s, 1H), 4.00 (bs, 1H), 3.53 (bs, 1H), 3.03 (d, 1H, J=16.8 Hz), 2.56 (t, 1H, J=9.0 Hz), 2.40-0.79 (m, 20H), 2.06 (s, 3H), 1.05 (s, 3H), 1.02 (d, 3H, J=6.8 Hz), 0.96 (d, 3H, J=6.8 Hz), 0.56 (s, 3H); $^{13}$C NMR (150 MHz, CDCl$_3$) δ209.6, 166.5, 164.8, 162.5, 115.9, 63.7, 58.4, 56.3, 53.6, 44.1, 38.9, 38.3, 35.8, 34.5, 33.0, 32.2, 31.8, 30.3, 24.6, 23.0, 21.5, 19.2, 18.4, 17.9, 15.3, 13.5; IR (solid): 2933, 2874, 2648, 1760, 1699, 1627, 1377, 1358, 1185, 847 cm$^{-1}$; HRMS-ESI m/z 429.3109 ([M-Cl]$^+$, C$_{26}$H$_{41}$N$_2$O$_3$ requires 429.3112); Anal. Calcd for C$_{26}$H$_{41}$ClN$_2$O$_3$+½H$_2$O: C, 65.87; H, 8.93; N, 5.91. Found C, 66.03; H, 8.90; N, 5.83.

The following compounds were prepared according to the methods developed for the E-oxime pro-drug series:

N-Fmoc-valine-3-Z-oxime-20-ketal-progesterone (31). (99%) white foam; R$_f$=0.50 (1:1 EA/hex); $^1$H NMR (600 MHz, CDCl$_3$) δ 7.77 (d, 2H, J=7.8 Hz), 7.62-7.60 (m, 2H), 7.43-7.36 (m, 2H), 7.32 (t, 2H, J=7.2 Hz), 6.33 (s, 1H), 5.45 (d, 1H, J=9.6 Hz), 4.44 (dd, 1H, J=9.0, 4.8 Hz), 4.40 (d, 2H, J=7.2 Hz), 4.24 (t, 1H, J=7.2 Hz), 4.03-3.84 (m, 4H), 2.60-0.74 (m, 21H), 1.30 (s, 3H), 1.12 (s, 3H), 1.04 (d, 3H, J=6.6 Hz), 1.00 (d, 3H, J=7.2 Hz), 0.80 (s, 3H); $^{13}$C NMR (150 MHz, CDCl$_3$) δ 170.2, 165.7, 161.4, 156.4, 144.1, 144.0, 141.5, 127.9, 127.3, 125.3, 120.2, 112.0, 110.8, 67.3, 65.4, 63.4, 58.4, 58.3, 56.0, 54.0, 47.4, 42.1, 39.5, 39.4, 35.7, 35.3, 34.2, 33.5, 32.6, 31.9, 25.8, 23.9, 23.1, 21.1, 19.3, 18.0, 17.9, 13.1; IR (solid): 3318, 2935, 2876, 1716, 1468, 1371, 1309, 1236, 1042, 862, 739 cm$^1$ HRMS-ESI m/z 695.4054 ([M+H]$^+$, C$_{43}$H$_{55}$N$_2$O$_6$ requires 695.4066).

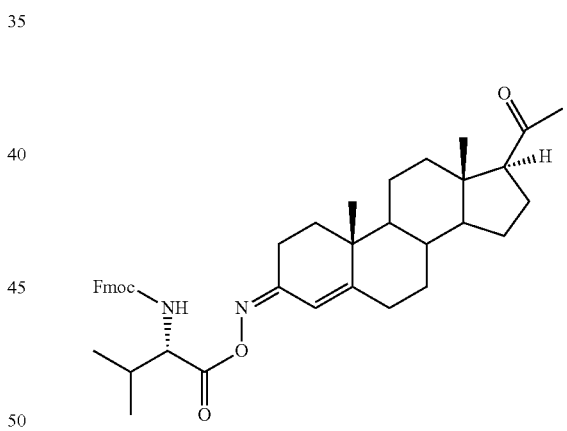

N-Fmoc-valine-3-Z-oxime-progesterone (32). (89%) white foam; R$_f$=0.40 (1:1 EA/hex); $^1$H NMR (400 MHz, CDCl$_3$) δ 7.77 (d, 2H, J=7.6 Hz), 7.61 (dd, 2H, J=7.2, 2.4 Hz), 7.40 (t, 2H, J=7.6 Hz), 7.32 (t, 2H, J=7.6 Hz), 6.35 (s, 1H), 5.47 (d, 1H, J=8.8 Hz), 4.44 (dd, 1H, J=9.2, 4.8 Hz), 4.40 (d, 2H, J=6.8 Hz), 4.24 (t, 1H, J=7.2 Hz), 2.62-0.86 (m, 21H), 2.12 (s, 3H), 1.11 (s, 3H), 1.04 (d, 3H, J=6.8 Hz), 1.00 (d, 3H, J=7.2 Hz), 0.65 (s, 3H); $^{13}$C NMR (150 MHz, CDCl$_3$) δ 209.6, 170.2, 165.1, 161.3, 156.4, 144.1, 143.9, 141.5, 127.9, 127.3, 125.3, 120.2, 110.9, 67.3, 63.7, 58.4, 56.2, 53.8, 47.3, 44.1, 39.3, 38.8, 35.7 (2C), 33.3, 32.5, 31.9, 31.7, 24.7, 24.5, 23.0, 21.2, 19.3, 18.0, 17.9, 13.5; IR (solid): 3327, 2935, 1699, 1449, 1371, 1355, 1235, 1032, 859, 760, 740 cm$^{-1}$; HRMS-ESI m/z 651.3793 ([M+H]$^+$, C$_{41}$H$_{51}$N$_2$O$_5$ requires 651.3793).

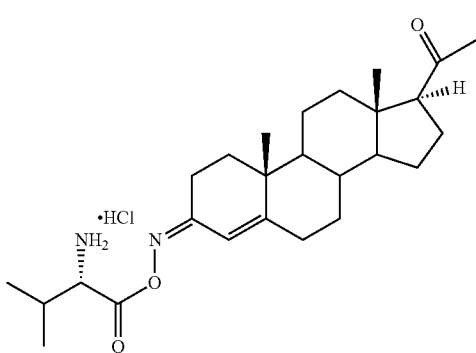 [SMILES: CC(=O)[C@H]1CCC2C3CCC4=C/C(=N\OC(=O)[C@@H](N)C(C)C)CC[C@]4(C)C3CC[C@@]21C ; Cl]

3-Valine-Z-oxime-progesterone HCl (P1-186). (61%, two steps) white solid; $^1$H NMR (400 MHz, DMSO) δ 8.74 (bs, 3H), 6.50 (s, 1H), 3.98 (s, 1H), 3.37 (s, 1H), 2.56 (t, 1H, J=8.8 Hz), 2.48-0.82 (m, 20H), 2.06 (s, 3H), 1.09 (s, 3H), 1.01 (d, 3H, J=7.2 Hz), 0.98 (d, 3H, J=6.4 Hz), 0.56 (s, 3H); $^{13}$C NMR (100 MHz, CDCl$_3$) δ 209.6, 167.0, 166.0, 162.0, 111.3, 63.7, 58.2, 56.2, 53.8, 44.1, 39.3, 38.9, 35.7 (2C), 33.3, 32.5, 31.7, 30.3, 24.7, 24.6, 23.0, 21.3, 19.1, 18.5, 18.1, 13.6; IR (solid): 2935, 1756, 1698, 1620, 1379, 1356, 1185, 852 cm$^{-1}$ HRMS-ESI m/z 429.3108 ([M-Cl]$^1$, $C_{26}H_{41}N_2O_3$ requires 429.3112); Anal. Calcd for $C_{26}H_{41}ClN_2O_3$,+ ½H$_2$O: C, 65.87; H, 8.93; N, 5.91. Found C, 65.44; H, 8.94; N, 5.82.

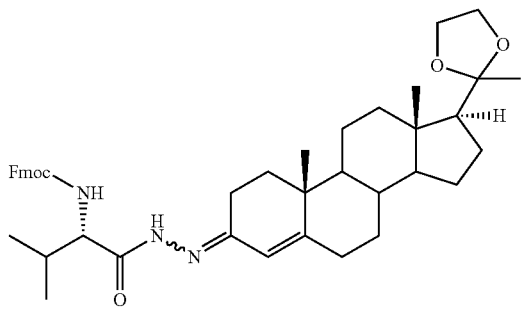

N-Fmoc-valine-3-hydrazide-20-ketal-progesterone (33). Compound 26 (1.79 g, 5.00 mmol) was added to an oven dried 250 mL RBF with 50 mL absolute ethanol. Hydrazine (1.28 mL, 25.0 mmol, 5.00 eq) was added and the reaction was set to reflux overnight. DMF was added and the solution was concentrated (40° C. water bath to 25 mbar). Brine was added and the solution was extracted with EA. The organic layers were combined, washed with brine, dried, filtered, and concentrated. The crude mixture (assumed to be 5.00 mmol), was dissolved in anhydrous DCM and added with N-Fmoc-L-valine (1.87 g, 5.50 mmol, 1.10 eq) and DMAP (0.0611 g, 0.500 mmol, 0.100 eq) to a 250 mL RBF under argon. After complete dissolution of the reaction components, DCC (5.50 mL 1 M soln. in DCM, 5.50 mmol, 1.10 eq) was added. After stirring overnight, the mixture was filtered through Celite. The filtrate was concentrated and prepared as a silica cake that was eluted on a 120 g silica column with 0-45% EA in hex over 45 min. Main peak containing fractions were combined and concentrated to give 1.91 g (55%) off-white solid that was a ~2:1 mixture of the two main products. R$_f$=0.37/0.32 (1:1 EA/hex); major isomer: $^1$H NMR (400 MHz, CDCl$_3$) δ 8.54 (bs, 1H), 7.72-7.16 (m, 8H), 5.80 (s, 1H), 5.65 (d, 1H, J=9.2 Hz), 5.16 (dd, 1H, 9.6, 4.4 Hz), 4.35-3.74 (m, 7H), 2.50-0.64 (m, 21H), 1.30 (s, 3H), 1.06-1.00 (m, 6H), 0.92 (d, 3H, J=6.4 Hz), 0.80 (s, 3H); IR (solid): 3273, 2931, 2874, 1662, 1505, 1240, 1050, 739 cm$^{-1}$; HRMS-ESI m/z 716.4032 ([M+Na]$^+$, $C_{43}H_{55}N_3O_5Na$ requires 716.4045).

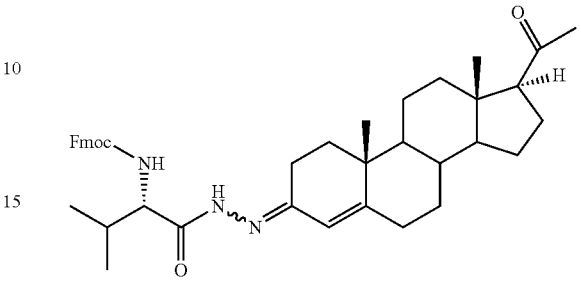

N-Fmoc-valine-3-hydrazide-progesterone (34). Compound 33 (0.732 g, 1.05 mmol) was added to a 15 mL 0.85 M thiourea 1:1 ethanol/water solution. The mixture was heated to reflux overnight. An orange-amber mass of insoluble oily semi-solid had formed. The ethanol was removed and DCM and DI were added. The aqueous layer was extracted with DCM (3×50 mL). The organic layers were combined, washed with brine, dried, filtered, and concentrated with silica. The silica cake was eluted through a 40 g silica column with 0-35% ea in hex over 45 minutes. The desired product(s) were isolated as 0.216 g (32%) off-white solid in a 3:2 mixture of E/Z hydrazides. $^1$H NMR (400 MHz, CDCl$_3$) δ 8.63 (bs, 1H), 7.80-7.25 (m, 8H), 5.87 (s, 1H), 5.67 (d, 1H, J=10.0 Hz), 5.16 (dd, 1H, J=9.6, 4.4 Hz), 4.41-4.16 (m, 3H), 2.60-0.78 (m, 21H), 2.13 (s, 3H), 1.04 (s, 3H), 1.01 (d, 3H, J=6.8 Hz), 0.92 (d, 3H, J=6.8 Hz), 0.65 (s, 3H); IR (solid): 3270, 2931, 1698, 1666, 1505, 1234, 1030, 739 cm$^{-1}$; HRMS-BSI m/z 650.3944 ([M+H]$^+$, $C_{41}H_{52}N_3O_4$ requires 650.3952).

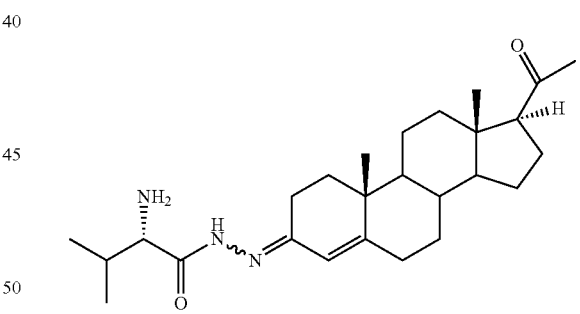

3-Valine-hydrazide-progesterone (35). Compound mixture 34 (0.130 g, 0.200 mmol) was dried in a 25 mL RBF and placed under argon. DMF (5 mL) was added which completely dissolved the substrate. The solution was chilled in an ice bath and piperidine (0.206 mL, 2.00 mmol, 10.0 eq) was added. The ice bath was removed after 15 minutes and the reaction stirred an additional 15 minutes. Ether was added along with brine. The aqueous layer was extracted with ether (4×20 mL). The organic layers were combined, washed with brine, dried, filtered, and concentrated. The sample was loaded in a minimum amount of DCM onto a 12 g silica column and eluted with 0-5% MeOH in DCM over 35 mm (initial 5 mm 100% DCM). Main peak containing fractions were combined and concentrated to give 0.079 g (92%) clear oil. $^1$H NMR (400 MHz, CDCl$_3$) δ 10.20 (bs, 1H), 6.06 (s, 1H), 5.30 (s, 1H), 3.42 (d, 1H, J=3.6 Hz), 2.60-0.78 (m, 22H), 2.11 (s, 3H), 1.06 (s, 3H), 1.01 (d, 3H, J=6.8 Hz), 0.86 (d, 3H, J=6.8 Hz), 0.65 (s, 3H); $^{13}$C NMR (100 MHz, CDCl) δ 209.7, 170.0, 156.9, 154.5, 121.5, 63.8, 60.1, 56.3, 53.6, 44.1, 38.9, 37.9, 35.9, 34.9, 32.5, 32.2, 31.7, 30.8, 24.6, 23.0, 21.6, 20.8, 19.8, 17.9, 16.1, 13.5; IR (solid): 3236, 2933, 2874, 1666, 1385, 1358, 1206, 910, 728 cm$^{-1}$; HIRMS-BSI m/z 428.3268 ([M+H]$^+$, $C_{26}H_{42}N_3O_2$ requires 428.3272).

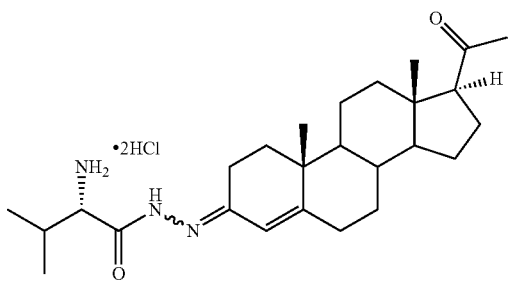 [SMILES: CC(=O)[C@H]1CCC2C3CCC4=CC(=NNC(=O)[C@@H](N)C(C)C)CC[C@]4(C)C3CC[C@@]21C]

3-Valine-hydrazide-progesterone (P2-29). Prepared according to the method described for compound P1-31. (43%) off-white solid; $^1$H NMR (400 MHz, CD$_3$OD) δ 6.59 (s, 1H), 6.16 (s, 1H), 4.62-4.59 (m, 1H), 3.96 (bs, 2H), 3.02-0.86 (m, 23H), 2.12 (s, 3H) 1.24 (d, 3H, J=7.2 Hz), 1.18 (d, 3H, J=6.8 Hz), 1.11 (s, 3H), 0.67 (s, 3H); HRMSBSI m/z 428.3268 ([M+H-2HCl]$^+$, $C_{26}H_{42}N_3O_2$ requires 428.3272); Anal. Calcd for $C_{26}H^4{}_3Cl_2N_3O_2+\frac{1}{2}H_2O$: C, 61.29; H, 8.70; N, 8.25. Found C, 61.57; H, 8.85; N, 8.14.

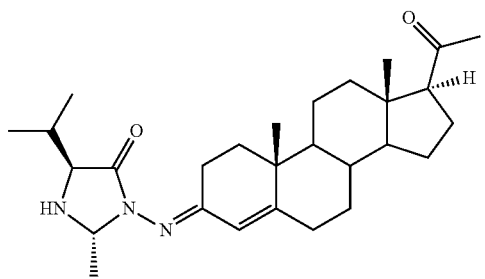 [SMILES: CC(=O)[C@H]1CCC2C3CCC4=C/C(=N/N5C(=O)[C@H](C(C)C)N[C@H]5C)CC[C@]4(C)C3CC[C@@]21C]

(2R,5S)-3-((E)-((10R,13S,17S)-17-acetyl-10,13-dimethyl-7,8,9,11-tetrahydro-1H-cyclopenta[a]phenanthren-3(2H,6H,10H,12H,13H,14H,15H,16H,17H)-ylidene)amino)-5-isopropyl-2-methylimidazolidin-4-one (36). Compound mixture 35 (0.140 g, 0.215 mmol) was dried in a 25 mL RBF and placed under argon. Acetonitrile was added (5 mL) along with DMF (2 mL) to completely dissolve the substrate. The solution was chilled in an ice bath and piperidine (0.213 mL, 2.15 mmol, 10.0 eq) was added. The ice bath was removed after 15 minutes and the reaction stirred an additional 15 minutes. Ethyl acetate was added along with half saturated ammonium chloride solution. The aqueous layer was extracted with EA and the organic layers were combined, washed with brine, dried, filtered, and concentrated. Dichloromethane was added and twice concentrated with the sample. The resulting pale amber oil was loaded in a minimum amount of DCM onto a 12 g silica column run in 0-100% ea in hex over 40 minutes. The two main products were isolated separately as white crystalline solids (87% combined yield). First eluting product: $R_f$=0.32 (95:5 DCM/MeOH); $^1$H NMR (600 MHz, CDCl$_3$) δ 5.99 (s, 1H), 4.81 (q, 1H, J=5.4 Hz), 3.48 (d, 1H, J=3.6 Hz), 2.54-2.48 (m, 1H), 2.40-0.80 (m, 21H), 2.11 (s, 3H), 1.32 (d, 3H, J=5.4 Hz), 1.12 (s, 3H), 1.03 (d, 3H, J=6.6 Hz), 0.94 (d, 3H, J=7.2 Hz), 0.65 (s, 3H); $^{13}$C NMR (150 MHz, CDCl) δ 209.6, 170.5, 170.2, 160.8, 120.7. 73.3, 63.8, 63.7, 56.4, 53.8, 44.1, 39.0, 38.5, 35.8 (2C), 32.7, 32.2, 31.8, 31.7, 25.0, 24.6, 23.0, 21.7, 21.3, 19.7, 17.7, 17.4, 13.5; HRMS-ESI m/z 454.3430 ([M+H]$^+$, $C_{28}H_{44}N_3O_2$ requires 454.3428).

TABLE 3

| Crystal data and structure refinement for compound 36. | |
|---|---|
| Identification code | p2264s |
| Empirical Formula | C28 H42 N3 O2 |
| Formula weight | 452.65 |
| Temperature | 173(2) K |
| Wavelength | 1.54178 Å |
| Crystal system | Monoclinic |
| Space group | C2 |
| Unit cell dimensions | a = 65.281(5) Å  α = 90°. |
|  | b = 5.9668(6) Å  β = 96.847(6)°. |
|  | c = 10.6916(8) Å  γ = 90°. |
| Volume | 4134.8(6) Å$^3$ |
| Z | 4 |
| Density (calculated) | 0.727 Mg/m$^3$ |
| Absorption coefficient | 0.355 mm$^{-1}$ |
| F(000) | 988 |
| Crystal size | 0.42 × 0.07 × 0.03 mm$^3$ |
| Theta range for data collection | 2.73 to 66.48°. |
| Index ranges | −76 <= h <= 73, −6 <= k <= 6, −12 <= l <= 12 |
| Reflections collected | 12330 |
| Independent reflections | 5937 [R(int) = 0.0866] |
| Completeness to theta = 66.48° | 96.0% |
| Absorption correction | Semi-empirical from equivalents |
| Max. and min. transmission | 0.9894 and 0.8651 |
| Refinement method | Full-matrix least-squares on F$^2$ |
| Data/restraints/parameters | 5937/1/306 |
| Goodness-of-fit on F$^2$ | 1.061 |
| Final R indices [I > 2sigma(I)] | R1 - 0.1571, wR2 - 0.3866 |
| R indices (all data) | R1 = 0.2305, wR2 = 0.4236 |
| Absolute structure parameter | 0.6(14) |
| Extinction coefficient | 0.0037(6) |
| Largest diff. peak and hole | 0.470 and −0.465 e. Å.$^{-3}$ |

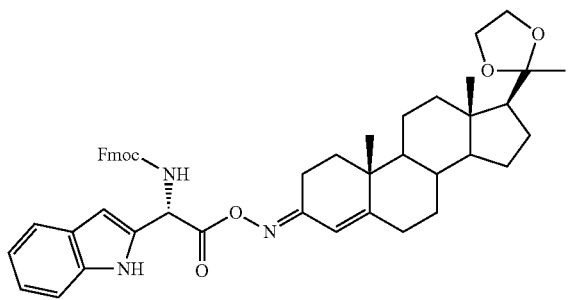

O—N-Fmoc-L-tryptophan-C3-oxime-C20-ketal-progesterone (8a). An oven dried 25 mL RBF was charged with oxime 11 (0.187 g, 0.500 mmol), N-Fmoc-L-tryptophan (0.242 g, 0.22 mmol, 1.05 eq), and DMAP (0.0061 g, 0.021 mmol, 0.10 eq). The flask was sealed, evacuated, and inert gas flushed and 15 mL anhydrous dichloromethane was added, followed after complete dissolution by addition of 0.550 mL (0.23 mmol, 1.10 eq) 1 M DCC in dichloromethane. The solution was stirred for 16 h at room temperature. The mixture was filtered through Celite, the filtrates concentrated, and the crude oil loaded as a silica cake onto 1.17 g silica. The cake was eluted on a 40 g silica column in 0-35% ea in hex over 90 minutes. The main product peak was isolated as 0.383 g (98%) white foam.

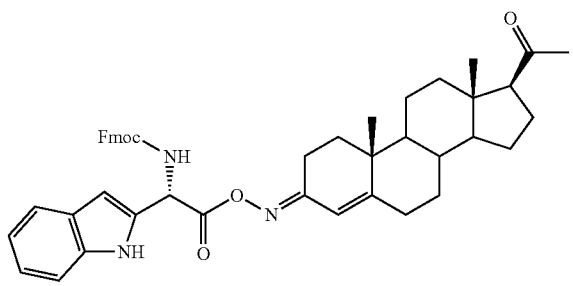

O—N-Fmoc-L-tryptophan-C3-oxime-progesterone (Fmoc 9a). Compound 8a (0.350 g, 0.448 mmol) was dissolved in 15 mL acetone and 0.0193 g (0.112 mmol, 0.250 eq) PTSA was added. The reaction was stirred at room temperature for 2.5 h. Ethyl acetate was added and the solvent was concentrated twice with re-addition of ethyl acetate. The ethyl acetate was washed with water (2×25 mL). The aqueous layers were combined and extracted with ethyl acetate. The organic layers were combined, washed with brine, dried, and concentrated to give a yellow oil that solidified on further drying. The mixture was redissolved in a minimum amount of DCM with toluene and loaded neat onto a 40 g silica column and eluted in a 0-40% ea in hex gradient over 70 minutes to give 0.315 g (95%) pale amber foam.

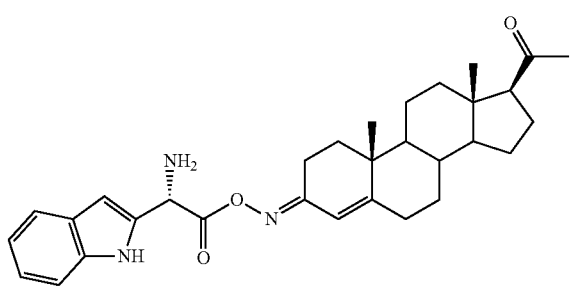 [SMILES: CC(=O)[C@H]1CCC2C3CCC4=C/C(=N/OC(=O)[C@@H](N)c5cc6ccccc6[nH]5)CC[C@]4(C)C3CC[C@@]21C]

O-L-Tryptophan-C3-oxime-progesterone (9a). Compound Fmoc 9a (0.280 g, 0.379 mmol) was added to an oven dried 25 mL RBF. Anhydrous acetonitrile (7.5 mL) was added, followed by piperidine (0.141 mL, 1.42 mmol, 10.0 eq). The reaction was stirred for 30 minutes at room temperature. The solvent was removed by evaporation and the crude oil redissolved in toluene and reduced to dryness twice in succession. The crude off-white solid was redissolved in a minimum amount of DCM, loaded neat onto a 12 g silica column, and eluted with a 0-95% ea in hex gradient over 60 min. The main product was obtained as 0.120 g (61%) off-white solid.

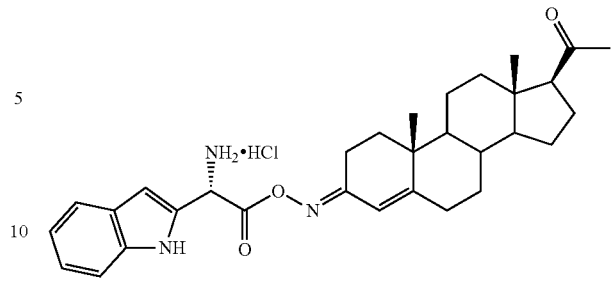

O-L-Tryptophan-C3-oxime-progesterone HCl salt (P1-79). Compound 14 (46 mg, 0.089 mmol) was dissolved in 2.5 mL anhydrous ether in a 10 mL RBF under argon. The solution was chilled in an ice bath and 0.195 mL 1 M HCl solution in ether was added. A white precipitate was observed to have immediately formed in solution. The mixture was filtered and the precipitate was washed with cold ether to give 21 mg (43%) white solid.

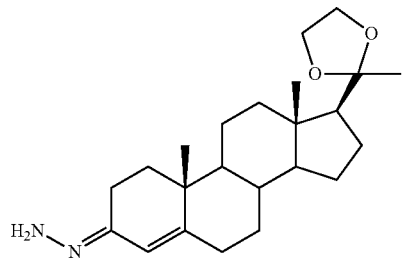 [SMILES: CC1([C@H]2CCC3C4CCC5=C/C(=N/N)CC[C@]5(C)C4CC[C@@]32C)OCCO1]

3-Hydrazine-20-ketal-progesterone (10). Compound 6 (0.377 g, 95% w/w, 1.00 mmol) was added to an oven dried 25 mL RBF and 5 mL absolute ethanol was added. Hydrazine (5.00 mL 1.0 M solution in THF, 5.00 mmol, 5.00 eq) was added which served to completely dissolve the starting material. This was stirred at room temperature for 1.5 h and set to reflux overnight. The solution was concentrated and dried under vacuum to give a white foam. Dichloromethane was added and the solution was re-concentrated to generate a solid that was filtered and washed with 3:1 hex/ether to give 0.164 g (44%) pale yellow crystals.

Example 6

Allopregnanolone Derivatives

Scheme 16 below shows the synthesis of C3 ALLO valine derivatives. Other C3 amino acid ALLO derivatives may be prepared with similar reagents and conditions.

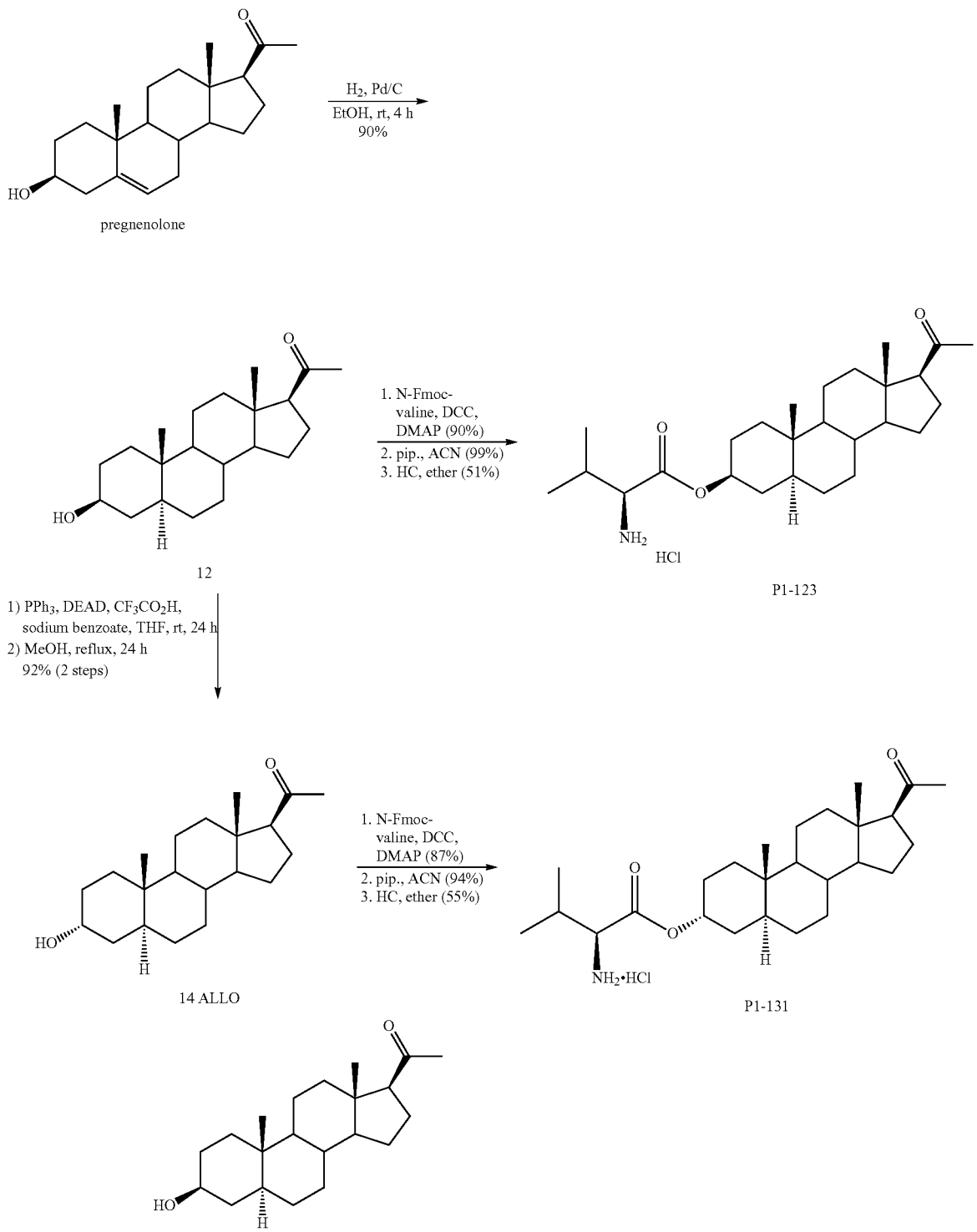

Scheme 16

3β-hydroxy-5α-pregnan-20-one (12). An oven dried 500 mL RBF was charged with 10% palladium on carbon (0.400 g) and 5-pregnen-3-beta-ol-20-one (4.00 g, 12.6 mmol) and the flask was evacuated and flushed with argon. A 200 mL volume of absolute ethanol was added and the flask was flushed with hydrogen. The reaction was stirred at room temperature for 4 h. The mixture was filtered through Celite and the recovered clear, colorless filtrate was concentrated to reveal a white solid of mass 4.08 g. The solid was recrystallized from hexane/ethyl acetate (~3:1 total 175 mL) to give 3.19 g white solid. A second recrystallization provided an additional 0.43 g for a total of 3.62 g (90%) white crystalline solid.

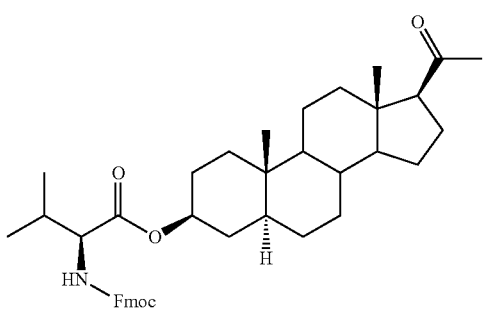

3β-N-Fmoc-L-valine-5α-pregnan-20-one (Fmoc 13a). An oven dried 25 mL RBF was charged with compound 20 (0.318 g, 1.00 mmol), N-Fmoc-L-valine (0.356 g, 1.05 mmol, 1.05 eq) and DMAP (12 mg, 0.100 mmol, 0.10 eq). The flask was sealed, evacuated and inert gas flushed, and 9 mL anhydrous DCM was added, followed after complete substrate dissolution by 1.10 mL (1.10 mmol, 1.10 eq) 1.0 M DCC in DCM. The reaction mixture was stirred at room temperature for 24 h. The mixture was filtered through Celite and rinsed with DCM. The sample was prepared as a silica cake and eluted on a 40 g silica column with 0-25% ea in hex over 45 min. Main product containing fractions were combined and isolated as 0.578 g (90%) white foam.

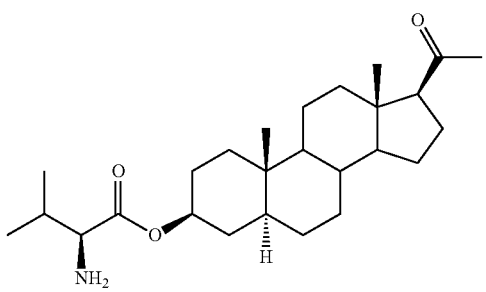 [SMILES: CC(=O)[C@H]1CCC2C3CC[C@H]4C[C@@H](OC(=O)[C@@H](N)C(C)C)CC[C@]4(C)C3CC[C@@]21C]

3β-L-valine-5α-pregnan-20-one (13a). A 25 mL RBF was charged with compound Fmoc 13a (0.488 g, 0.725 mmol) and 7.5 mL acetonitrile. Piperidine (0.716 mL, 7.25 mmol, 10.0 eq) was added and the solution was stirred at room temperature for 30 min. Toluene was added and the solution was concentrated 3 times with addition of toluene. The resulting white solid was redissolved in a minimum amount of toluene and loaded onto a 12 g silica column. The column was eluted with 0-100% ea in hex over 40 minutes. The main product was obtained as 0.317 g (99%) clear/white semi-solid.

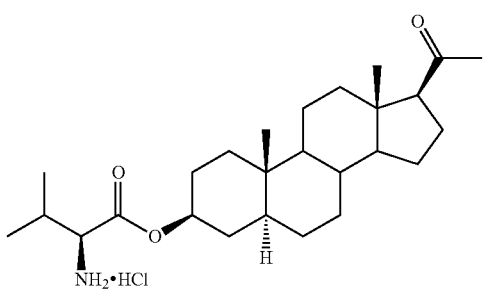

3β-L-valine-5α-pregnan-20-one HCl salt (P1-123). Compound 22 (0.317 g, 0.759 mmol) was dissolved in ~2:1 anhydrous ether/DCM (6 mL total) under argon. The clear, slightly amber solution was chilled in an ice bath and 0.759 mL (0.759 mmol, 1.0 eq) 1 M HCl in ether solution was added slowly dropwise. A white precipitate was observed in solution. The solution was stirred at 0° C. for 30 min and then filtered. The precipitate was washed with ice chilled ether. The product was recovered as a slightly off-white solid of mass 0.175 g (51%).

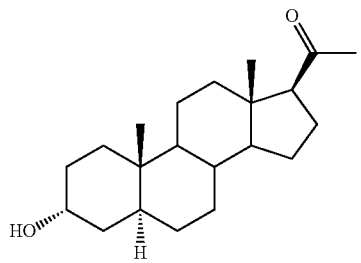 [SMILES: CC(=O)[C@H]1CCC2C3CC[C@H]4C[C@H](O)CC[C@]4(C)C3CC[C@@]21C]

3α-hydroxy-5α-pregnan-20-one (14). An oven dried 100 mL RBF with magnetic stir bar was charged with 1.59 g (5.00 mmol) compound 20 and 15 mL anhydrous THF. Diethylazodicarboxylate (2.85 mL 40% soln. in toluene, 6.25 mmol, 1.25 eq) was added, followed by trifluoroacetic acid (0.482 mL, 6.25 mmol, 1.25 eq) and the flask was set in a room temperature water bath. To this pale amber suspension was added triphenylphosphine (1.64 g, 6.25 mmol, 1.25 eq). Sodium benzoate (0.901 g, 6.25 mmol, 1.25 eq) was then added and the suspension was stirred under argon for 24 h at room temperature. The THF was completely removed with methanol addition/evaporation. Methanol (20 mL) was then added. The flask was fitted with a drying tube topped condenser and set for reflux. After 24 h, the methanol was removed and the remaining solid was redissolved in DCM. The organic layer was washed with DI (3×20 mL). The aqueous layers were combined and extracted with DCM. The organic layers were combined, dried, filtered, and concentrated to give a white solid. The solid was prepared as a silica cake and eluted with 0-35% ea in hex on a 120 g silica column over 40 min. Main product containing fractions were combined and concentrated to give 1.46 g (92%) white solid.

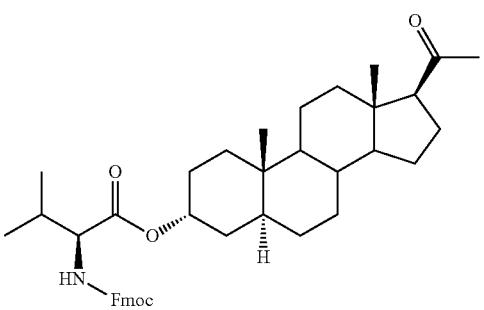

3α-N-Fmoc-L-valine-5α-pregnan-20-one (Fmoc 15a). An oven dried 50 mL RBF was charged with compound 14 (0.478 g, 1.50 mmol), N-Fmoc-L-valine (0.535 g, 1.58 mmol, 1.05 eq), and DMAP (18 mg, 0.150 mmol, 0.10 eq). The flask was sealed, evacuated and inert gas flushed, and 15 mL anhydrous DCM was added, followed after complete substrate dissolution by 1.65 mL (1.65 mmol, 1.10 eq) 1.0 M DCC in DCM. The flask was stirred at room temperature for 24 h. The mixture was filtered through Celite and rinsed with DCM. Silica (~3 g) was added and the mixture was concentrated. The silica cake was eluted on a 40 g silica column with 0-25% ea in hex over 45 min. The main product was isolated as 0.834 g (87%) white foam.

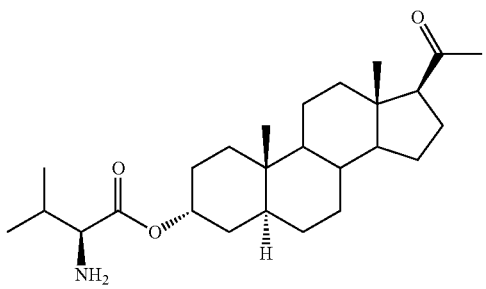 [SMILES: CC(=O)[C@H]1CCC2C3CC[C@H]4C[C@H](OC(=O)[C@@H](N)C(C)C)CC[C@]4(C)C3CC[C@@]21C]

3α-L-Valine-5α-pregnan-20-one (15a). A 25 mL RBF was charged with compound Fmoc 15a (0.320 g, 0.500 mmol), 5 mL ACN, and 3 mL DMF. Piperidine (0.494 mL, 5.00 mmol, 10.0 eq) was added. The solution was stirred at room temperature for 30 minutes. Toluene was added and the solution was concentrated 3 times with addition of toluene. The pale amber oil was loaded in a minimum amount of toluene onto a 12 g silica column. The column was eluted with 0-100% ea in hex over 40 minutes. Main product fractions were combined to give 0.196 g (94%) sticky white solid.

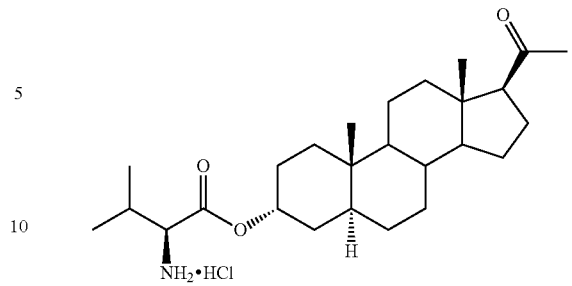

3α-L-Valine-5α-pregnan-20-one HCl salt (P1-131). Compound 25 (0.251 g, 0.600 mmol) was dissolved in 6 mL anhydrous ether under argon. The clear solution was chilled in an ice bath and 0.300 mL (0.600 mmol, 1.0 eq) 2.0 M HCl/ether solution was added slowly dropwise. A white precipitate was observed in solution. The solution was stirred at 0° C. for 30 min and then filtered. The precipitate was washed with ice chilled ether. The product was recovered as 0.150 g (55%) slightly off-white solid.

Scheme 17 below shows the synthesis of 5β ALLO isomers 17a and 17b and C3 valine derivatives of the isomers. The isomers 17a and 17b were separated by conventional chromatography and carried forward as described above to prepare the valine derivatives P1-133 and P1-135. Derivatives with other amino acids may be prepared from compounds 17a and 17b using similar reagents and conditions.

Scheme 17

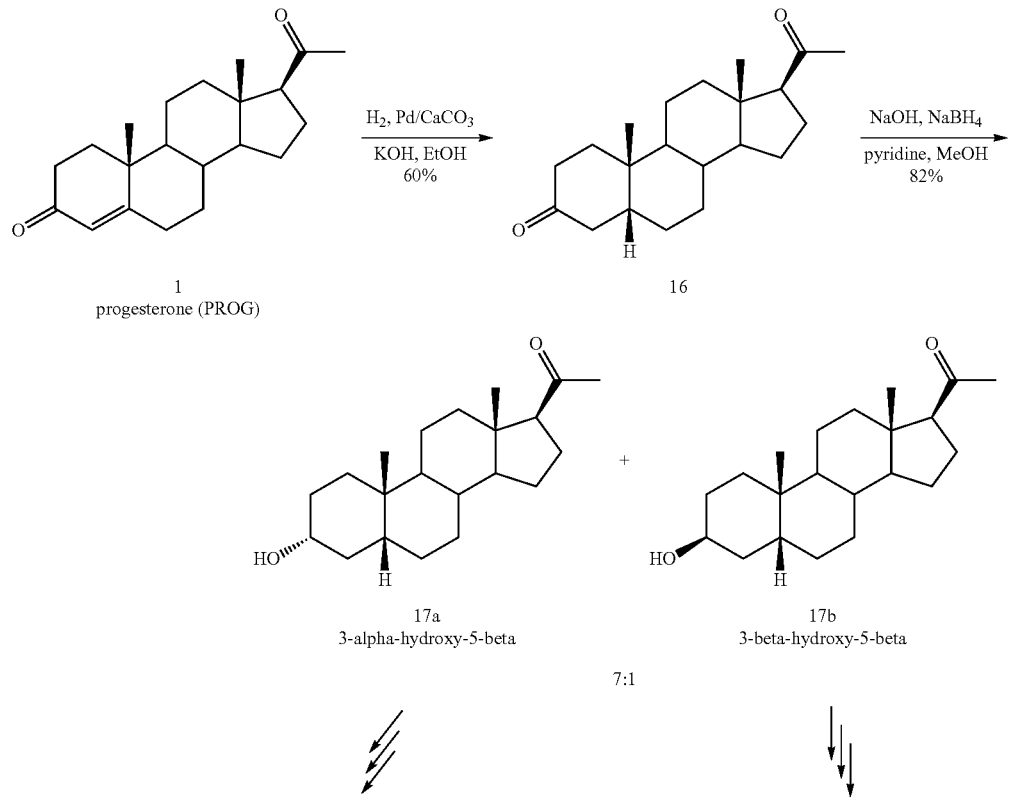

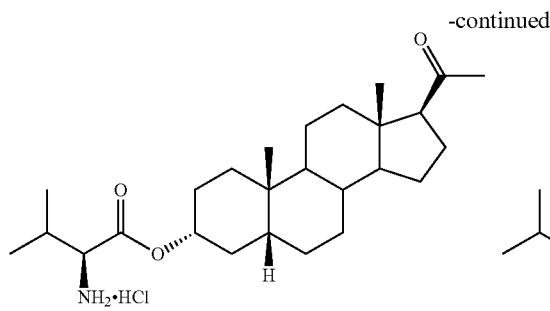

P1-133

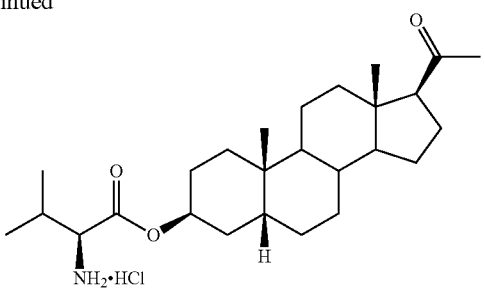

P1-135

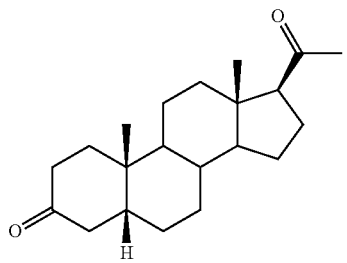

5β-Pregnane-3,20-dione (16). A three necked 500 mL RBF was charged with progesterone (2.00 g, 6.36 mmol), 5% Pd/CaCO₃ (0.180 g, 9% w/w), 200 mL absolute ethanol, and KOH (0.360 g in 1 mL DI). The flask was evacuated and flushed with hydrogen and the reaction stirred for 1 h. The ethanol was removed and the residue was redissolved in ether and washed with water. The water layer was extracted with ether (2×50 mL). The aqueous layer was then acidified to pH<3 with 1 M HCl and extracted with ether. The organic layers were combined, dried, filtered, and concentrated to give an off-white solid of mass 2.08 g. The sample was loaded in a minimum amount of toluene onto a 120 g silica column and eluted with 0-35% ea in hex gradient. The main product was recovered as 1.20 g (60%) white solid.

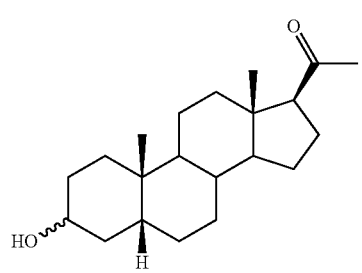 [SMILES: CC(=O)[C@H]1CCC2C3CC[C@@H]4CC(O)CC[C@]4(C)C3CC[C@@]21C]

3-Hydroxy-5β-pregnane-20-one (17a/17b). A 250 mL RBF was charged with compound 26 (1.00 g, 3.16 mmol) and 40 mL absolute ethanol. The solution was warmed in an oil bath to 50° C. and sodium borohydride (0.179 g, 4.74 mmol, 1.50 eq) was added. The reaction was stirred for 10 min and 75-100 mL hot water was added until a slight cloudiness remained in solution. The solution was then allowed to cool gradually to room temperature and chilled in a 4° C. freezer for 3 h. The mixture was filtered and the white solid was washed with 30% ethanol in DI. After drying, the recovered solids were loaded in a minimum amount of DCM onto a 120 g silica column and eluted with 0-25% ea/hex over 60 min. Main product containing fractions were combined and concentrated to give 0.710 g (71%) 3α-hydroxy-5β-pregnane-20-one and 0.110 g (11%) 3β-hydroxy-3β-pregnane-20-one isomer.

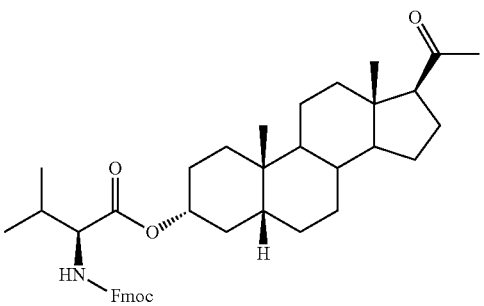

3α-N-Fmoc-L-valine-5β-pregnane-20-one (Fmoc 18a). An oven dried 25 mL RBF was charged with compound 27 (0.333 g, 1.05 mmol), N-Fmoc-L-valine-OH (0.373 g, 1.10 mmol, 1.05 eq), and DMAP (12.8 mg, 0.10 mmol, 0.10 eq). The flask was sealed, evacuated and inert gas flushed and 9 mL anhydrous DCM was added, followed after complete substrate dissolution by 1.15 mL (1.15 mmol, 1.10 eq) 1.0 M DCC in DCM. A white precipitate appeared in solution during DCC addition. The flask was stirred at room temperature for 24 h. The mixture was filtered through Celite and rinsed with DCM. The filtrate was concentrated with 2 g silica and the silica cake was eluted on a 40 g silica column with 0-25% ea in hex over 45 min. The main product was recovered as 0.541 g (81%) white foam.

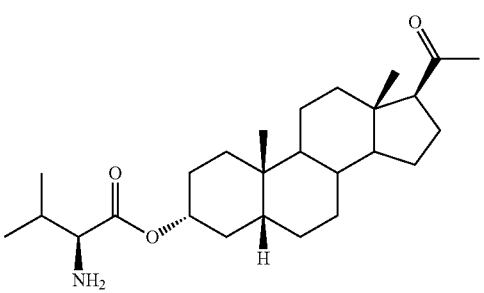 [SMILES: CC(=O)[C@H]1CCC2C3CC[C@@H]4C[C@H](OC(=O)[C@@H](N)C(C)C)CC[C@]4(C)C3CC[C@@]21C]

3α-L-valine-5β-pregnane-20-one (18a). A 25 mL RBF was charged with compound Fmoc 18a (0.500 g, 0.742 mmol) and 7 mL ACN. Piperidine (0.733 mL, 7.42 mmol, 10.0 eq) was added and the solution was stirred at room temperature for 30 minutes. A flaky white precipitate appeared in solution. The precipitate was filtered and washed with ACN. The organic layers were combined with toluene and the solution was concentrated 3 times with addition of toluene. The white solid was redissolved in a minimum amount of toluene and loaded onto a 12 g silica column. The column was eluted with 0-75% ea in hex over 40 minutes. The main product was isolated as 0.301 g (97%) white solid.

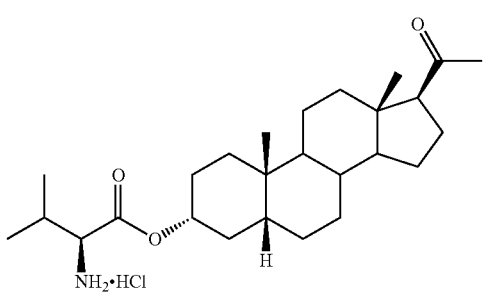

3α-L-Valine-5β-pregnane-20-one HCl salt (P1-133). Compound 30 (0.155 g, 0.371 mmol) was dissolved in 4 mL anhydrous ether under argon. The clear solution was chilled in an ice bath and 0.186 mL (0.371 mmol, 1.0 eq) 2 M HCl in ether solution was added slowly dropwise. A white precipitate was observed in solution. The solution was stirred at 0° C. for 30 minutes and then filtered. The precipitate was washed with ice chilled 2:1 hex/ether. The product was recovered as a slightly off-white solid of mass 0.120 g (71%).

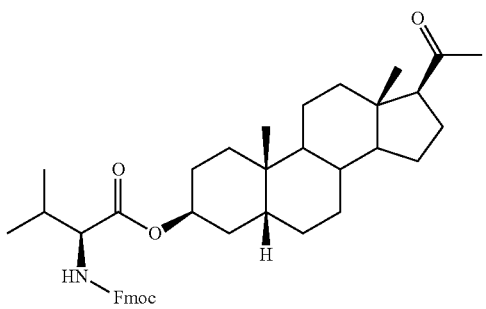

3β-N-Fmoc-L-valine-5β-pregnane-20-one (Fmoc 18b). An oven dried 25 mL RBF was charged with compound 28 (0.234 g, 0.735 mmol), N-Fmoc-L-valine (0.262 g, 1.10 mmol, 1.05 eq) and DMAP (9 mg, 0.10 mmol, 0.10 eq). The flask was sealed, evacuated and inert gas flushed, and 8 mL anhydrous DCM was added, followed after complete substrate dissolution by 0.808 mL (0.808 mmol, 1.10 eq) 1.0 M DCC in DCM. The flask was stirred at room temperature for 24 h. The mixture was concentrated with 1.5 g silica, and the silica cake was eluted on a 40 g silica column with 0-25% ea in hex over 45 min. The main product was isolated as 0.345 g (73%) white foam.

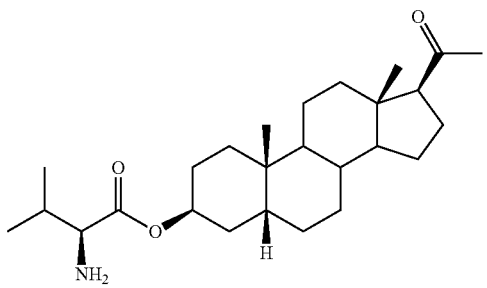 [SMILES: CC(=O)[C@H]1CCC2C3CC[C@@H]4C[C@@H](OC(=O)[C@@H](N)C(C)C)CC[C@]4(C)C3CC[C@@]21C]

3β-L-Valine-5β-pregnane-20-one (18b). A 25 mL RBF was charged with compound 31 (0.307 g, 0.456 mmol) and dissolved in 7 mL ACN. Piperidine (0.450 mL, 4.56 mmol, 10.0 eq) was added and the solution was stirred at room temperature for 15 minutes. The precipitate was filtered and washed with ACN. The organic layers were combined with toluene and the solution was concentrated 3 times. The white solid was redissolved in a minimum amount of toluene, loaded onto a 12 g silica column, and eluted with 0-75% ea in hex over 35 minutes. The product was obtained as 0.176 g (93%) white foam.

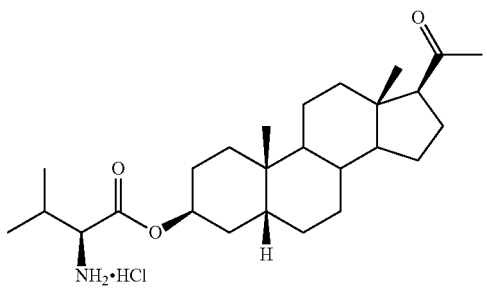

3β-L-Valine-5β-pregnane-20-one HCl salt (P1-135). Compound 32 (0.123 g, 0.290 mmol) was dissolved in 3 mL anhydrous ether under argon. The clear solution was chilled in an ice bath and 0.15 mL (0.29 mmol, 1.0 eq) 2 M HCl in ether solution was added slowly dropwise. A white precipitate was observed in solution. The solution was stirred at 0° C. for 30 minutes and then filtered. The precipitate was washed with ice chilled 2:1 hex/ether. The product was recovered as a slightly off-white solid of mass 0.052 g (39%).

Enantiomeric Progesterone Synthesis

The following compounds were prepared according to previously published methods (Micheli et al., *J. Org. Chem.*, 1975, 40, 675-681; Hajos et al., *J. Org. Chem.*, 1973, 38, 3239-3243; Hajos et al., *J. Org. Chem.*, 1973, 38, 3244-3249; Rychnovsky et al. *J. Org. Chem.*, 1992, 57, 2732-2736).

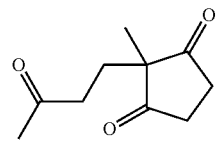

2-Methyl-2-(3-oxobutyl)-1,3-cyclopentanedione (38). (95%) amber oil; $R^f$=0.62 (95:5 DCM/MeOH); $^1$H NMR (400 MHz, CDCl$_3$) δ 2.87-2.69 (m, 4 H), 2.43 (t, 2 H, J=7.2), 2.08 (s, 3 H), 1.86 (t, 2 H, J=7.2), 1.09 (s, 3 H); $^{13}$C NMR (100 MHz, CDCl$_3$) δ 216.0 (2 C), 208.1, 55.3, 37.6, 34.9 (2 C), 30.2, 27.9, 19.2; IR (film): 2930, 1712, 1366, 1169; HRMS-ESI m/z 183.1014 ([M+H]+ C$_{10}$H$_{15}$O$_3$ requires 183.1016).

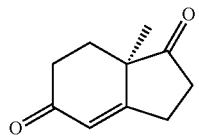

(R)-7a-Methyl-2,3,7,7a-tetrahydro-6H-indene-1,5-dione (39). (80%) pale tan solid; R$_f$=0.47 (95:5 DCM/MeOH); $^1$H NMR (400 MHz, CDCl$_3$) δ 5.95 (d, 1H, J=2.4), 3.00-2.90 (m, 1H), 2.82-2.70 (m, 2H), 2.56-2.37 (m, 3H), 2.09 (ddd, 1H, J=13.6, 2.4, 2.0), 1.83 (dt, 1H, J=136, 5.2), 1.30 (s, 3H); $^{13}$C NMR (100 MHz, CDCl$_3$) δ 216.8, 198.4, 170.0, 124.0, 48.9, 36.0, 33.0, 29.3, 27.0, 20.7; IR (solid): 2970, 2876, 1742, 1699, 1660, 1447, 1146 cm$^{-1}$; HRMS-ESI m/z 165.0911 ([M+H]$^+$, C$_{10}$H$_{13}$O$_2$ requires 165.0910).

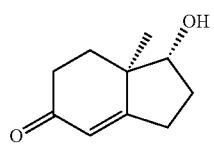

(1R,7aR)-1-Hydroxy-7a-methyl-1,2,3,6,7,7a-hexahydro-inden-5-one (40). (94%) amber semisolid; R$_f$=0.17 (95:5 DCM/MeOH); $^1$H NMR (400 MHz, CDCl$_3$) δ 5.78 (s, 1H), 3.84 (t, 1H, J=8.8 Hz), 2.75-2.64 (m, 1H), 2.57-2.33 (m, 4H), 2.17-2.07 (m, 2H), 1.88-1.72 (m, 2H), 1.14 (s, 3H); $^3$C NMR (100 MHz, CDCl$_3$) δ 199.7, 175.6, 123.5, 80.7, 45.4, 34.2, 33.5, 29.2, 26.6, 15.3; IR (film): 3335 (br), 2935, 1632, 1326, 1221, 1075 cm$^{-1}$; HRMS-ESI m/z 167.1068 ([M+H]$^+$, C$_{10}$H$_{15}$O$_2$ requires 167.1067).

(1R,7aR)-1-tert-Butoxy-7a-methyl-1,2,3,6,7,7a-hexahydro-inden-5-one (41). (84%) pale yellow solid; R$_f$=0.48 (95:5 DCM/MeOH); $^1$H NIMR (400 MHz, CDCl$_3$) δ 5.75 (s, 1 H), 3.56 (dd, 1 H, J=9.6, 7.6 Hz), 2.72-2.63 (m, 1 H), 2.55-2.47 (m, 1 H), 2.46-2.31 (m, 2 H), 2.05-1.93 (m, 2 H), 1.84-1.67 (m, 2 H), 1.17 (s, 9 H), 1.10 (s, 3 H); $^{13}$C NMR (100 MHz, CDCl$_3$) δ 199.7, 175.8, 123.1, 79.8, 73.2, 45.0, 34.5, 33.6, 29.7, 28.8 (3C), 27.0, 15.9; IR (solid): 2972, 1669, 1361, 1198, 1089 cm$^{-1}$; HRMS-ESI m/z 223.1691 ([M+H]$^+$, C$_{14}$H$_{23}$O$_2$ requires 223.1693).

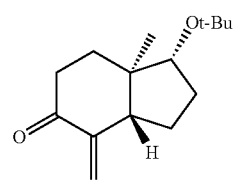 [SMILES: C=C1C(=O)CC[C@]2(C)[C@@H]1CC[C@H]2OC(C)(C)C]

(–)-(1R,7aR)-5,6,7,7a-Tetrahydro-1-tert-butoxy-7a-methyl-5-oxo-4-indancarboxylic acid (43). (71%) brown-yellow solid; R$_f$=0.21 (DCM/EA); [α]$^{23}_D$–31.1 (c=1.00, CHCl$_3$) [lit. –37 (c=1.02 CHCl$_3$)]$^{129}$ $^1$H NMR (400 MHz, CDCl$_3$) δ 3.67 (dd, 1H, J=10.2, 7.2 Hz), 3.33-3.15 (m, 2H), 2.84-2.61 (m, 2H), 2.12-2.03 (m, 2H), 1.93-1.77 (m, 2H), 1.19 (s, 12H); $^{13}$C NMR (100 MHz, CDCl$_3$) δ 203.1, 196.5, 164.5, 120.5, 78.9, 73.7, 48.5, 33.7, 32.1, 31.6, 30.1, 28.8 (3C), 16.5; IR (solid): 2967, 2750, 1732, 1625, 1599, 1437, 1190, 1099 cm$^{-1}$; HRMS-ESI m/z 267.1588 ([M+H]$^+$, C$_{15}$H$_{23}$O$_4$ requires 267.1591).

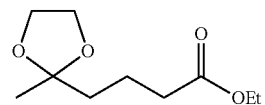

(–)-(1R,3aS,7aR)-1-tert-Butoxy-7a-methyl-3a,6,7,7a-tetrahydro-4-methyleneindan-5(4H)-one (45). (79%) brown oil; $^1$H NMR (400 MHz, CDCl$_3$) δ 5.93 (q, 1H, J=2.8, 1.6 Hz), 5.01 (q, 1H, J=2.4, 1.6 Hz), 3.64-3.57 (m, 1H), 2.59-1.48 (m, 9H), 1.16 (s, 9H), 0.78 (s, 3H); $^{13}$C NMR (100 MHz, CDCl$_3$) δ 202.5, 147.5, 118.3, 80.2, 72.8, 49.1, 43.3, 36.2, 34.1, 31.9, 28.9 (3C), 22.9, 11.4; IR (film): 2970, 2874, 1694, 1361, 1191, 1090 cm$^{-1}$; HRMS-ESI m/z 237.1847 ([M+H]$^+$, C$_{15}$H$_{25}$O$_2$ requires 237.1849).

5-[(1,3-Dioxolan-2-yl)ethyl]hexanoate (47). (93%) pale amber oil; R$_f$=0.40 (2:1 hex/EA, PMA stain); $^1$H NMR (400 MHz, CDCl$_3$) δ 4.12 (q, 2H, J=7.2 Hz), 3.96-3.91 (m, 4H), 2.32 (t, 2H, J=7.2 Hz), 1.78-1.64 (m, 4H), 1.32 (s, 3H), 1.25 (t, 3H, J=7.2 Hz); $^{13}$C NMR (100 MHz, CDCl$_3$) δ 173.7, 109.9, 64.8 (2C), 60.4, 38.5, 34.5, 24.0, 19.8, 14.4; IR (neat): 2981, 2880, 1731, 1375, 1176, 1050, 855 cm$^{-1}$; HRMS-ESI m/z 203.11277 ([M+H]$^+$, C$_{10}$H$_{19}$O$_4$ requires 203.1278).

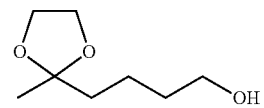

5-(1,3-Dioxolan-2-yl)hexanol (48). (99%) clear oil; R$_f$=0.14 (1:1 hex/EA, PMA stain);
$^1$H NIMR (600 MHz, CDCl$_3$) δ 3.97-3.91 (m, 4H), 3.65 (t, 2H, J=6.6 Hz), 1.69-1.66 (m, 2H), 1.61-1.56 (m, 3H), 1.50-1.45 (m, 2H), 1.32 (s, 3H); $^{13}$C NMR (150 MHz, CDCl$_3$) δ 110.2, 64.8 (2C), 63.0, 39.0, 33.0, 24.0, 20.4; IR (neat): 3417 (br), 2942, 2873, 1376, 1220, 1139, 1037 cm$^{-1}$; HRMS-ESI m/z 160.13330 ([M-OH+NH$_3$]$^+$, C$_8$H$_{18}$NO$_2$ requires 160.1332).

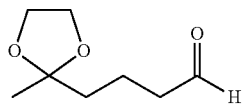

5-(1,3-Dioxolan-2-yl)hexanal (49). (81%) amber oil; R$_f$=0.37 (1:1 hex/EA, PMA stain); $^1$H NMR (400 MHz, CDCl$_3$) δ 9.75 (t, 1H, J=1.6 Hz), 3.97-3.88 (m, 4H), 2.46 (dt, 2H, J=7.2, 1.6 Hz), 1.79-1.64 (m, 4H), 1.31 (s, 3H); $^{13}$C NMR (100 MHz, CDCl) δ 202.6, 109.8, 64.8 (2C), 44.0, 38.4, 24.0, 16.8; IR (film): 2982, 2881, 1721, 1376, 1211, 1068, 852 cm$^{-1}$; HRMS-ESI m/z 159.1014 ([M+H]$^+$, C$_8$H$_{15}$O$_3$ requires 159.1016).

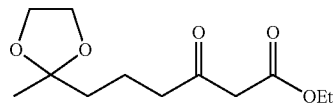 [SMILES: CCOC(=O)CC(=O)CCCC1(C)OCCO1]

Ethyl 7-(1,3-Dioxolan-2-yl)-3-oxooctanoate (50). (78%) pale green-amber oil; $^1$H NMR (600 MHz, CDCl$_3$) δ 4.19 (q, 2H, J=7.2 Hz), 3.95-3.91 (m, 4H), 3.43 (s, 2H), 2.58 (t, 2H, J=7.2 Hz), 1.74-1.63 (m, 4H), 1.31 (s, 3H), 1.28 (t, 3H, J=7.2 Hz); '$^{13}$C NMR (150 MHz, CDCl$_3$) δ 202.8, 167.5, 110.0, 64.8 (2C), 61.5, 49.5, 43.0, 38.2, 23S, 18.2, 14.3 cm$^{-1}$.

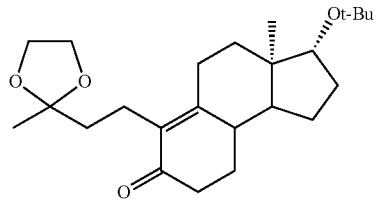 [SMILES: CC(C)(C)O[C@@H]1CCC2C3CCC(=O)C(CCC4(C)OCCO4)=C3CC[C@]21C]

(−)-3α-tert-Butoxy-3aα-methyl-1,2,3,3a,4,5,8,9,9aβ, 9ba-dodecahydro-6-[2-(2-methyl-1,3-dioxolan-2-yl)-ethyl]-7H-benz[e]inden-7-one (51). (72%) brown oil; $^1$H NMR (400 MHz, CDCl$_3$) δ 3.98-3.91 (m, 4H), 3.40 (t, 1H, J=8.4 Hz), 2.84-2.75 (m, 1H), 2.50-1.04 (m, 17H), 1.14 (s, 9H), 0.88 (s, 3H); $^{13}$C NMR (100 MHz, CDCl) δ 199.2, 160.2, 134.1, 110.0, 80.4, 72.7, 64.8 (2C), 51.0, 42.2, 39.1, 38.2, 37.2, 36.8, 31.3, 28.9 (3C), 26.9, 26.8, 24.1, 23.7, 20.3, 11.1; IR (film): 2970, 2872, 1663, 1361, 1194, 1095, 1058 cm$^{-1}$; HRMS-ESI m/z 391.2837 ([M+H]$^+$, C$_{24}$H$_{39}$O$_4$ requires 391.2843).

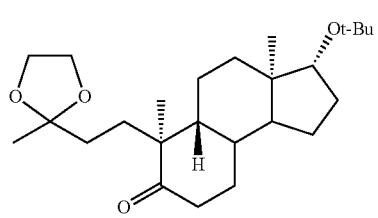

(−)-3β-ter-Butoxy-3aβ,5aβ-dimethyl-1,2,3,3a,4,5,5a,6, 8,9,9aβ,9a-dodecahydro-6-[2-(2-methyl-1,3-dioxolan-2-yl)-ethyl]-7H-benz[c]inden-7-one (52). (53%) brown oil; $^1$H NMR (400 MHz, CDCl) δ 3.98-3.91 (m, 4H), 3.37 (1, 1H, J=8.4 Hz), 2.61-2.40 (m, 1H), 2.28-2.19 (m, 1H), 1.96-0.90 (m, 17H), 1.36 (s, 3H), 1.13 (s, 9H), 1.10 (s, 3H), 0.78 (s, 3H); $^{13}$C NMIR (100 MHz, CDCl$_3$) δ 215.1, 110.5, 80.8, 72.5, 64.7, 64.7, 50.8, 50.6, 47.8, 42.7, 38.3, 36.9, 35.0, 33.2, 31.2, 31.0, 29.2, 28.9 (3C), 24.0, 23.6, 21.4, 21.1, 11.8; IR (film): 2967, 2937, 1703, 1360, 1195, 1067, 1040, 948 cm$^{-1}$; HRMS-ESI m/z 407.3154 ([M+H]$^+$, C$_{25}$H$_{43}$O$_4$ requires 407.3156).

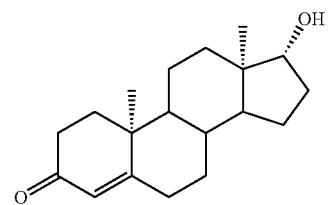 [SMILES: C[C@@]12CCC(=O)C=C1CCC1C2CC[C@]2(C)C1CC[C@H]2O]

ent-Testosterone (53). (71%) white solid; R$_f$=0.22 (1:1 EA/hex); $^1$H NMIR (400 MHz, CDCl$_3$) δ 5.73 (s, 1H), 3.68-3.62 (m, 1H), 2.48-2.23 (m, 4H), 2.13-1.98 (m, 2H), 1.89-1.23 (m, 10H), 1.19 (s, 3H), 1.13-0.88 (m, 4H), 0.79 (s, 3H); $^{13}$C NMR (150 MHz, CDCl$_3$) δ 199.8, 171.5, 124.1, 81.8, 54.1, 50.7, 43.0, 38.9, 36.6, 35.9, 35.8, 34.1, 33.0, 31.7, 30.6, 23.5, 20.8, 17.6, 11.2; IR (solid): 3391, 2930, 2880, 1645, 1612, 1229, 1056 cm$^{-1}$; HRMS-ESI m/z 289.2158 ([M+H]$^+$, C$_{19}$H$_{29}$O$_2$ requires 289.2162).

The following compounds were prepared based on previously published methods (Auchus et al. *Arch. Biochem. Biophys.* 2003, 409, 134-144).

ent-(17β)-17-Hydroxyandrost-5-en-3-one cyclic 3-(1,2-ethanediyl acetal) (54). (71%) white solid; R$_f$=0.42 (1:1 EA/hex); $^1$H NMR (400 MHz, CDCl$_3$) δ 5.34-5.30 (m, 1H), 3.96-3.89 (m, 4H), 3.62 (t, 1H, J=8.4 Hz), 2.55 (dq, 1H, J=14.2, 3.0 Hz), 2.12-1.90 (m, 3H), 1.83-0.88 (m, 16H), 1.01 (s, 3H), 0.74 (s, 3H); $^{13}$C NMR (100 MHz, CDCl$_3$) δ 140.4, 122.1, 109.6, 82.0, 64.6, 64.4, 51.5, 50.0, 42.9, 42.0, 36.9, 36.8, 36.5, 32.1, 31.5, 31.2, 30.7, 23.7, 20.8, 19.1, 11.2; IR (solid): 3213, 2933, 2886, 1093, 1058 cm$^{-1}$; HRMS-ESI m/z 333.2426 ([M+H]$^+$, C$_{21}$H$_{33}$O$_3$ requires 333.2424).

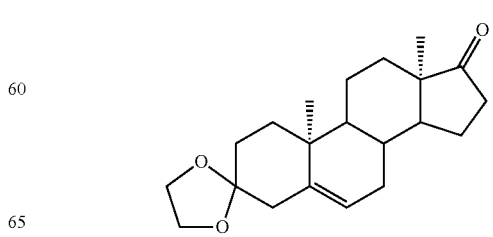

ent-Androst-5-ene-3,17-dione cyclic 3-(1,2-ethanediyl acetal) (55). (95%) white solid; $R_f$=0.52 (1:1 EA/hex); $^1$H NMR (400 MHz, CDCl$_3$) δ 5.41-5.36 (m, 1H), 3.99-3.92 (m, 4H), 2.59 (dq, 1H, J=14.0, 2.8 Hz), 2.46 (dd, 1H, J=19.2, 8.0 Hz), 2.17-2.03 (m, 3H), 1.99-1.90 (m, 1H), 1.88-1.08 (m, 13H), 1.06 (s, 3H), 0.89 (s, 3H); '$^{13}$C NMR (100 MHz, CDCl) δ 221.4, 140.6, 121.6, 109.5, 64.7, 64.5, 51.9, 50.0, 47.8, 42.0, 36.9, 36.4, 36.0, 31.7, 31.6, 31.2, 30.8, 22.1, 20.5, 19.1, 13.8; IR (solid): 2946, 2933, 2883, 1735, 1373, 1092, 992 cm$^{-1}$; HRMS-ESI m/z 331.2283 ([M+H]$^+$, C$_{21}$H$_{31}$O$_3$ requires 331.2268).

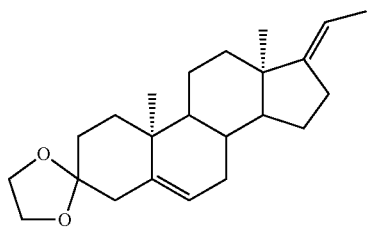 [SMILES: C/C=C1\CCC2C3CC=C4CC5(CC[C@@]4(C)C3CC[C@@]12C)OCCO5]

ent-[(17Z)-Pregna-5,17(20)-dien-3-one cyclic (1,2-ethanediyl acetal)] (56). (76%) white solid; Rf=0.73 (1:1 BA/hex, KMnO4 stain); $^1$H NMR (400 MHz, CDCl) δ 5.38-5.36 (m, 1H), 5.17-5.10 (m, 1H), 4.00-3.92 (m, 4H), 2.61-2.54 (m, 1H), 2.42-1.07 (m, 21H), 1.05 (s, 3H), 0.90 (s, 3H); $^{13}$C NMR (100 MHz, CDCl) δ 150.5, 140.4, 122.3, 113.7, 109.7, 64.7, 64.4, 56.6, 49.9, 44.3, 42.0, 37.2, 36.9, 36.5, 31.8 31.6 (2C), 31.3, 24.7, 21.4, 19.1, 16.8, 13.4; JR (solid): 2930, 2881, 1421, 1370, 1255, 1089, 955 cm$^{-1}$; HRMS-ESI m/z 343.2625 ([M+H]$^+$, C$_{23}$H$_5$O$_2$ requires 343.2632).

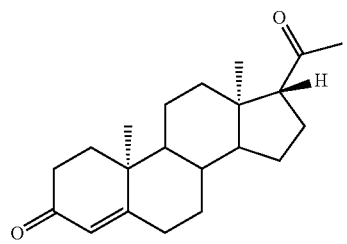 [SMILES: CC(=O)[C@@H]1CCC2C3CCC4=CC(=O)CC[C@@]4(C)C3CC[C@]21C]

ent-Progesterone (57). (78%) white solid; $R_f$=0.41 (1:1 EA/hex); [α]$^{23}_D$ –200.2 (c=1.00, CHCl) [lit. –200 (c=0.25, CHCl)]$^5$ '$^1$H NIMR (400 MHz, CDCl) δ 5.71 (s, 1H), 2.51 (t, 1H, J=9.0 Hz), 2.46-0.91 (m, 19H), 2.10 (s, 3H), 1.16 (s, 3H), 0.64 (s, 3H); $^{13}$C NMR (100 MHz, CDCl$_3$) δ 209.6, 199.7, 171.2, 124.1, 63.7, 56.2, 53.8, 44.1, 38.8 (2C), 35.9, 35.7, 34.1, 33.0, 32.1, 31.7, 24.6, 23.0, 21.2, 17.6, 13.5; IR (solid): 2943, 2925, 2850, 1697, 1660, 1615, 1437, 1356, 1194, 1162, 948, 871 cm$^{-1}$; HRMS-ESI m/z 315.2319 ([M+H]$^+$, C$_{21}$H$_{31}$O$_2$ requires 315.2319).

Enantiomeric Progesterone Derivatives

The following compounds were prepared according to the procedures described above for the synthesis of P1-31 and related series analogues.

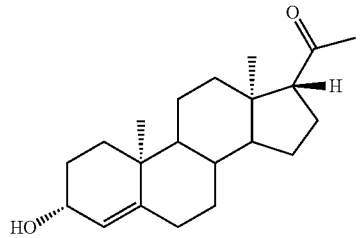 [SMILES: CC(=O)[C@@H]1CCC2C3CCC4=C[C@H](O)CC[C@@]4(C)C3CC[C@]21C]

3α-Hydroxy-ent-progesterone (58). (47%) white solid; $R_f$=0.31 (99:5 DCM/MeOH, PMA stain); $^1$H NMR (400 MHz, CDCl$_3$) δ 5.29 (d, 1H, J=1.6 Hz), 4.18-4.13 (m, 1H), 2.45-0.74 (m, 21H), 2.11 (s, 3H), 1.04 (s, 3H), 0.62 (s, 3H); $^{13}$C NMR (100 MHz, CDCl$_3$) δ 209.9, 147.3, 123.8, 68.1, 63.9, 56.5, 54.5, 44.3, 39.1, 37.5, 36.1, 35.6, 33.1, 32.3, 31.7, 29.6, 24.6, 22.9, 21.2, 19.1, 13.5; IR (solid): 3400, 2932, 2848, 1701, 1662, 1355, 917, 730 cm$^{-1}$, HRMS-ESI m/z 299.2370 ([M+H—H$_2$O]$^+$, C$_{21}$H$_{31}$O requires 299.2369).

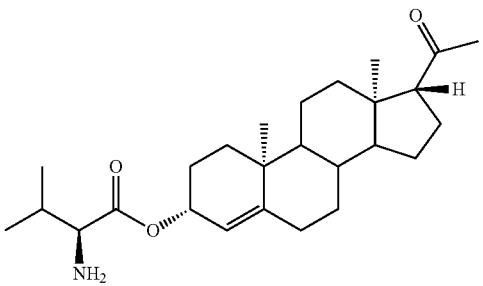 [SMILES: CC(=O)[C@@H]1CCC2C3CCC4=C[C@H](OC(=O)[C@@H](N)C(C)C)CC[C@@]4(C)C3CC[C@]21C]

N-Fmoc-L-valine-3α-ent-progesterone (59). (83%) white foam; $^1$H NMR (400 MHz, CDCl$_3$) δ 7.78 (d, 2H, J=7.6 Hz), 7.61 (d, 2H, J=7.6 Hz), 7.41 (1, 2H, J=7.6 Hz), 7.33 (t, 2H, J=7.6 Hz), 5.34 (d, 1H, J=9.2 Hz), 5.31 (s, 1H), 5.24 (s, 1H), 4.40 (d, 2H, J=7.2 Hz), 4.31 (dd, 1H, J=9.2, 4.8 Hz), 4.25 (t, 1H, J=6.8 Hz), 2.53 (t, 1H, J=8.8 Hz), 2.30-0.70 (m, 20H), 2.12 (s, 3H), 1.07 (s, 3H), 0.99 (d, 3H, J=6.8 Hz), 0.93 (d, 3H, J=7.2 Hz), 0.64 (s, 3H); $^{13}$C NMR (100 MHz, CDCl$_3$) δ 209.8, 172.1, 156.5, 149.8, 144.2, 144.0, 141.5, 127.9, 127.3, 125.3, 120.2, 119.0, 72.1, 67.2, 63.7, 59.2, 56.5, 54.2, 47.4, 44.3, 39.0, 37.5, 36.0, 35.1, 33.0, 32.3, 31.6, 25.3, 24.6, 23.0, 19.2, 19.0, 17.7, 13.6; IR (solid): 3360, 2935, 1702, 1388, 1351, 1205, 734 cm$^{-1}$.

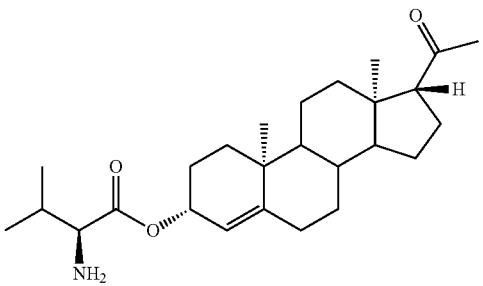 [SMILES: CC(=O)[C@@H]1CCC2C3CCC4=C[C@H](OC(=O)[C@@H](N)C(C)C)CC[C@@]4(C)C3CC[C@]21C]

3α-L-Valine-ent-progesterone (60). (87%) clear oil; $^1$H NMR (400 MHz, CDCl$_3$) δ 5.32-5.28 (m, 2H), 5.23 (d, 1H, J=0.8 Hz), 3.28 (d, 1H, J=5.2 Hz), 2.53 (t, 1H, J=9.2 Hz), 2.30-0.75 (m, 21H), 2.12 (s, 3H), 1.07 (s, 3H), 0.98 (d, 3H, J=7.2 Hz), 0.90 (d, 3H, J=6.8 Hz), 0.64 (s, 3H); $^{13}$C NMR (100 MHz, CDCl$_3$) δ 209.8, 175.7, 149.5, 119.3, 71.3, 63.9, 60.2, 56.5, 54.2, 44.3, 39.0, 37.5, 36.0, 35.1, 33.0, 32.3 (2C), 31.8, 25.3, 24.6, 23.0, 21.2, 19.6, 19.0, 17.3, 13.6; IR (solid): 2933, 2850, 1724, 1705, 1385, 1357, 1178, 977 cm$^{-1}$; HRMS-ESI m/z 416.3158 ([M+H]$^+$, C$_{26}$H$_{42}$NO$_3$ requires 416.3159).

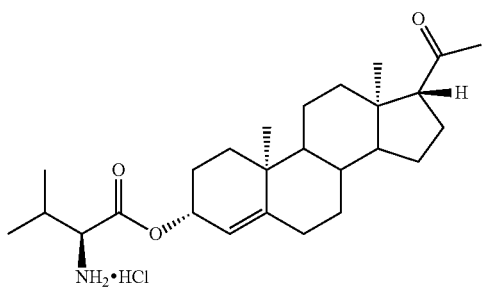

3α-L-Valine-ent-progesterone-HCl (P2-13). (58%) off-white solid; $^1$H NMR (400 MHz, DMSO) δ 8.53 (bs, 3H), 5.28 (t, 1H, J=8.0 Hz), 5.22 (s, 1H), 3.82 (d, 1H, J=4.8 Hz), 3.34 (s, 1H), 2.56 (t, 1H, J=9.2 Hz), 2.25-0.74 (m, 21H), 2.05 (s, 3H), 1.02 (s, 3H), 0.99 (d, 3H, J=6.8 Hz), 0.94 (d, 3H, J=6.8 Hz), 0.54 (s, 3H); $^{13}$C NMR (100 MHz, CDCl$_3$) δ 209.7, 168.5, 150.0, 118.7, 73.8, 63.9, 59.2, 56.5, 54.2, 44.2, 39.1, 37.5, 36.0, 35.2, 33.1, 32.3, 31.8, 30.3, 25.4, 24.6, 23.0, 21.2, 19.2, 18.9 (2C), 13.6; IR (solid): 2932, 2849, 2600, 1737, 1702, 1379, 1354, 1219, 1110 cm$^{-1}$; HRMS-ESI m/z 416.3160 ([M+H]$^+$, C$_{26}$H$_{42}$NO$_3$ requires 416.3159); Anal. Calcd for C$_{26}$H$_{41}$ClNO$_3$+½H$_2$O: C, 67.73; H, 9.40; N, 3.04. Found C, 67.39; H, 9.24; N, 3.01.

Example 7

Solubility of Steroid Analogues

Figure 2:
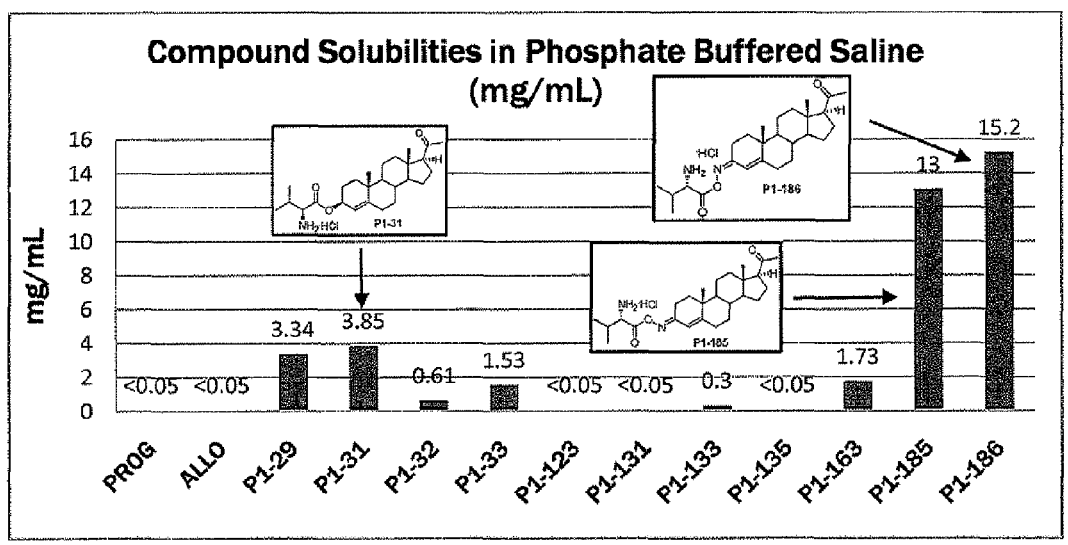
FIG. 2 shows the solubility of selected steroid analogues in phosphate buffered saline.
Figure 3:
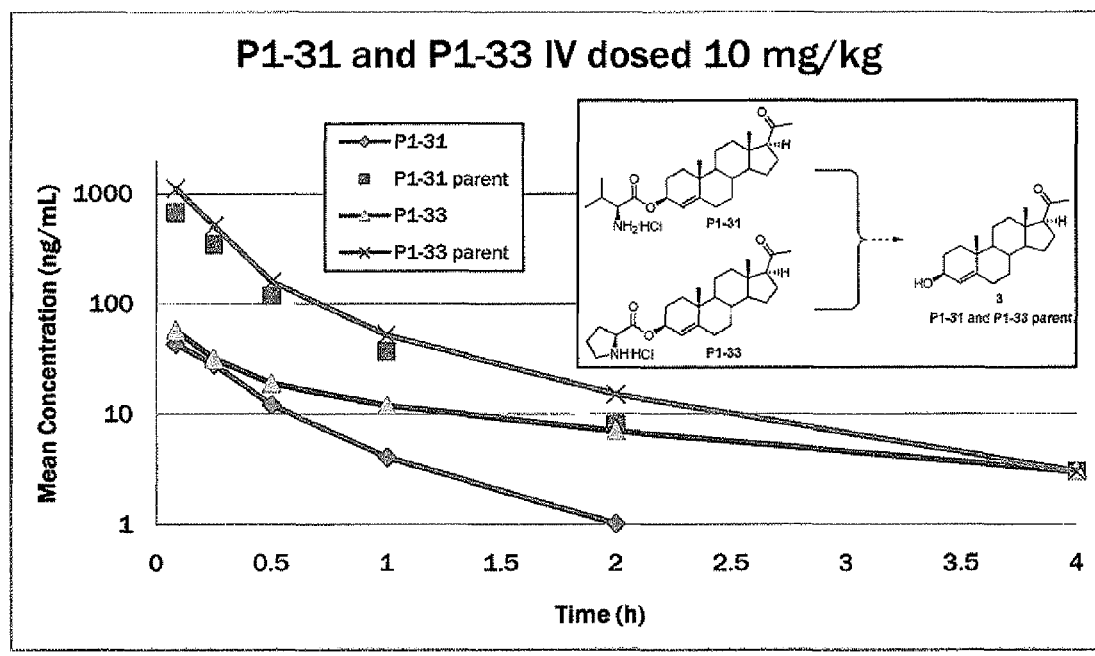
FIG. 3 shows pharmacokinetic data of steroid analogues P1-31 and P1-33 after dosing at 10 mg/kg.

Several compounds were screened for solubility (FIG. 2). Solubility testing was done in phosphate buffered saline, which is considered to be a good model system for physiological conditions. Compounds were added in small portions at room temperature with stirring until a visible endpoint of saturation was reached. Neither PROG nor ALLO showed any degree of solubility by this method (designated at <0-05 mg/mL solubility). The valine coupled C-3-β-hydroxy PROG derivative P1-31 showed the best solubility (3.85 mg/mL) of the different amino acid substituted analogues within that series. Compound P1-133, the 3α-5β ALLO isomer, showed the highest solubility within that group, (0.33 mg/mL). Both the E and Z oxime derivatives P1-185 and P1-186 showed excellent solubility, with values of 13.0 and 15.2 mg/mL respectively.

Example 8

In Vitro Screening

Primary cortical cells were seeded in multi-well plates and cultured for 8 days. Cells were then pre-treated with various concentrations of different PROG analogues (0.1, 1, 5, 10, 20, 40, and 80 μM) for 24 h. Cells were next exposed to glutamate (0.5 μM) for the following 24 h. Cytotoxicity was assessed by the MTT [3-(4,5-dimethylthiazol-2-yl)-2,5-diphenyltetrazolium bromide] assay, which is based on the ability of a mitochondrial dehydrogenase enzyme from viable cells to cleave the tetrazolium rings of the pale yellow MTT. This reaction forms dark blue formazan crystals which are largely impermeable to cell membranes, thus resulting in their accumulation within healthy cells. Solubilization of the cells results in the liberation of the crystals, which are then also solubilized. The number of surviving cells is directly proportional to the level of the formazan product created.

Table 2 below shows the effect of several compounds of the invention compared with PROG and ALLO in the reduction in cortical neuron cell death caused by glutamate toxicity. Several of the derivatives proved to be significantly more potent than PROG or ALLO when the compounds are compared at the 5 μM concentration. The P1-185 and P1-186 oxime prodrug compounds achieved the highest levels of cell survival among the compounds screened. The C-20 reduced PROG derivative P1-57 and the ent-PROG derivative P2-13 also showed significant reductions in cell death.

TABLE 2

| | Reduction in cortical neuron cell death caused by glutamate toxicity. | |
|---|---|---|
| compound | reduction in cell death best concentration (%) | reduction in cell death at 5 μM (%) |
| PROG | 42 (20 μM) | 4 |
| ALLO | 40 (80 μM) | −3 |
| P1-57 | 30 (10 μM) | 23 |
| P1-185 | 27 (5 μM) | 27 |
| P1-186 | 34 (5 μM) | 34 |
| P2-13 | 26 (5 μM) | 26 |

Example 9

Pharmacokinetic Data

Select compounds were submitted for pharmacokinetic analysis in a non-injury whole animal rat study. The C-3-β-hydroxy PROG derivatives P1-31 and P1-33 were chosen in order to observe any potential differences in the stability of the compounds that may be attributable to the amino acid component. The natural ALLO derivative P1-131 was selected based on its activity in the cerebral edema assay and as an example of a compound containing a saturated A ring. Finally, the oxime derived compound P1-186 was also submitted in order to evaluate its potential to act as a prodrug in vivo as envisioned.

Figure 4:
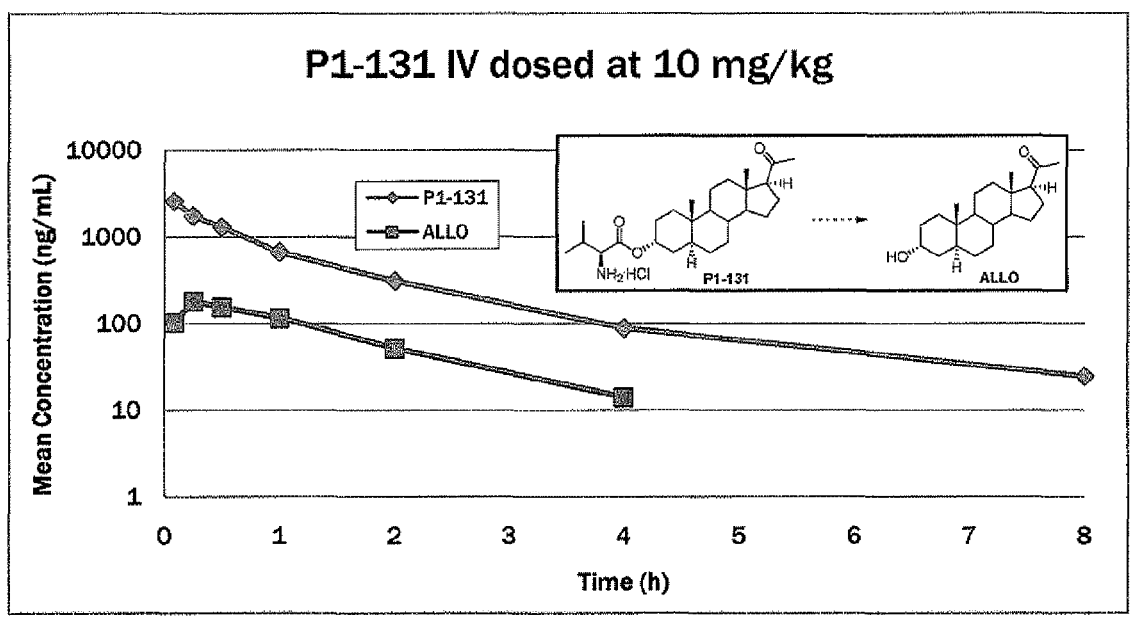
FIG. 4 shows pharmacokinetic data of steroid analogue P1-131 after dosing at 10 mg/kg.

The compounds were intravenously (IV) dosed at 10 mg/kg and serum samples were taken at several time points over the course of 12 h. Serum concentration levels were determined for the analogues, as well as for their respective parent compound. The derivatives P1-31 and P1-33 behaved very similarly in vivo (FIG. 7). The amino acid side chain in both compounds was cleaved almost immediately to give rapid conversion to their mutual parent, the C-3-β-hydroxy compound 3. However, in the case of the ALLO derivative P1-131, the valine tethered compound was stable for a prolonged period of time and only gradually converted to its parent, ALLO (2, FIG. 4). The data indicates a distinct difference in the susceptibility of the amino acid side chain to hydrolysis resulting from relatively small differences in saturation and conformation. The more sterically congested A-ring of P1-131 could be thought to provide some protection to active esterases relative to the unsaturated A-ring of P1-31 type compounds, or perhaps also important is the relative α-(P1-131) or β-(P1-31) face orientation of the side chain.

Figure 5:
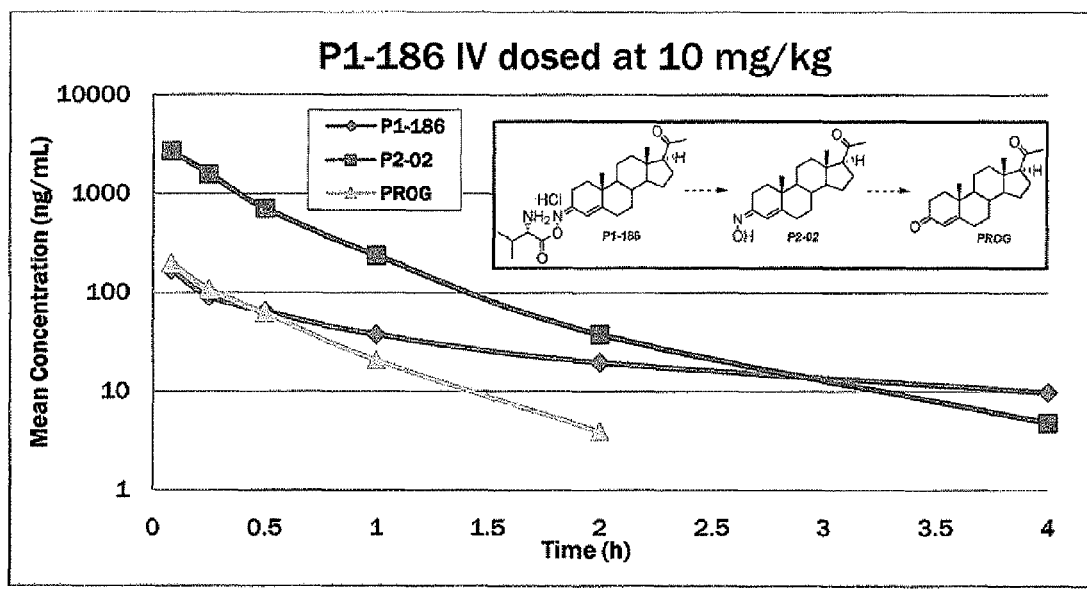
FIG. 5 shows pharmacokinetic data of steroid analogue P1-186 after dosing at 10 mg/kg.

The oxime based compound P1-186 did indeed generate PROG in vivo when dosed either IV or intraperitoneally (IP) at 10 mg/kg (FIG. 5). The PROG levels observed via both modes of administration reached a maximum of approximately 100 ng/mL, which compares favorably to a previously reported maximum serum concentration of 28 ng/mL when PROG was administered IP at 4 mg/kg to male rats (Wright et al., *J. Neurotrama*, 2001, 18, 901-094). Despite the observance of PROG however, the amino acid tether of compound P1-186 is readily cleaved to give primarily the parent oxime P2-02 (FIG. 8), which is stable in vivo for several hours. The potential implication of this data is that it is the intermediate oxime compound (P2-02) that may be responsible for achieving the neuroprotective effects observed in both the in vitro and cerebral edema assays, not progesterone, as might have been suspected.

The above embodiments are provided merely as non-limiting examples to which the invention should not be limited.

What is claimed is:

1. A pharmaceutical composition comprising a pharmaceutically acceptable carrier and a steroid compound of the Formula VII:

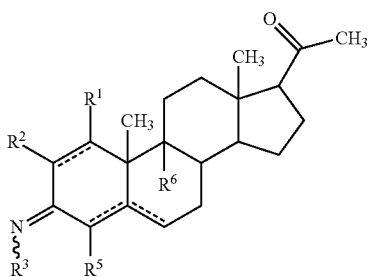

or a pharmaceutically acceptable salt-thereof, wherein:
$R^1$ $R^2$, $R^5$ and $R^6$ are independently hydrogen, alkyl, halogen, hydroxyl cycloalkyl, cycloalkenyl, alkenyl, alkynyl, aryl, alkylaryl, arylalkyl, heterocyclic, heteroaryl, amino, thiol, alkoxy, sulfide, nitro, cyano, azide, sulfonyl, acyl, carboxyl, an ester, an amide, carbamate, carbonate, an amino acid residue or a carbohydrate;

$R^3$ —$OR^{11}$;

$R^{11}$ is —C(O)R', where R' is alkyl, or the residue of an amino acid; and the dotted line indicates the presence of either a single bond or a double bond, wherein the valences of a single bond are completed by hydrogens.

2. A pharmaceutical composition of claim 1, wherein $R^1$, $R^2$, $R^5$ and $R^6$ are independently hydrogen or alkyl.

3. A pharmaceutical composition of claim 1 wherein the compound is selected from,

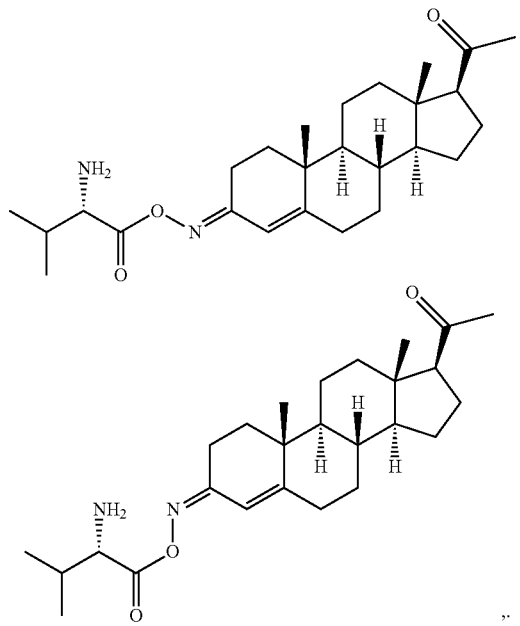

* * * * *